US012370207B2

(12) United States Patent
Cheung et al.

(10) Patent No.: US 12,370,207 B2
(45) Date of Patent: Jul. 29, 2025

(54) LOW-INTENSITY TREATMENT OF HEMATOLOGICAL DISORDERS

(71) Applicant: Celator Pharmaceuticals, Inc., Palo Alto, CA (US)

(72) Inventors: Ronald Cheung, Palo Alto, CA (US); Stefan Faderl, Reno, NV (US); Qi Wang, Pennington, NJ (US)

(73) Assignee: Celator Pharmaceuticals, Inc., Palo Alto, CA (US)

( * ) Notice: Subject to any disclaimer, the term of this patent is extended or adjusted under 35 U.S.C. 154(b) by 638 days.

(21) Appl. No.: 17/338,561

(22) Filed: Jun. 3, 2021

(65) Prior Publication Data
US 2021/0393665 A1    Dec. 23, 2021

Related U.S. Application Data

(63) Continuation of application No. 17/279,556, filed as application No. PCT/US2019/052952 on Sep. 25, 2019, now abandoned.

(60) Provisional application No. 62/772,372, filed on Nov. 28, 2018, provisional application No. 62/736,393, filed on Sep. 25, 2018.

(51) Int. Cl.
| *A61K 31/7068* | (2006.01) |
| *A61K 9/00* | (2006.01) |
| *A61K 9/127* | (2025.01) |
| *A61K 31/53* | (2006.01) |
| *A61K 31/553* | (2006.01) |
| *A61K 31/635* | (2006.01) |
| *A61K 31/704* | (2006.01) |
| *A61K 39/395* | (2006.01) |
| *A61P 35/02* | (2006.01) |

(52) U.S. Cl.
CPC ........ *A61K 31/7068* (2013.01); *A61K 9/0019* (2013.01); *A61K 9/127* (2013.01); *A61K 31/53* (2013.01); *A61K 31/553* (2013.01); *A61K 31/635* (2013.01); *A61K 31/704* (2013.01); *A61K 39/3955* (2013.01); *A61P 35/02* (2018.01)

(58) Field of Classification Search
CPC .. A61K 31/7068; A61K 9/0019; A61K 31/53; A61K 31/553; A61K 31/635; A61K 31/704; A61K 39/3955; A61K 45/06; A61K 2300/00; A61K 9/127; A61K 31/496; A61P 35/02
See application file for complete search history.

(56) References Cited

U.S. PATENT DOCUMENTS

| 7,238,367 B2 | 7/2007 | Tardi et al. |
| 7,744,921 B2 | 6/2010 | Tardi et al. |
| 7,850,990 B2 | 12/2010 | Tardi et al. |
| 8,022,279 B2 | 9/2011 | Mayer et al. |
| 8,092,828 B2 | 1/2012 | Louie et al. |
| 8,431,806 B2 | 4/2013 | Mayer et al. |
| 8,518,437 B2 | 8/2013 | Tardi et al. |
| 9,271,931 B2 | 3/2016 | Tardi et al. |
| 10,028,912 B2 | 7/2018 | Cabral-Lilly et al. |
| 10,166,184 B2 | 1/2019 | Cabral-Lilly et al. |
| 2008/0199515 A1* | 8/2008 | Louie ............. A61P 35/00 514/50 |
| 2021/0393665 A1* | 12/2021 | Cheung ............ A61K 31/53 |
| 2024/0252526 A1* | 8/2024 | Faderl ............. A61P 35/02 |

FOREIGN PATENT DOCUMENTS

| CA | 2678332 | 8/2008 | |
| JP | 2010-519224 | 6/2010 | |
| WO | WO 2008/101214 A2 | 8/2008 | |
| WO | WO-2017083592 A1 * | 5/2017 | ......... A61K 31/407 |
| WO | WO-2018023025 A1 * | 2/2018 | ............ A61K 35/17 |
| WO | WO 2018/101214 A1 | 6/2018 | |

OTHER PUBLICATIONS

IDHIFA. USPTO Trademark Registry. Registered 2017. (Year: 2017).*
Schnur, M. B. Body Mass Index and Body SurfaceArea: What's the Difference? Nursing Center. Aug. 23, 2017. Web. Nursingcenter.com. (Year: 2017).*
Vyxeos. USPTO Trademark Registry. Registered 2019. (Year: 2019).*
Mylotarg. USPTO Trademark Registry. Registered 2020. (Year: 2020).*
Celator Pharmaceuticals, Inc., JP 2010519224. English Translation. (Year: 2010).*
Heiblig, M., et al. Mediterr. J. Hematol. Infect. Dis. 2016; 8(1): e2016009. (Year: 2016).*
Tardi, P., et al. Leukemia Research. 2009, 33, 129-139. (Year: 2009).*
Wei, A., et al. Blood. 2016, 128 (22) : 102. (Year: 2016).*
Murphy, T., et al. Expert Opinion on Pharmacotherapy. 2017, 18:16, 1765-1780. (Year: 2017).*
Walter, R. B., et al. Haematologica. Mar. 2018;103(3):e106-e109. (Year: 2018).*
Anderson et al., "The BCL2 selective inhibitor venetoclax induces rapid onset apoptosis of CLL cells in patients via a TP53-independent mechanism," Blood (2016) 127(25):3215-3224.
Burnett et al., "A comparison of low-dose cytarabine and hydroxyurea with or without all-trans retinoic acid for acute myeloid leukemia and high-risk myelodysplastic syndrome in patients not considered fit for intensive treatment," Cancer (2007) 109(6):1114-1121.

(Continued)

Primary Examiner — Eric Olson
Assistant Examiner — Samuel L Galster
(74) Attorney, Agent, or Firm — Morgan, Lewis & Bockius LLP

(57) ABSTRACT

The invention relates to compositions and methods for treating patients with hematological proliferative disorders who are ineligible for treatment with standard intensive chemotherapy, using low intensity treatment with CPX-351, a liposomal composition of daunorubicin and cytarabine.

13 Claims, 37 Drawing Sheets

(56) References Cited

OTHER PUBLICATIONS

Dinardo et al., "Venetoclax combined with decitabine or azacitidine in treatment-naive, elderly patients with acute myeloid leukemia," *Blood* (2019) 113(1):7-17.

Friberg LE, et al., "Model of chemotherapy-induced myelosuppression with parameter consistency across drugs," *J Clin Oncol.* (2002) 20(24):4713-4721.

International Search Report and Written Opinion for PCT/US19/52952, mailed Dec. 12, 2019, 11 pages.

Jacob et al., "Decitabine Compared with Low-Dose Cytarabine for the Treatment of Older Patients with Newly Diagnosed Acute Myeloid Leukemia: A Pilot Study of Safety, Efficacy, and Cost-Effectiveness," Advances in Hematology (2015) 7 pages.

Lancet JE, et al., "CPX-351 (cytarabine and daunorubicin) Liposome for Injection Versus Conventional Cytarabine Plus Daunorubicin in Older Patients With Newly Diagnosed Secondary Acute Myeloid Leukemia," J Clin Oncol. (2018) 36(26):2684-2692.

McCullough J., "Overview of platelet transfusion," *Semin Hematol.* (2010) 47(3):235-242.

M.D. Anderson Cancer Center, "Liposome-encapsulated Daunorubicin-Cytarabine and Gemtuzumab Ozogamicin in Treating Patients With Relapsed or Refractory Acute Myeloid Leukemia (AML) or High Risk Myelodysplastic Syndrome," Study NCT03672539. Sep. 13, 2018; downloaded from the internet <https://clinicaltrials.gov/ct2/history/NCT03672539?A=1&B=1&C=merged#StudyPageTop> on Nov. 20, 2019; pp. 1-9.

M.D. Anderson Cancer Center, "Liposome-encapsulated Daunorubicin-Cytarabine and Venetoclax in Treating Participants With Relapsed, Refractory or Untreated Acute Myeloid Leukemia," Study NCT03629171. Aug. 14, 2017; downloaded from the internet <https://clinicaltrials.gov/ct2/history/NCT03629171?A=2&B=2&C=merged#StudyPageTop> on Nov. 20, 2019; pp. 1-7.

Tallman et al., "Drug therapy for acute myeloid leukemia," Blood (2005) 106(4):1154-1163.

Wang et al., "CPX-351 Population Pharmacokinetics in Patients with Hematologic Malignancies," *Blood.* 2017;130 (Suppl_1), Abstract 5064.

Wei et al, "Updated Safety and Efficacy Results of Phase 1/2 Study of Venetoclax Plus Low-Dose Cytarabine in Treatment-Naïve Acute Myeloid Leukemia Patients Aged ≥65 Years and Unfit for Standard Induction Therapy," Abstract S473, Oral Presentation during EHA22; Jun. 24, 2017; downloaded from the internet <https://library.ehaweb.org/eha/2017/22nd/181760/andrew.wei.updated.safety.and.efficacy.results.of.phase.1.2.study.of.html> on Nov. 20, 2019; pp. 1-2.

Borthakur, G. et al., "Phase II Study of CPX-351 (Cytarabine:Daunorubicin) Liposome Injection in Patients (Pts) with Newly Diagnosed Acute Myeloid Leukemia (AML) at High Risk for Induction Mortality," Blood, 2017, 130 (Suppl_1):892, 6 pages.

NIH, U.S. National Library of Medicine, ClinicalTrials.gov, NCT03629171, "Liposome-encapsulated Daunorubicin-Cytarabine and Venetoclax in Treating Participants With Relapsed, Refractory or Untreated Acute Myeloid Leukemia," Aug. 14, 2018, https://www.clinicaltrials.gov/study/NCT03629171?tab=history@a=2.

Stahl, M. et al., "Novel Therapies for Acute Myeloid Leukemia: Are We Finally Breaking the Deadlock?", Targ Oncol, (2017) 12:413-447.

\* cited by examiner

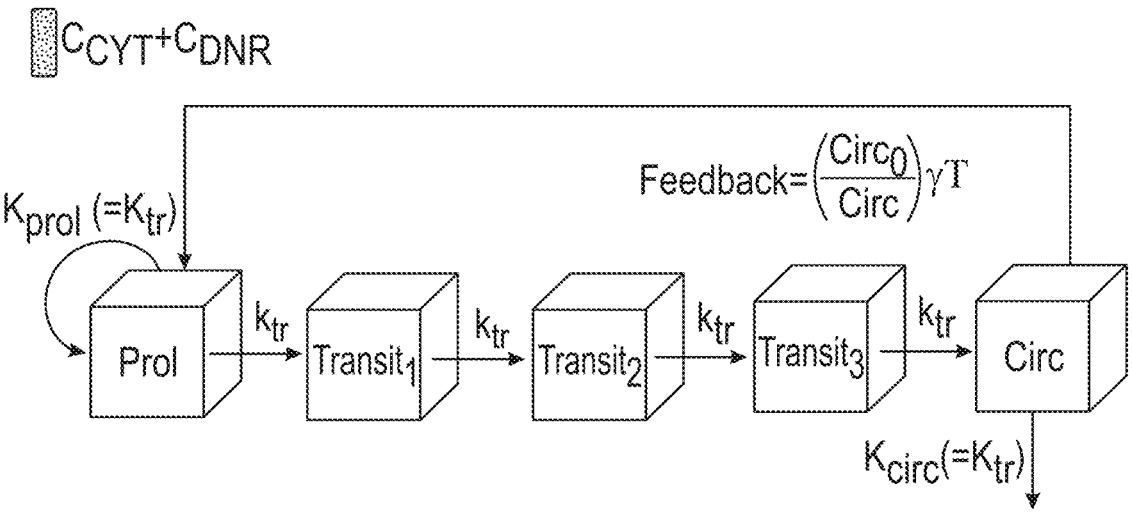

PK-PD Model for Myelosuppression $$\frac{dProl}{dt} = k_{prol} \cdot Prol \cdot \left(1 - \frac{Imax \cdot (C_{CYT} + C_{DNR})^{\gamma}}{IC_{50}^{\gamma} + (C_{CYT} + C_{DNR})^{\gamma}}\right) \left(\frac{Circ_0}{Circ}\right)^{\gamma\tau} - k_{tr} \cdot Prol$$

$$\frac{dTransit_1}{dt} = k_{tr} \cdot Prol - k_{tr} \cdot Transit_1$$

$$\frac{dTransit_2}{dt} = k_{tr} \cdot Transit_1 - k_{tr} \cdot Transit_2$$

$$\frac{dTransit_3}{dt} = k_{tr} \cdot Transit_2 - k_{tr} \cdot Transit_3$$

$$\frac{dCirc}{dt} = k_{tr} \cdot Transit_3 - k_{circ} \cdot Circ$$

FIG. 1A

Day 1. Vyxeos is Dosed on Day 1

Day 1, 3. Vyxeos is Dosed on Day 1 and 3

Day 1, 5. Vyxeos is Dosed on Day 1 and 5

Day 1, 8. Vyxeos is Dosed on Day 1 and 8

Day 1, 8, 15. Vyxeos is Dosed on Day 1, 8, and 15

Day 1, 3, 5. Vyxeos is Dosed on Day 1,3 and 5 at 100 unit/m2

7+3. Standard of Care 7 Days Cytarabine +3 Days Daunorubicin

| | IC50(pM) |
|---|---|
| CPX-351 | 41096 |
| CPX-351+ Venetoclax | 3.2* |
| Venetoclax | 11847* |

| CD 34 Status | IDH1/2 Status | FLT3 Status | NPM status |
|---|---|---|---|
| CD 34 | Wild Type | ITD Mutant | Wild Type |

*=Incomplete Curve

FIG. 12B

| Test group | IC50(pM) |
|---|---|
| CPX-351 | 2014 |
| CPX-351+ Venetoclax | 1084 |
| Venetoclax | 8568 |

| Cd34 Status | IDH1/2 Status | FLT3 Status | NPM Status |
|---|---|---|---|
| CD34+Small Subset/Variable | IDH2 Mutant (R140Q) | ITD Mutant | Wild Type |

FIG. 13B

LOW-INTENSITY TREATMENT OF HEMATOLOGICAL DISORDERS

CROSS-REFERENCE TO RELATED APPLICATIONS

This application is a continuation of U.S. Ser. No. 17/279,556 having an international filing date of 25 Sep. 2019, which is a national stage application under 35 U.S.C. § 371 of International Application No. PCT/US2019/052952 having an international filing date of 25 Sep. 2019, which claims priority of U.S. Provisional Application No. 62/736,393, filed 25 Sep. 2018 and U.S. Provisional Application No. 62/772,372, filed 28 Nov. 2018, the disclosures of which are herein incorporated by reference in its entirety.

TECHNICAL FIELD

The invention relates to compositions and methods for treating patients who are ineligible for treatment with conventional chemotherapy. More particularly, the invention concerns the treatment of hematological conditions that are susceptible to treatment with combinations of cytidine analogues and anthracyclines.

BACKGROUND ART

Combination chemotherapies comprising cytidine analogues and anthracycline agents have been well studied for treatment against various cancers or hematologic proliferative disorders. Drug cocktails of the cytidine analogue, cytarabine, and an anthracycline such as daunorubicin demonstrate some efficacy in patients with hematologic malignancies. See, e.g., Tallum et al., *Blood* 106:2243 (2005).

Cytarabine (cytosine arabinoside, Ara-C or 1-β-D-arabinofuranosylcytosine) is a cell cycle phase-specific antineoplastic agent, affecting cells predominantly during the S-phase of cell division. Intracellularly, cytarabine is converted into cytarabine-5'-triphosphate (ara-CTP), which is the active metabolite. The mechanism of action is not completely understood, but it appears that ara-CTP acts primarily through inhibition of DNA polymerase. Incorporation into DNA and RNA may also contribute to cytarabine cytotoxicity. Cytarabine is cytotoxic to a wide variety of proliferating mammalian cells in culture.

Daunorubicin hydrochloride is the hydrochloride salt of an anthracycline cytotoxic antibiotic produced by a strain of *Streptomyces coeruleorubidus*. Daunorubicin has antimitotic and cytotoxic activity through a number of proposed mechanisms of action. Daunorubicin forms complexes with DNA by intercalation between base pairs. It inhibits topoisomerase II activity by stabilizing the DNA-topoisomerase II complex, preventing the religation portion of the ligation-religation reaction that topoisomerase II catalyzes. Single strand and double strand DNA breaks result. Daunorubicin may also inhibit polymerase activity, affect regulation of gene expression, and produce free radical damage to DNA. Daunorubicin possesses an antitumor effect against a wide spectrum of animal tumors, either grafted or spontaneous.

Since 1973, cytarabine combined with an anthracycline has been the standard first-line therapy for acute myelogenous leukemia (AML), against which other regimens are compared. Until recently, the standard of care for AML has been a combination of cytarabine and daunorubicin administered in the classic "7+3" regimen with cytarabine administered for 7 consecutive days and daunorubicin for the first 3 of those 7 consecutive days. Addition of other agents such as 6-thioguanine or etoposide and changes in the dose or schedule of administration have been studied to improve outcomes, but while incremental gains have been made, the 40-year old use of an anthracycline and cytarabine remained the basis for standard induction treatment in AML.

In 2017, Vyxeos® (also known as "CPX-351" and used interchangeably here), a fixed-dose liposomal combination of cytarabine and daunorubicin at a 5:1 ratio which delivers the administered ratio to the patient over time was approved by the FDA for the treatment of adults with two types of high-risk acute myeloid leukemia (AML): newly diagnosed therapy-related AML (t-AML) or AML with myelodysplasia-related changes (AML-MRC). CPX-351 showed a significant improvement in overall survival in these patients compared to the standard 7+3 therapy. Results from earlier clinical studies also showed favorable results for treatment of other leukemias or hematological disorders such as myelodysplastic syndromes (MDS) and certain lymphoblastic leukemias/lymphomas.

Unfortunately, due to age and/or co-morbidities, many patients with hematological malignancies are ineligible to receive standard intensive chemotherapy (ICT), i.e., ISICT patients or subjects, including approximately 50% of AML patients. The standard therapies for these ISICT patients are hypomethylating agents (HMAs) and low dose cytarabine (LDAC). However, the single agent activity of HMAs and LDAC is discouraging with response rates less than about 20% and a median overall survival of only 7-10 months.

Recognizing that there remains a need to achieve improved efficacy for ISICT patients, the present inventors have identified a low-intensity therapy (LIT) of CPX-351 for use in these patients who are ineligible for standard intensive chemotherapy. Furthermore, this LIT therapy provides a myelosuppressive profile that allows it to be combined with other less-intense agents suitable for these patient populations.

Disclosure of the Invention

The present invention overcomes deficiencies in the prior art by providing a low-intensity therapy (LIT) of CPX-351 that is suitable for administration to patients who are ineligible for standard intensive chemotherapy (ISICT patients). In addition, the CPX-351 LIT provides a myelosuppressive profile that allows it to be combined with other agents shown effective in treating leukemias or other hematological proliferative disorders, such as myelodysplastic syndrome (MDS).

Provided herein is a method to treat cancer or a hematologic proliferative disorder in an ISICT subject, said method comprising administering to said subject a pharmaceutical composition comprising a fixed, 5:1 molar ratio of cytarabine and daunorubicin, i.e., CPX-351, wherein the cytarabine and daunorubicin are stably associated with one or more delivery vehicles. Encapsulation in these delivery vehicles allows two or more agents to be delivered to the disease site in a coordinated fashion, thereby assuring that the agents will be present at the disease site at a non-antagonistic ratio. This result will be achieved whether the agents are co-encapsulated in delivery vehicles, or are separately encapsulated in delivery vehicles administered such that non-antagonistic ratios are maintained at the disease site. The pharmacokinetics (PK) of the composition are controlled by the delivery vehicles themselves such that coordinated delivery is achieved (provided that the PK of the delivery systems are comparable). In a specific embodiment, the pharmaceutical composition comprising a fixed, 5:1 molar ratio of cytarabine and daunorubicin is CPX-351, described in U.S. Pat. Nos. 7,238,367; 7,744,921; 7,850,990; 8,022,279; 8,092,828; 8,431,806; 8,518,437; 9,271,931; 10,028,912; and 10,166,184; all of which are incorporated herein by reference in their entireties for any purpose.

In one embodiment, said pharmaceutical composition comprising a fixed, 5:1 molar ratio of cytarabine and daunorubicin is administered once or twice a week. In one embodiment, said pharmaceutical composition comprising a fixed, 5:1 molar ratio of cytarabine and daunorubicin is administered continuously for up to 12 months, or up to 24 months.

In one embodiment, said pharmaceutical composition comprising a fixed, 5:1 molar ratio of cytarabine and daunorubicin is administered at a cytarabine dose of less than 32 mg/m$^2$/day or less than 24 mg/m$^2$/day.

In certain embodiments, provided is a method to treat a hematologic proliferative disorder in an ISICT subject, said method comprising administering to said patient a low-intensity CPX-351 treatment regimen.

In one embodiment, a low-intensity treatment of CPX-351 comprises administering CPX-351 intravenously in 30 minutes to 3 hours. In specific embodiments, CPX-351 is administered intravenously in 90 minutes or less. In specific embodiments, CPX-351 is administered intravenously in about 90 minutes. In certain embodiments, CPX-351 is administered once or twice a week. In certain other embodiments, CPX-351 is administered at a cytarabine dose of less than 32 mg/m$^2$/day or less than 24 mg/m$^2$/day. Preferably, CPX-351 is administered at a cytarabine dose of less than 24 mg/m$^2$/day.

One embodiment of the present invention is a method to treat a hematologic proliferative disorder in a subject ineligible for standard intensive chemotherapy, wherein the cancer or hematologic proliferative disorder is an advanced hematologic cancer. In some embodiments, the advanced hematologic cancer is acute lymphocytic leukemia (ALL), acute myeloid leukemia (AML) or acute promyelocytic leukemia (APL). In other embodiments, the cancer or hematologic proliferative disorder is a hematologic proliferative disorder. In specific embodiments the hematologic proliferative disorder is myelodysplastic syndrome (MDS) or myeloproliferative neoplasm (MPN).

In some embodiments, the subject ineligible for standard intensive chemotherapy has never undergone a previous anti-cancer regimen. In some embodiments, the subject ineligible for standard intensive chemotherapy has not previously received intensive chemotherapy. In some embodiments, the subject ineligible for standard intensive chemotherapy has previously undergone at least one anti-cancer regimen.

In one embodiment, provided is a method to treat a hematologic proliferative disorder in an ISICT subject, said method comprising administering to said ISICT patient a low-dose CPX-351 treatment, wherein said composition is administered prior to said patient receiving any chemotherapy.

In another embodiment, treatment of said subjects ineligible for standard intensive chemotherapy is administered on an outpatient basis or as a home-based treatment.

In another embodiment, provided is a method to reduce the toxicity of cytarabine/anthracycline therapy administered to a patient ineligible for standard intensive chemotherapy by administering to said patient a low-intensity CPX-351 treatment. In some embodiments, reduction in toxicity is measured as a reduction in non-hematopoietic toxicities such as, for example, mucositis or alopecia. A reduction in such toxicities can in turn lead to a reduction in hospitalization, supportive care, morbidity and/or a reduction in induction mortality particularly in patients over 60 years of age and more specifically in patients over the age of 75.

In another embodiment, provided is a method to treat a post-remission hematologic proliferative disorder in an ISICT subject, said method comprising administering to said patient a low-dose CPX-351 treatment, wherein said composition is administered less than 18 months, or less than 12 months, or less than 6 months after one or more initial treatments. In certain embodiments, said one or more initial treatments comprises a hypomethylating agent or low-dose cytosine arabinoside.

In another embodiment, provided is a method to treat hematologic proliferative disorder in an ISICT subject, said method comprising administering to said patient a low-intensity CPX-351 treatment, wherein said treatment provides a therapeutic effect which is greater than that achieved with the current standard of care for said hematologic proliferative disorder in an ISICT patient. In some embodiments, the therapeutic effect is measured as an increase in complete remission rate. In other embodiments, the therapeutic effect is measured as prolongation of complete remission duration and/or prolongation of time to progression and/or prolongation of survival.

In another embodiment, provided is method to improve the safety of cytarabine/anthracycline treatments in an ISICT patient population, said method comprising administering CPX-351 less than 3 times in one week and wherein the CPX-351 dose is less than 24 mg/m$^2$/day. In some embodiments, the improved safety is measured as a reduction in non-hematopoietic toxicities. In specific embodiments, the non-hematopoietic toxicities are mucositis and/or alopecia.

In each of the embodiments of the invention the method can include further administering a hypomethylating agent, or other agent shown effective in treating leukemias.

In specific embodiments, a method of the invention further comprises administering an agent approved for use in a hematological malignancy or disorder. The agent approved for use in a hematological malignancy or disorder can be selected from, for example but not limited to, Mylotarg® (gemtuzumab ozogamicin), midostaurin, venetoclax or Idhifa® (enasidenib).

In additional embodiments, provided herein is a method of treating a hematologic proliferative disorder in a subject ineligible for intensive chemotherapy, said method comprising administering to said patient a low-intensity CPX-351 treatment wherein CPX-351 is administered intravenously at a cytarabine dose of less than 32 mg/m$^2$/day in less than 3 hours and wherein CPX-351 is administered no more than two times per week. In a further embodiment, treatment is administered as a first line therapy.

In certain embodiments, provided herein is a first line therapy method of treating a hematologic proliferative disorder in a subject ineligible for intensive chemotherapy, said method comprising administering to said patient a low-intensity CPX-351 treatment wherein CPX-351 is administered intravenously at a cytarabine dose of less than 32 mg/m$^2$/day in less than 3 hours and wherein CPX-351 is administered no more than two times per week.

BRIEF DESCRIPTION OF THE DRAWINGS

FIG. 1A is schematic of a model used for PK/PD myelosuppression.

FIGS. 12A-12B and 13A-13B show the change in IC50 for the CTG-2226 and CTG-2233, cell lines respectively.

MODES OF CARRYING OUT THE INVENTION

Figure 1B:
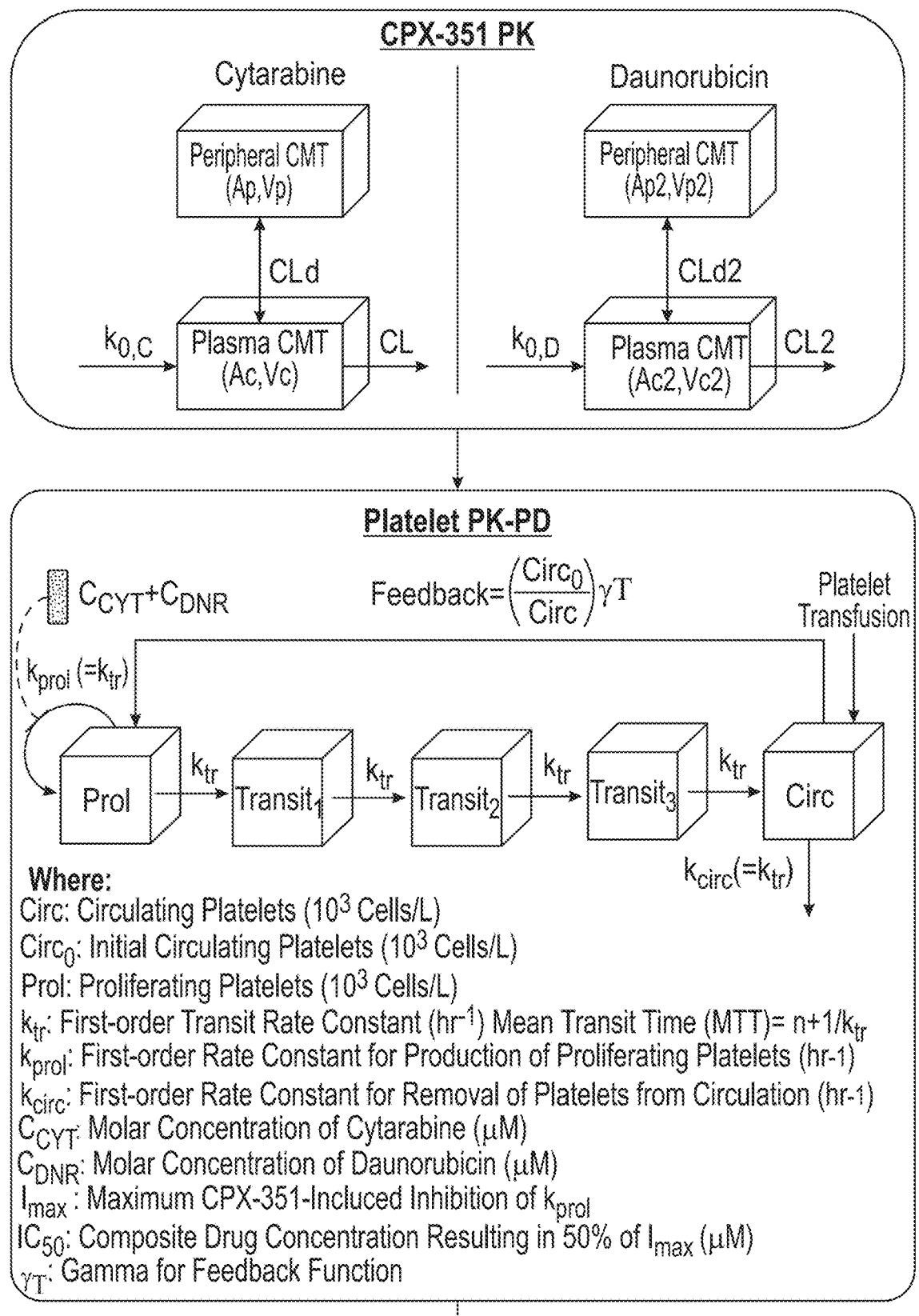
FIGS. 1B-1E show a summary of Population PK and PK-PD Models.
Figure 1C:
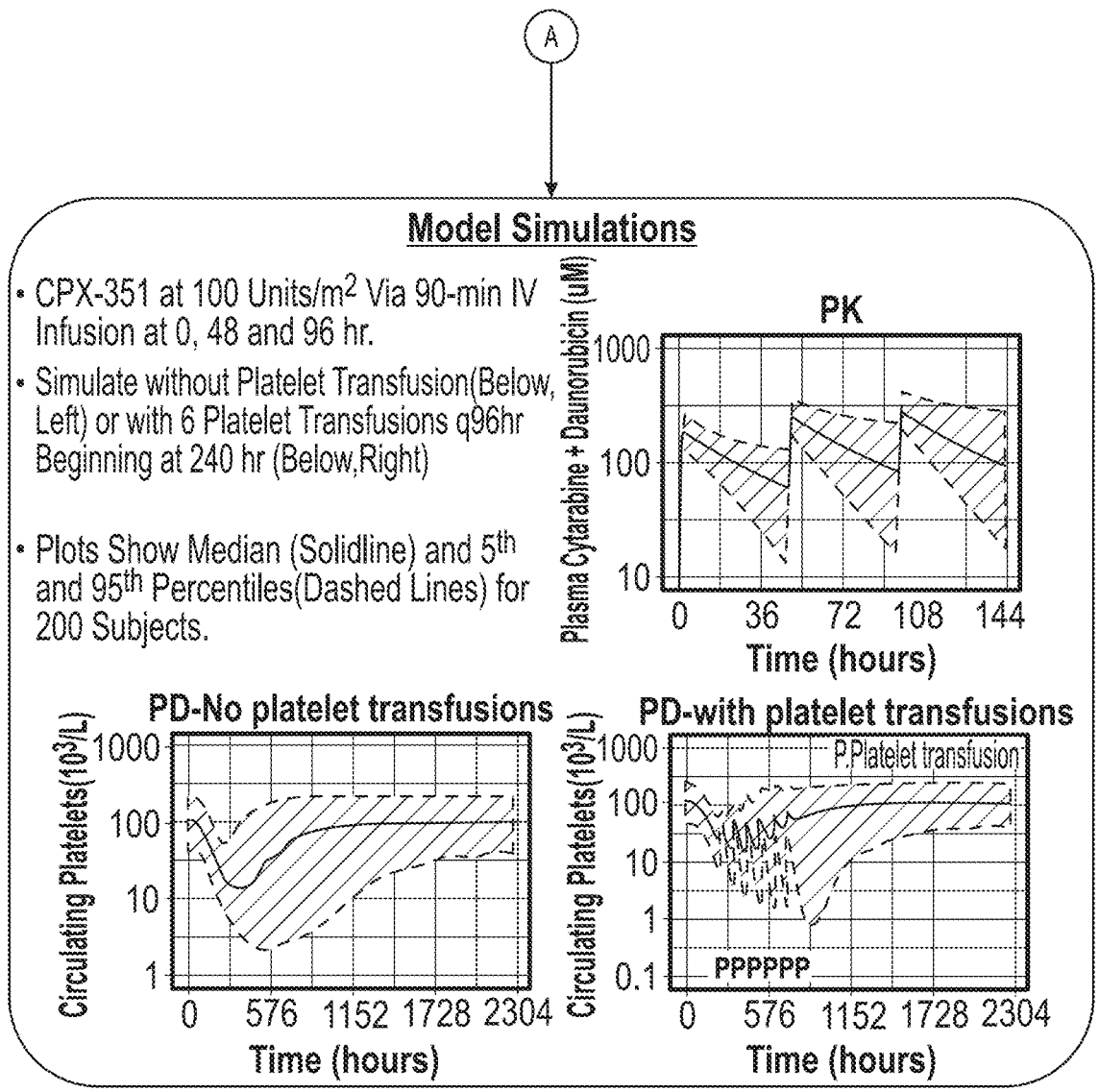

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

Definitions

As used herein, "a" or "an" means "at least one" or "one or more."

Abbreviations used herein include: PK, pharmacokinetic; PD, pharmacodynamic; CMT, compartment; Ap, peripheral amount of drug; Vp, peripheral volume of distribution; CLd, distribution clearance; $k_0$, 0-order rate constant; Ac, central amount of drug; Vc, central volume of distribution; CL, clearance; GCSF, granulocyte colony-stimulating factor; SC, subcutaneous; F, bioavailability; $k_a$, first-order absorption rate constant; D, dose; CL, clearance; $K_D$, equilibrium dissociation constant for GCSF and GCSF receptor R, accumulation ratio; $K_{int}$, first-order rate constant for internalization of GCSF receptor complexed with filgrastim or pegfilgrastim; $K_D$, dissociation constant; IV, intravenous; ANC, absolute neutrophil count.

By "low-intensity therapy", "low intensity treatment, "LIT", or "low dose treatment" or "low dose therapy", it is meant to include both a lower individual dose and/or less dosages in the dosing schedule. (For example, weekly or monthly schedule, such as an Induction treatment/therapy or Consolidation treatment/therapy) which is lower and/or less intense than a similar therapy used in cancer patients who may qualify for ICT is also included. Specifically "low dose CPX-351 treatment" may be a lower dose and/or weekly or 28-day dosing schedule that has less dosages than that used in Study 301.

The development of Vyxeos® (Jazz Pharmaceuticals) (CPX-351), cytarabine: daunorubicin liposome injection was based on 1) defining a non-antagonistic ratio of the two active moieties, cytarabine and daunorubicin, using cell-based screening assays and 2) designing a liposomal drug carrier to maintain this ratio after intravenous administration. This ratio was not based on the empirically-derived regimens currently used for cytarabine and anthracyclines.

The present invention overcomes deficiencies in the prior art by providing a low-intensity therapy (LIT) of CPX-351 that is suitable for administration to patients who are ineligible for standard intensive chemotherapy (ICT). ISICT patients are defined as either:

1) ≥75 years of age, or
2) ≥18 to 74 years of age and fulfill at least 1 criteria associated with lack of fitness for intensive induction chemotherapy as follows:

Eastern Cooperative Oncology Group (ECOG) Performance status of 2 to 3;

Cardiac history of Congestive Heart Failure (CHF) requiring treatment of Ejection Fraction≤50% or chronic stable angina Diffusing Capacity of the Lung for Carbon Monoxide (DLCO)≤65% or Forced Expiratory Volume in 1 second (FEV1)<65%;

Creatinine clearance >30 mL/min to <45 mL/min;

Moderate hepatic impairment with total bilirubin >1.5 to ≤3.0× Upper Limit of Normal (ULN); or, Other comorbidity that the physician judges to be incompatible with conventional intensive chemotherapy.

A "treatment cycle" is a specific protocol that specifies dosage times and amounts for CPX-351 and, if appropriate, an additional agent. For example, a treatment cycle may employ 2-3 administrations of CPX-351 on certain days with specified dosages, for example, on days 1 and 3, or 1 and 5, or 1 and 8, or 1 and 15, or on days 1, 2 and 5, or 1,5, and 8, or 1, 5 and 15 or 1, 8 and 15. The specific days may vary.

ISICT patients are critical populations to demonstrate benefit given the high unmet medical need. Population sizes are significant and yet the treatments available today still do not provide adequate improvements in overall survival. CPX-351 represents a promising new tool for improving efficacy while maintaining safety for these patients.

A number of factors are used to determine eligibility for ICT including, for example, physical performance, comorbid conditions and cognitive function (Pettit and Odenike; *Front. Oncol.* (2015) 5:280; which is incorporated herein by reference). The therapeutic aim for ISICT patients is to reduce disease burden, extend patient life, and improve their quality of life.

In addition, the CPX-351 LIT provides a myelosuppressive profile that allows it to be safely combined with other agents effective in treating these otherwise ineligible patients or effective in treating leukemias. These may, for example, be hypomethylation agents or BCL-2 inhibitors.

AML

Acute Myeloid Leukemia is a clonal expansion of undifferentiated myeloid precursors that causes an impairment of new blood cell generation. The median age of diagnosis 67 years. Clinical manifestations include fever, fatigue, bone pain, pallor, easy bruising. Diagnosis is based on having ≥20% myeloid blasts in the bone marrow. Disease characteristics including cytogenetic and molecular genetic findings are major prognostic factors. Patient characteristics (age, co-morbidities) also play a role in prognosis, since they influence the ability to undergo treatment. Currently, optimal disease treatment for fit patients is based on intensive chemotherapy, divided into induction and consolidation phases. Differential diagnosis includes other hematologic malignancies and MDS.

MDS

Myelodysplastic syndromes are a family of rare disorders in which the bone marrow fails to make enough healthy red blood cells, white blood cells or platelets. This is caused by bone marrow producing lots of underdeveloped, or immature, cells that have an abnormal shape, size or look. These are called blast cells. Most experts agree that MDS is a form of blood and bone marrow cancer and can be difficult to diagnose.

CPX-351 LIT Monotherapy or Combination Therapy

In a phase 3 trial in older adults (aged 60-75 years) with newly diagnosed high-risk/secondary AML, CPX-351 significantly prolonged overall survival versus standard 7+3 cytarabine/daunorubicin (9.56 vs 5.95 months; hazard ratio=0.69; 1-sided P=0.003), and the safety profile of CPX-351 was generally consistent with the known profile of the 7+3 regimen (Lancet J E, et al. J Clin Oncol. 2018; 36 (26): 2684-2692; which is incorporated herein by reference).

Chemotherapy-induced thrombocytopenia is a common and serious complication that is associated with an increased risk of bleeding and is often accompanied by chemotherapy dose adjustments, which may compromise treatment outcomes. Platelet transfusions are a mainstay for treatment of chemotherapy-induced thrombocytopenia. Chemotherapy-induced neutropenia (CIN) is a serious adverse event that is associated with an increased risk of life-threatening infection and often leads to chemotherapy dose reductions and/or treatment delays, which may lead to poor treatment outcomes. Endogenous granulocyte colony-stimulating factor (GCSF) is the primary regulator of neutrophil production, and recombinant GCSF agents are commonly used to treat CIN.

Standard dose CPX-351 as currently approved does not cover patients with AML considered ineligible for intensive chemotherapy (ICT), or some patients with MDS. The current approach to treating patients ineligible for ICT consists of lower intensity treatments (e.g. Low dose cytarabine (LDAC) or HMA alone or in various combinations with novel agents. Primary intent is to minimize toxicity while achieving acceptable response rate translating into improvement of Quality-of-Life, reduction of transfusion requirements and possibly extension of survival.

Lower intensity combinations can achieve significant response rates in vulnerable patient populations. Whereas response rates with LDAC or HMAs single agents are modest, significantly higher and more durable responses can be seen in combinations as recently demonstrated with lower intensity therapy plus Venetoclax (DiNardo et al., *Blood* (2015) 126:327; incorporated herein by reference.)

CPX-351 is biologically active in high-risk patient populations, including secondary AML with prior history of MDS and those patients with MDS related karyotype (see phase 3 study referenced herein). CPX-351 improved survival compared to the standard 7+3 therapy in patients with AML who progressed from MDS and who were previously untreated with HMA.

Focusing on AML patients with 20-29% blasts ("oligoblastic AML", in the past also referred to as "RAEBT", a subtype of advanced MDS), CPX-351 showed superior median overall survival of 12.5 months compared with 5.95 months with 7+3 including patients with prior HMA exposure. Thus there is therefore reason to believe that lower intensity CPX-351 could be a more effective backbone combination partner when compared to LDAC or HMA.

When treating AML patients not eligible for standard ICT, subjects for use with low-intensity treatment of CPX-351 should have histological confirmation of AML by World Health Organization (WHO) criteria.

In one embodiment, PK-PD modeling is used to determine a starting dose and/or dosing regimen for CPX-351 in patients considered ineligible for ICT. In one embodiment, previously developed population PK models (such as those described in Qi W, et al. *Blood*. 2017;130, Abstract 5064) are used to generate patient-specific cytarabine and daunorubicin concentration-time profiles in patients with AML, acute lymphocytic leukemia (ALL), or myelodysplastic syndrome (MDS) following CPX-351 administration.

In one embodiment, provided is a population PK-PD model of chemotherapy-induced thrombocytopenia following CPX-351 administration that incorporates the effect of concurrent platelet transfusions. In certain embodiments, patient covariates are used to describe variability in chemotherapy-induced thrombocytopenia.

In one embodiment, provided is a population PK-PD model of chemotherapy-induced neutropenia (CIN) following CPX-351 administration that incorporates the effect of concurrent GCSF therapy. In certain embodiments, patient covariates are used to describe variability in CIN.

In one embodiment, provided is an R Shiny application utilizing the population PK and PK-PD models for simulation of platelet dynamics following CPX-351 or 7+3 administration with or without intermittent platelet transfusions. In another embodiment, provided is an R Shiny application utilizing the population PK and PK-PD models for simulation of neutrophil dynamics following CPX-351 administration with or without GCSF in various dosing regimens.

The following examples are offered to illustrate but not to limit the invention.

Example 1

Population Pharmacokinetic-Pharmacodynamic (PK-PD) Modeling of 7+3 or CPX-351-Induced Thrombocytopenia The following CPX-351 studies were used for PK-PD Modeling:

Study 101

Phase 1, open-label, dose-escalation study of CPX-351 in 48 adults with relapsed/refractory AML, ALL, or MDS CPX-351 Dosages: 3 to 134 units/m$^2$ (1 unit=1 mg of cytarabine and 0.44 mg of daunorubicin) via 90-minute intravenous (IV) infusion on Days 1, 3, and 5.

PK Data Collection: Intensive sampling on Days 1, 3, and 5.

PD Data Collection: Pre-dose; on Days 1, 2, 3, 4, 5, 7, 14, 21, 28, 35, 42, and 56; and at follow-up (30 days after study discontinuation)

Study 206
  Phase 2, open-label study of CPX-351 in 26 adults with AML, ALL, or MDS.
  CPX-351 dosages
    Induction: 100 units/m² (100 mg/m² cytarabine+44 mg/m² daunorubicin) via 90-minute IV infusion on Days 1, 3, and 5 (2nd induction: Days 1 and 3)
    Consolidation: 65 units/m² (65 mg/m² cytarabine+29 mg/m² daunorubicin) via 90-minute IV infusion on Days 1 and 3.
  PK Data Collection: Intensive sampling on Days 1 and 5.
  PD Data Collection: Pre-dose; on Days 1, 3, 5, 7, 10±2, and 14±2; and then weekly (±2 days) until whichever occurred last: (1) Day 42, (2) peripheral blood count recovery, or (3) removal from study Study 301
  Phase 3, multicenter, randomized trial in older adults with newly diagnosed high-risk/secondary AML to assess CPX-351 (n=153) versus 7+3 (n=156).
  CPX-351 Dosages: Same as for Study 206
  PK Data Collection: Sparse sampling throughout first week
  PD Data Collection: Same as for Study 206

Table 1 shows the population PK parameters for Cytarabine and Daunorubicin following CPX-351 administration.

TABLE 1

Initial Population PK Parameters for Cytarabine and Daunorubicin Following CPX-351 Administration

| Parameter | Population mean equation | Interindividual variability |
|---|---|---|
| *Cytarabine* | | |
| CL, L/h | $0.106 \cdot (BSA/1.95)^{1.03}$ | 0.404 (63.5% CV) |
| Vc, L | $5.12 \cdot (BSA/1.95)^{1.16} \cdot (DOSEMGC/195)^{0.111}$ | 0.0847 (29.1% CV) |
| CLd, L/h | $0.00646 \cdot (BSA/1.95)^{1}$ | 0.5 Fixed (70.7% CV) |
| Vp, L | $0.214 \cdot (BSA/1.95)^{1}$ | 0.5 Fixed (70.7% CV) |
| Residual variability | 0.151 (log error) | — |
| *Daunorubicin* | | |
| CL2, L/h | $0.145 \cdot (BSA/1.95)^{1.22} \cdot \exp(-0.176 \cdot FORM2)$ | 0.218 (46.7% CV) |
| Vc2, L | $4.34 \cdot (BSA/1.95)^{1.27} \cdot \exp(-0.216 \cdot FORM2)$ | 0.0564 (23.7% CV) |
| CLd2, L/h | $0.0258 \cdot (BSA/1.95)^{1}$ | 0.5 Fixed (70.7% CV) |
| Vp2, L | $0.523 \cdot (BSA/1.95)^{1} \cdot (DOSEMGD/86)^{0.701}$ | 0.5 Fixed (70.7% CV) |
| Residual variability | 0.154 (log error) | — |

PK, pharmacokinetic; CL, clearance; BSA, body surface area; CV, coefficient of variation; Vc, central volume of distribution; DOSEMGC, cytarabine dose in mg; CLd, distribution clearance; Vp, peripheral volume of distribution; FORM2, CPX-351 formulation (1 for frozen, 0 for lyophilized); DOSEMGD, daunorubicin dose in mg.

Population PK-PD analysis was conducted using NON-MEM version 7.3 via implementation of the first-order conditional estimation method with η-ε interaction. Previously developed population PK models for CPX-351 and non-liposomal cytarabine and daunorubicin were used to generate patient-specific cytarabine and daunorubicin concentration-time profiles (Qi W, et al. *Blood*. 2017;130. Abstract 5064 incorporated herein by reference). For both cytarabine and daunorubicin, 2-compartment disposition models were used to describe drug PK following CPX-351 administration. In the population PK-PD model of chemotherapy-induced thrombocytopenia, data from Cycle 1 were excluded if patients had a platelet count <50×10⁹/L prior to the first treatment cycle; data from subsequent cycles were only included if the platelet count returned to >50×10⁹/L prior to treatment.

Platelet count versus time data were described by a modified maturation PK-PD model proposed by Friberg et al (Friberg L E, et al. *J Clin Oncol.* 2002;20 (24): 4713-4721; incorporated herein by reference). Inhibition of platelet proliferation by CPX-351 and/or "7+3" was driven by a sigmoidal maximum inhibition (Imax) function of the sum of the molar concentrations of cytarabine and daunorubicin. Interindividual and interoccasion variability were estimated for select structural PK-PD model parameters using exponential error models.

The effect of each platelet transfusion on platelet dynamics was incorporated as a bolus input of 35×10⁹/L into the circulating platelet pool, as this was the expected rise in platelet counts immediately post-transfusion (Mccullough J. *Semin Hematol.* 2010; 47 (3): 235-242; incorporated herein by reference) (see FIGS. 1A-1G). Information regarding actual platelet dose administered was not standardized or always provided, so the typical value for platelet transfusion bioavailability was fixed at 1 and interindividual variability in platelet transfusion bioavailability was estimated to allow for interindividual variability in the expected increase in platelet count following a platelet transfusion.

A graphical screening procedure was conducted to examine the relationship between patient covariates and key PK-PD model parameters, followed by stepwise forward selection (α=0.01) and backward elimination (α=0.001) to evaluate covariate effects. Baseline Patient Demographics were: Weight, height, age, body mass index, body surface area, sex, race, and ethnicity. Baseline Clinical Laboratory Measures were: Albumin, alkaline phosphatase, alanine aminotransferase, aspartate aminotransferase, total bilirubin, white blood cell count, absolute neutrophil count, platelet count, and creatinine clearance. Disease-related Indices were: Cancer type and Eastern Cooperative Oncology Group performance status.

An R Shiny application was developed in conjunction with the mrgsolve package (Metrum Research Group) so that the population PK-PD model could be used to simulate neutrophil or platelet dynamics following administration of various CPX-351 and "7+3" dosing regimens (including as administered in Study 301) with or without intermittent platelet transfusions. Simulations were conducted in 200 patients with characteristics similar to the trial population to evaluate the temporal events of myelosuppression in the absence of platelet transfusion or GCSF administration (see below).

Relevant patient demographics were generated with distributions that were comparable to those in the analysis dataset. Results are shown in Table 2 below.

TABLE 2

| | Platelet model | | Neutrophil model | |
|---|---|---|---|---|
| Variable | CPX-351 (n = 137) | 7 + 3 (n = 85) | CPX-351 (n = 129) | 7 + 3 (n = 79) |
| Age, y | | | | |
| Mean (SD) | 66.1 (8.88) | 67.8 (4.27) | 66.1 (9.1) | 67.5 (4.26) |
| Median (range) | 68 (23-80) | 68 (60-75) | 67 (23-81) | 68 (60-75) |
| Weight, kg | | | | |
| Mean (SD) | 82.4 (18.6) | 82.8 (16.8) | 82.4 (20.4) | 83.8 (16.8) |
| Median (range) | 82 (42-156) | 83 (50-136) | 78.7 (39.5-156) | 83 (54-136) |
| Height, cm | | | | |
| Mean (SD) | 170 (10.3) | 169 (9.84) | 170 (10.7) | 170 (8.84) |
| Median (range) | 170 (149-198) | 168 (152-189) | 170 (149-198) | 170 (152-186) |
| BSA, m$^2$ | | | | |
| Mean (SD) | 1.97 (0.262) | 1.97 (0.235) | 1.96 (0.28) | 1.98 (0.226) |
| Median (range) | 1.95 (1.3-2.8) | 1.96 (1.49-2.55) | 1.94 (1.30-2.80) | 1.96 (1.56-2.55) |
| BMI, kg/m$^2$ | | | | |
| Mean (SD) | 28.2 (5.04) | 28.8 (5.13) | 28.2 (5.48) | 28.8 (5.17) |
| Median (range) | 27.2 (18.4-48.3) | 28.7 (19.5-45.4) | 27.4 (17.1-48.3) | 28.3 (20.2-45.4) |
| CLcr, mL/min/1.73 m$^2$ | | | | |
| Mean (SD) | 78.9 (26.8) | 77.5 (22.7) | 78.5 (27.7) | 74.3 (22.7) |
| Median (range) | 74.2 (34.1-176) | 78.1 (30.1-157) | 73.4 (36.1-176) | 73.5 (30.1-163) |
| Total bilirubin, mg/dL | | | | |
| Mean (SD) | 0.64 (0.371) | 0.644 (0.400) | 0.694 (0.468) | 0.664 (0.462) |
| Median (range) | 0.53 (0.12-2.11) | 0.53 (0.18-2.81) | 0.53 (0.12-2.92) | 0.53 (0.12-2.98) |
| ALT, U/L | | | | |
| Mean (SD) | 31.0 (27.3) | 29.5 (21.3) | 28.0 (20.2) | 32.2 (23.5) |
| Median (range) | 21 (9-154) | 23 (9-154) | 23 (5-154) | 24 (9-154) |
| AST, U/L | | | | |
| Mean (SD) | 24.9 (12.7) | 25.8 (15.2) | 26.4 (12.9) | 27.9 (15.8) |
| Median (range) | 22 (5-81) | 20 (9-96) | 24 (5-81) | 23 (11-83) |
| ALP, U/L | | | | |
| Mean (SD) | 75.5 (31.8) | 75.9 (34.4) | 87.6 (47.1) | 82.9 (50.4) |
| Median (range) | 68 (21-212) | 68 (32-202) | 77 (32-348) | 69 (32-398) |
| Albumin, g/dL | | | | |
| Mean (SD) | 3.57 (0.546) | 3.48 (0.592) | 3.50 (0.584) | 3.40 (0.584) |
| Median (range) | 3.6 (1.3-4.8) | 3.5 (1.8-4.5) | 3.6 (1.3-4.6) | 3.4 (2.0-4.5) |
| Platelet count, 10$^9$/L | | | | |
| Mean (SD) | 85.1 (66.7) | 101 (107) | 67.1 (61.0) | 72.1 (124) |
| Median (range) | 63 (2-289) | 77 (11-836) | 43 (2-289) | 37 (5-836) |
| WBC, 10$^9$/L | | | | |
| Mean (SD) | 12.8 (32.1) | 9.61 (15.5) | 18.5 (35.3) | 18.5 (26.5) |
| Median (range) | 3.4 (0.24-323) | 2.9 (0.48-76.7) | 6.6 (0.9-323) | 7.1 (0.5-170) |
| ANC, 10$^9$/L | | | | |
| Mean (SD) | 2.56 (5.19) | 2.02 (3.61) | 4.42 (7.57) | 4.59 (9.87) |
| Median (range) | 0.76 (0-40.1) | 0.585 (0.03-24.2) | 1.98 (0-9.4) | 2.20 (0.06-83.1) |

PK, pharmacokinetic; PD, pharmacodynamic; SD, standard deviation; BSA, body surface area; BMI, body mass index; CLcr, creatinine clearance; ALT, alanine transaminase; AST, aspartate transaminase; ALP, alkaline phosphatase; WBC, white blood cell count; ANC, absolute neutrophil count.

TABLE 2A

Demographic and Disease Status

| Category | Variable | Platelet model CPX-351 n (%) | Platelet model 7 + 3 n (%) | Neutrophil model CPX-351 n (%) | Neutrophil model 7 + 3 n (%) |
|---|---|---|---|---|---|
| Received ≥1 platelet transfusion/ GCSF | No | 2 (1.5) | 2 (2.4) | 86 (66.7) | 46 (58.2) |
| | Yes | 135 (98.5) | 83 (97.6) | 43 (33.3) | 33 (41.8) |
| Sex | Male | 82 (59.9) | 49 (57.6) | 79 (61.2) | 48 (60.8) |
| | Female | 55 (40.1) | 36 (42.4) | 50 (38.8) | 31 (39.2) |
| Race | Caucasian | 115 (83.9) | 74 (87.1) | 110 (85.3) | 70 (88.6) |
| | Black | 8 (5.8) | 4 (4.7) | 6 (4.7) | 5 (6.3) |
| | Asian | 8 (5.8) | 2 (2.4) | 4 (3.1) | 1 (1.3) |
| | Other/missing | 6 (4.4) | 5 (5.9) | 9 (7.0) | 3 (3.8) |
| ECOG performance status | 0 | 47 (34.3) | 29 (34.1) | 39 (30.2) | 23 (29.1) |
| | 1 | 78 (56.9) | 45 (52.9) | 76 (58.9) | 44 (55.7) |
| | 2 | 12 (8.8) | 11 (12.9) | 14 (10.9) | 12 (15.2) |
| Cancer type | ALL | 3 (2.2) | 0 (0) | 3 (2.33) | 0 (0) |
| | AML | 133 (97.1) | 85 (100) | 126 (97.7) | 79 (100) |
| | MDS | 1 (0.7) | 0 (0) | 0 (0) | 0 (0) |
| Remission status | CR | 62 (45.3) | 37 (43.5) | 56 (43.4) | 28 (35.4) |
| | CRi | 16 (11.7) | 6 (7.1) | 11 (8.5) | 4 (5.1) |
| | None | 59 (43.1) | 42 (49.4) | 62 (48.1) | 47 (59.5) |

GCSF, granulocyte colony stimulating factor; ECOG, Eastern Cooperative Oncology Group; ALL, acute lymphocytic leukemia; AML, acute myeloid leukemia; MDS, myelodysplastic syndrome; CR, complete remission; CRi, complete remission with incomplete neutrophil or platelet recovery. NB: for patients who were thrombocytopenic (platelet count <50 × 109/L) prior to the first treatment cycle, data from Cycle 1 were excluded from analysis, and data from subsequent cycles were only included if the platelet count returned to ≥50 × 109/L prior to treatment. However, for the purposes of covariate evaluation, the baseline platelet count from Cycle 1 was used, even if the value was <50 × 109/L.

The early analysis dataset consisted of 2,023 platelet counts from 137 patients. Most patients (n=135; 98.5%) received ≥1 platelet transfusion during the study. The mean (standard deviation) number of platelet transfusions per person was 12 (9). The model fit improved significantly (P<0.00001) when bolus inputs to circulating platelets were incorporated to account for platelet transfusions. No potential covariates met criteria for inclusion.

TABLE 3

Model Fitted PD Parameters for Platelets

| Parameter | CPX-351 Estimate | CPX-351 % SEM | 7 + 3 Estimate | 7 + 3 % SEM |
|---|---|---|---|---|
| Circ0, $10^9$/L | 98.1 | 4.68 | 98.1 | 6.28 |
| MTT, h | 91.2 | 0.72 | 120 | 3.05 |
| $I_{max}$ | 0.316 | 0.29 | 1 | Fixed |
| $IC_{50}$ at weight of 83.4 kg, μM | 0.324 | 50.9 | 0.0982 | 5.6 |
| $IC_{50}$-weight power | — | — | 0.641 | 40.7 |
| γ | 1.29 | 3.96 | 3.68 | 4.24 |
| $γ^T$ | 0.178 | 1.34 | 0.153 | 7.12 |

PD, pharmacodynamic; SEM, standard error of the mean; Circ0, baseline circulating platelet count; MTT, mean transit time (4/$k_{tr}$); $I_{max}$, maximum inhibition of platelet proliferation; IC50, composite concentration (cytarabine + daunorubicin) at which inhibition is 50% of $I_{max}$; γ, Hill coefficient for sigmoidal $I_{max}$ function; γτ, feedback function exponent.

The model successfully captured observed data for CPX-351 and 7+3, with good precision on parameter estimates. In fact, most parameters in the final PK-PD model were estimated with excellent precision (<35% standard error of the mean [SEM]).

No covariates affecting the PD parameters of CPX-351 were identified, but body weight was identified as a covariate affecting the IC50 of 7+3. The population mean for baseline circulating platelet numbers (Circ0) was similar for CPX-351 and 7+3, while the population mean for mean transit time (MTT) was slightly shorter for CPX-351. 7+3 was more potent than CPX-351, albeit the plasma concentrations of cytarabine and daunorubicin with CPX-351 were far greater than with 7+3.

The median time to observe the first platelet count <0.5× $10^9$/L was 6.4 days after CPX-351 treatment and 5.8 days after 7+3, while the median time to an observed platelet count <20×$10^9$/L was 10.8 days and 8.9 days, respectively. The median duration with platelet counts <20×$10^9$/L was longer with CPX-351 (18 days) versus 7+3 (8 days), and the median duration of platelet counts platelet count <50×$10^9$/L was 22 days and 15 days, respectively. These results are summarized in Table 3A below.

TABLE 3A

Model-simulated Platelet Parameters After CPX-351 or 7 + 3 Treatment

| | CPX-351 | 7 + 3 |
|---|---|---|
| Mean (SD) nadir, $10^9$/L | 15.1 (13.5) | 9.05 (10.3) |
| Median nadir, $10^9$/L | 11.3 | 4.7 |
| Median time to nadir, h | 350 | 326 |
| Median time to 50 × $10^9$/L, h | 154 | 139 |
| Median duration <50 × $10^9$/L, h | 533 | 356 |
| Median time to 20 × $10^9$/L, h | 258 | 213 |
| Median duration <20 × $10^9$/L, h | 426 | 203 |

Figure 2A:
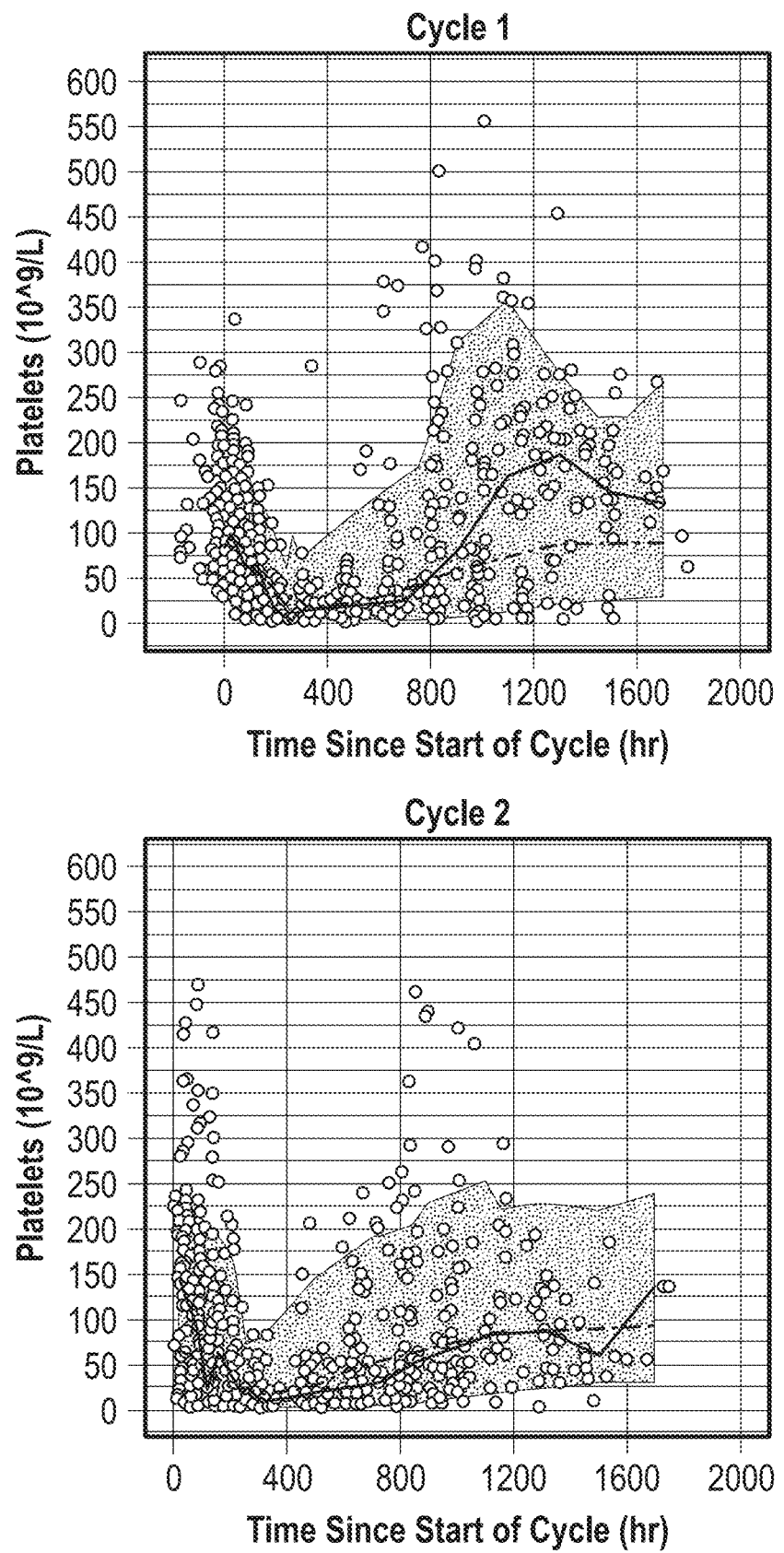
FIGS. 2A-2C show the Visual Predictive Check Stratified by Treatment Cycle for the Final Population PK-PD Model
Figure 2B:
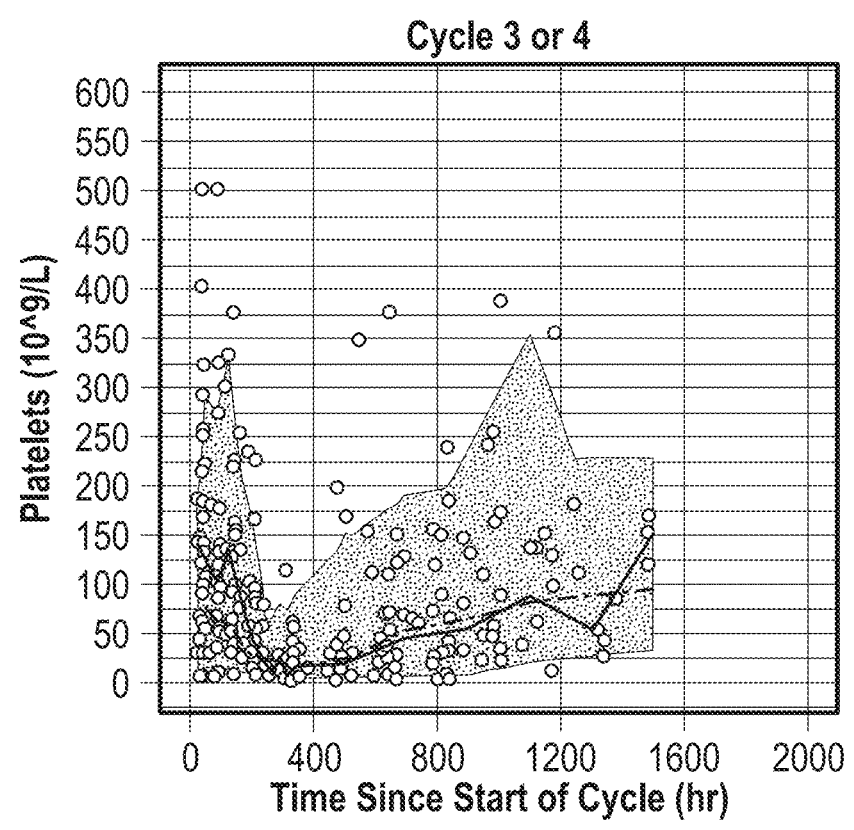
Figure 2C:
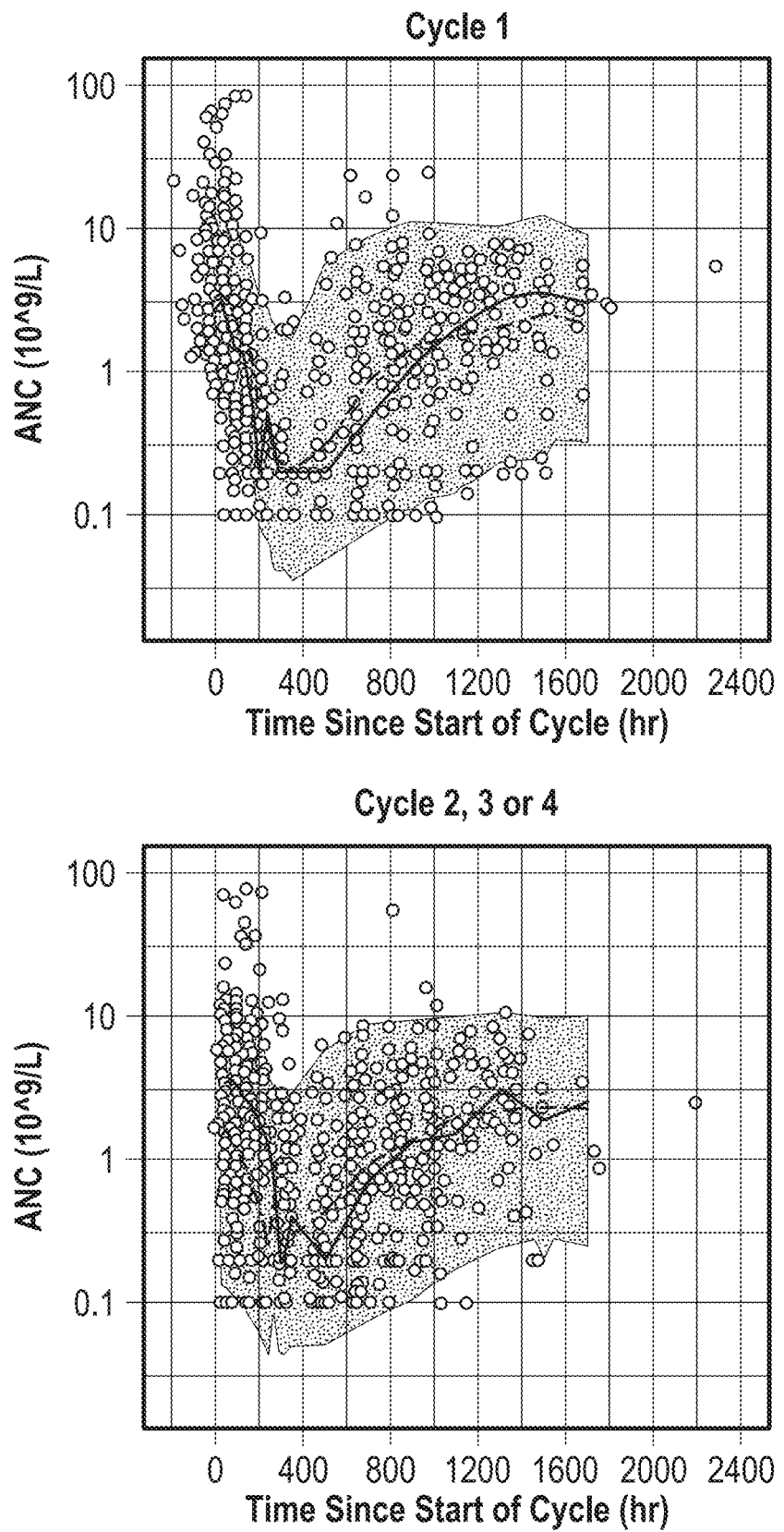
Figure 3A:
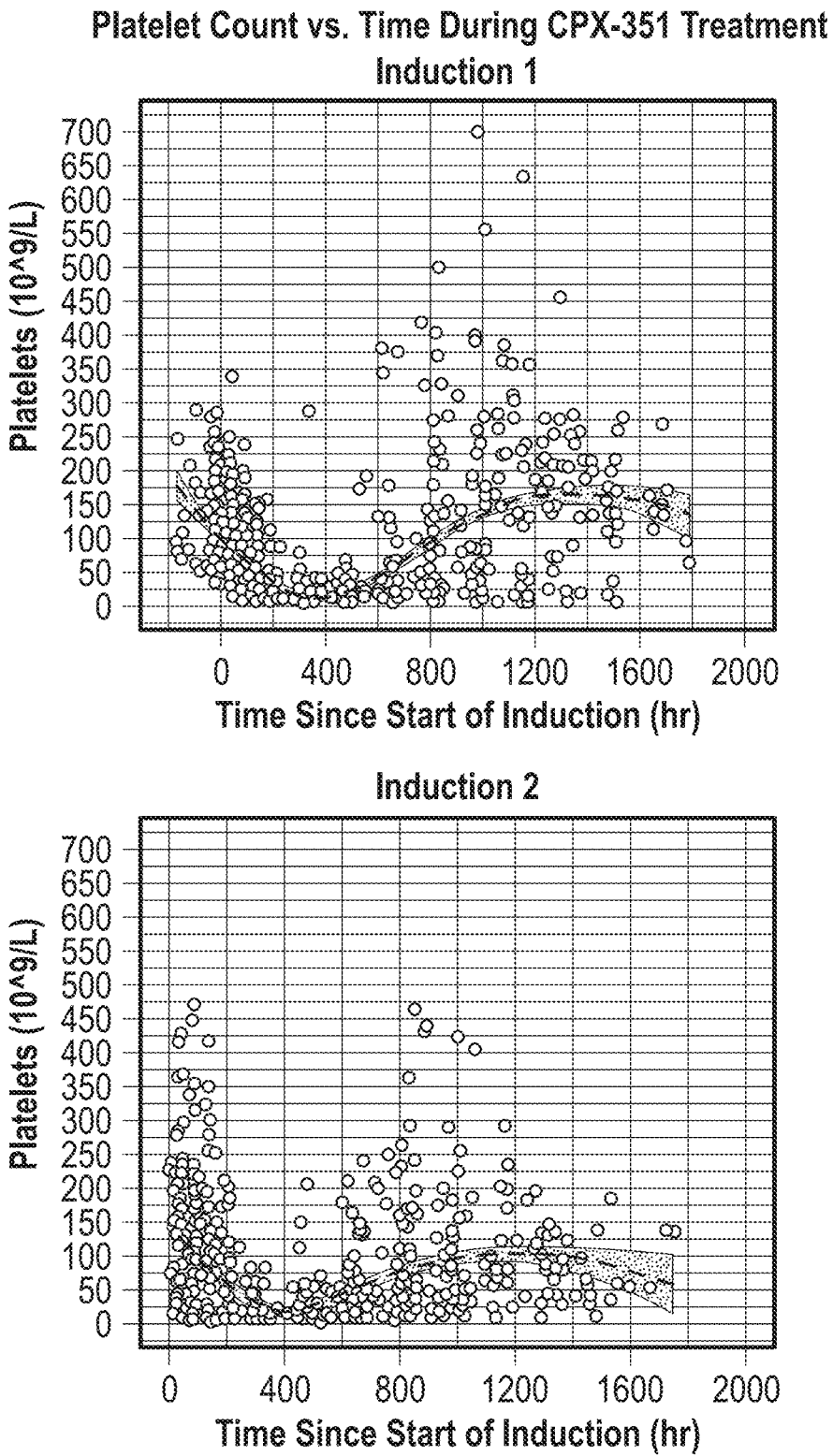
FIGS. 3A-3B shows Platelet Count vs. Time During CPX-351 Treatment
Figure 3B:
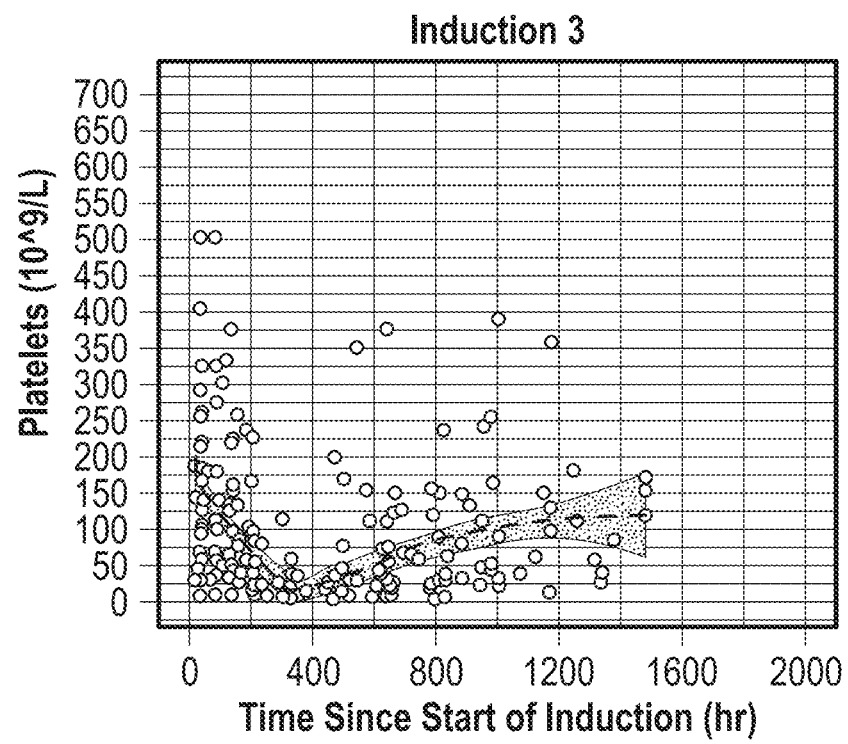
Figure 3B:
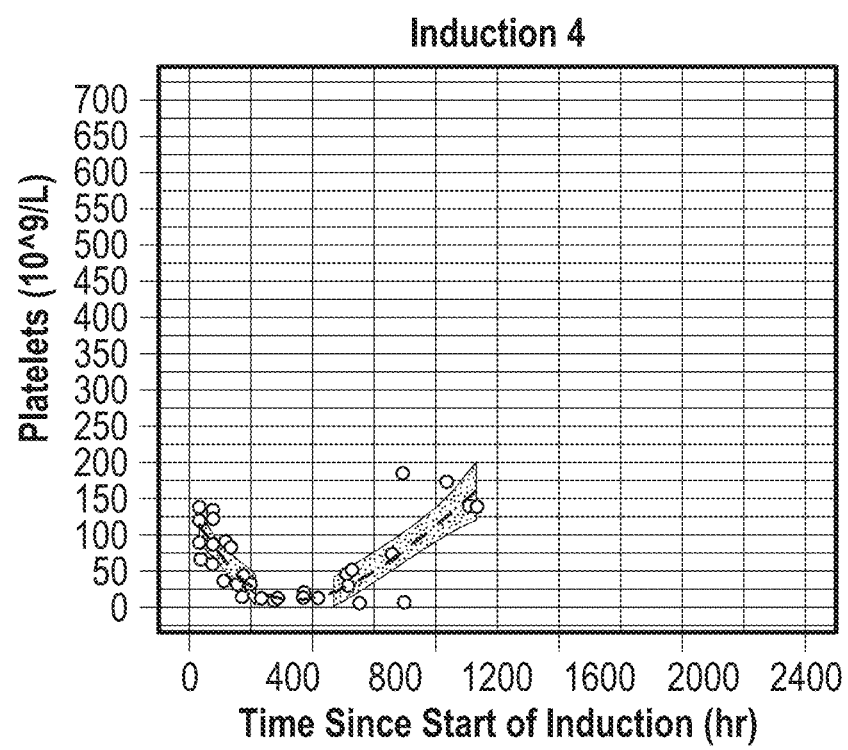
Figure 3C:
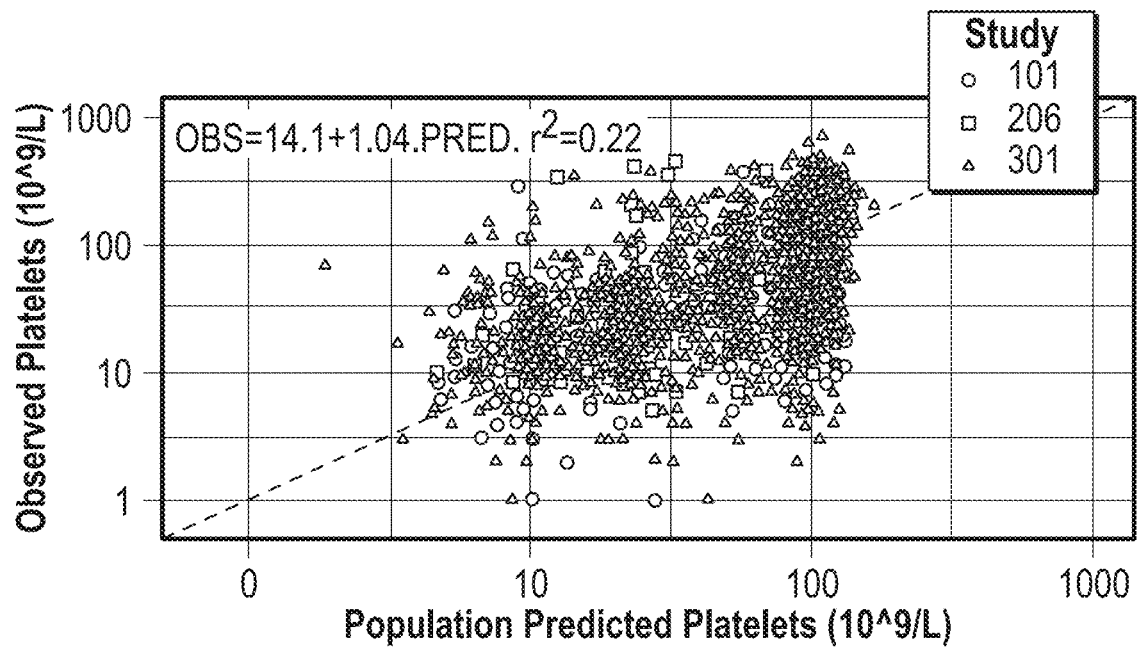
FIGS. 3C-3H show the GOF (goodness-of-fit) Plots: Final CPX-351 PK-PD Model for Platelets
Figure 3C:
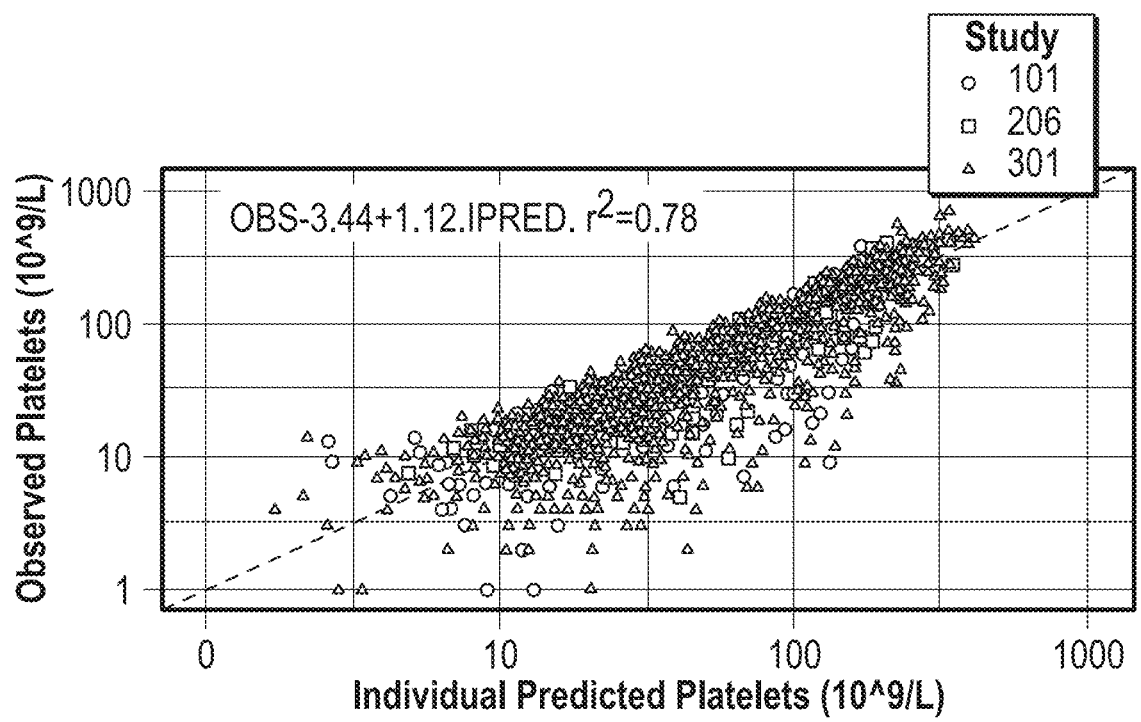
Figure 3D:
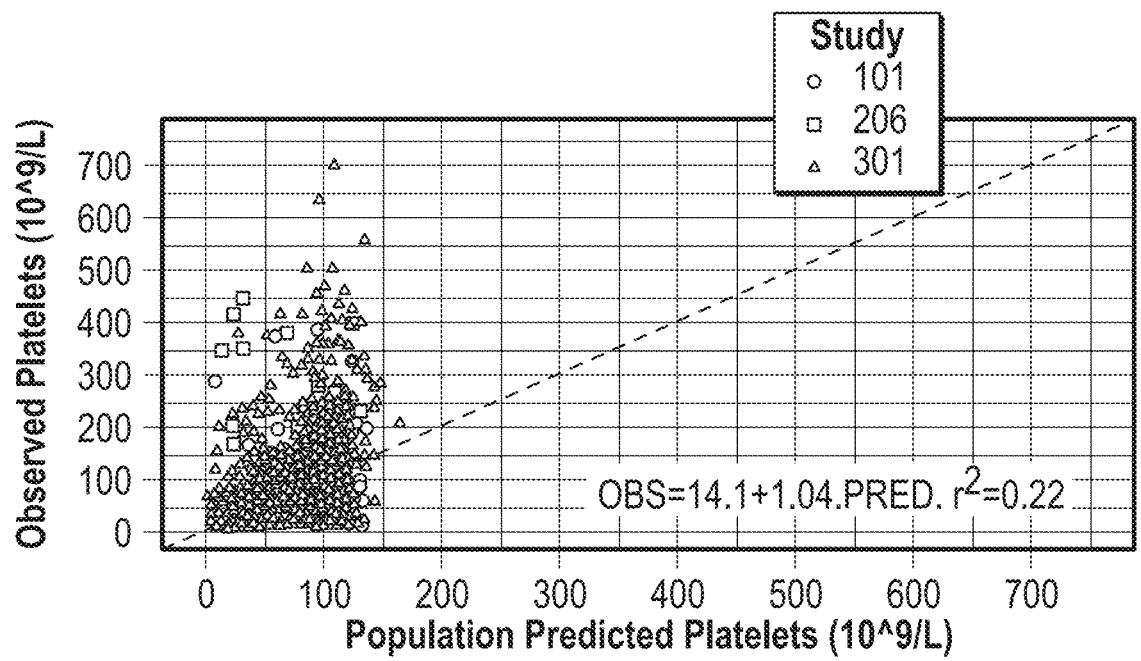
Figure 3D:
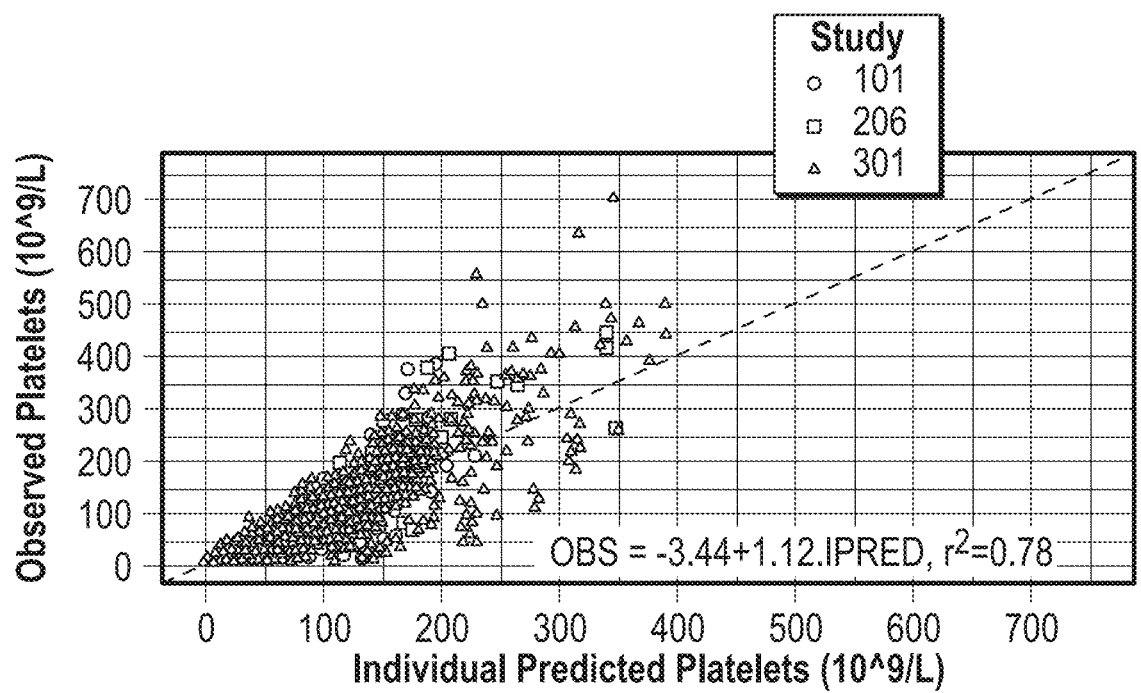
Figure 3E:
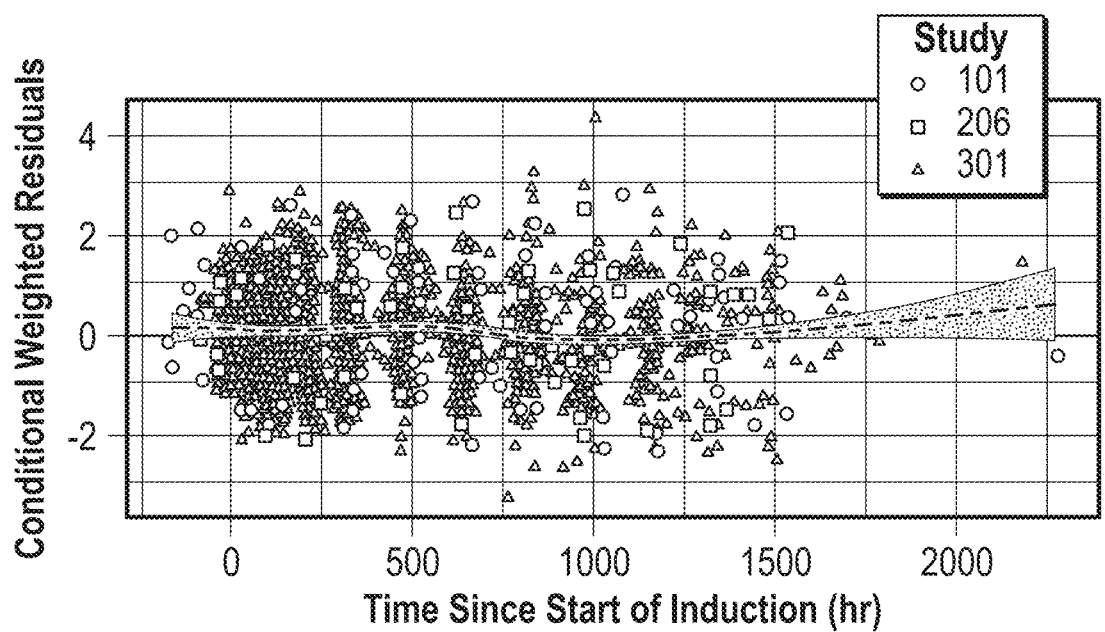
Figure 3E:
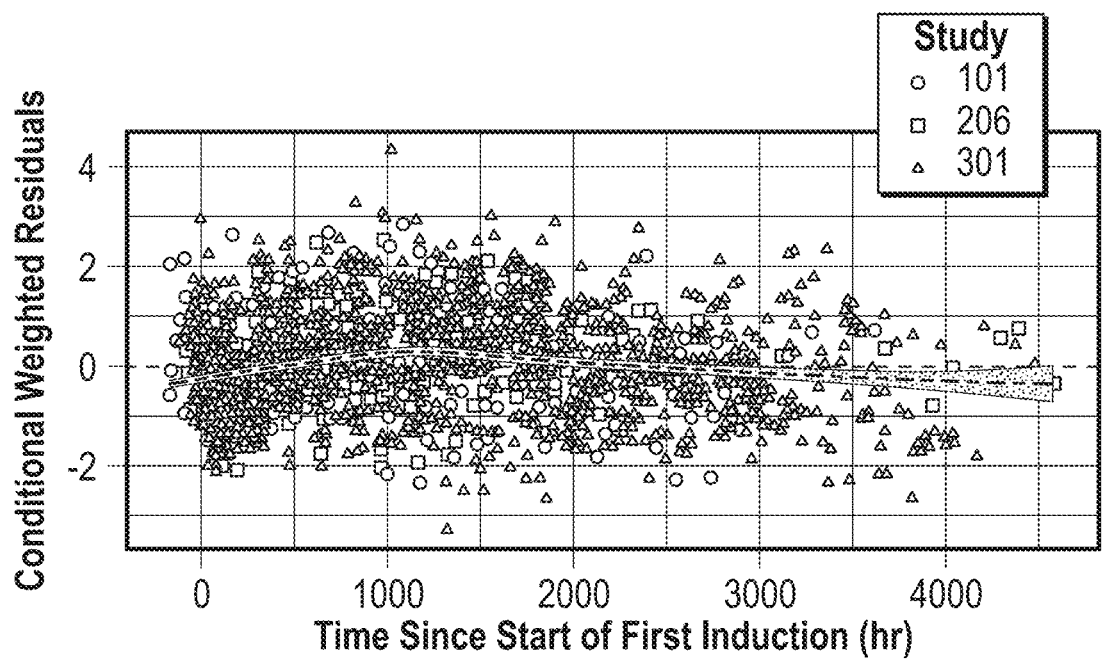
Figure 3F:
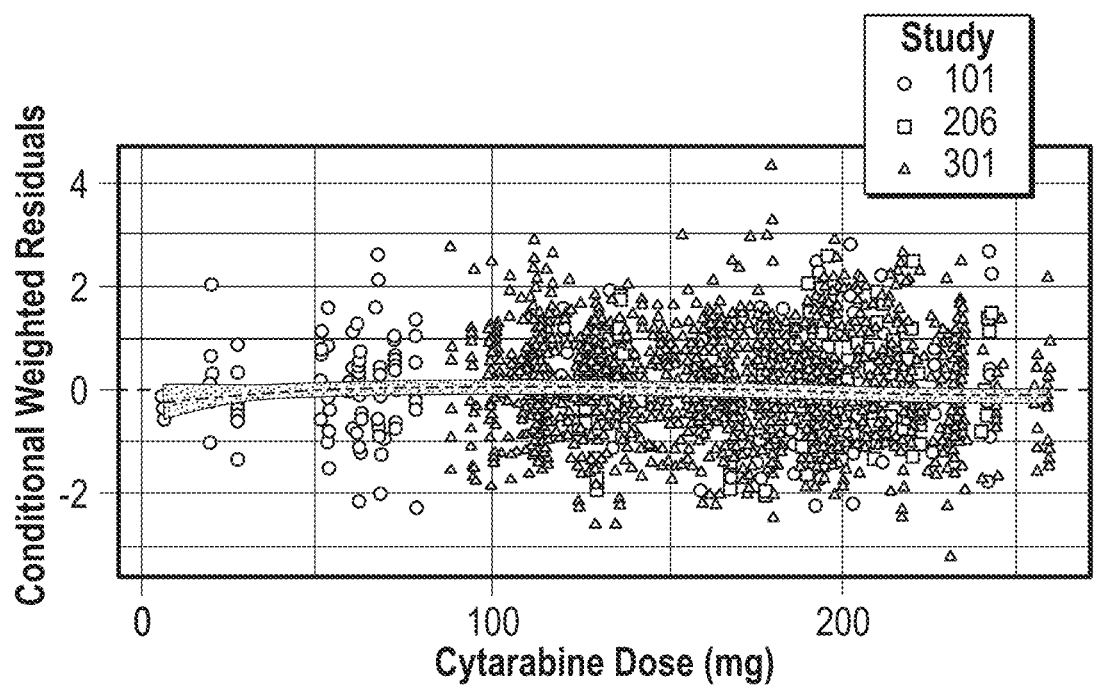
Figure 3F:
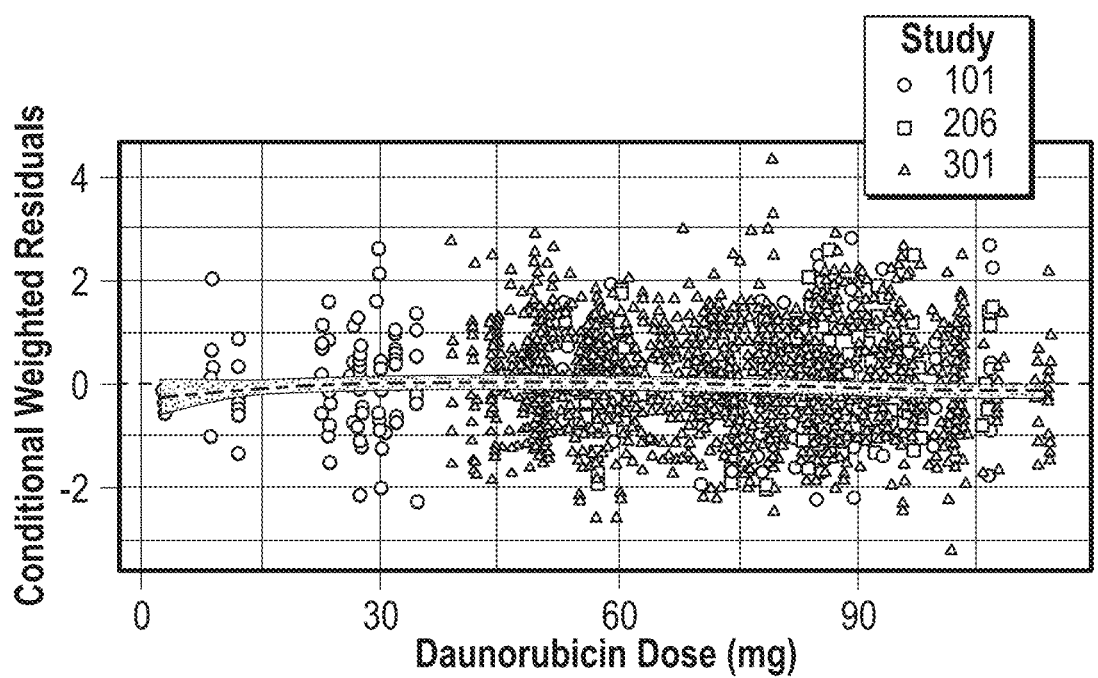
Figure 3G:
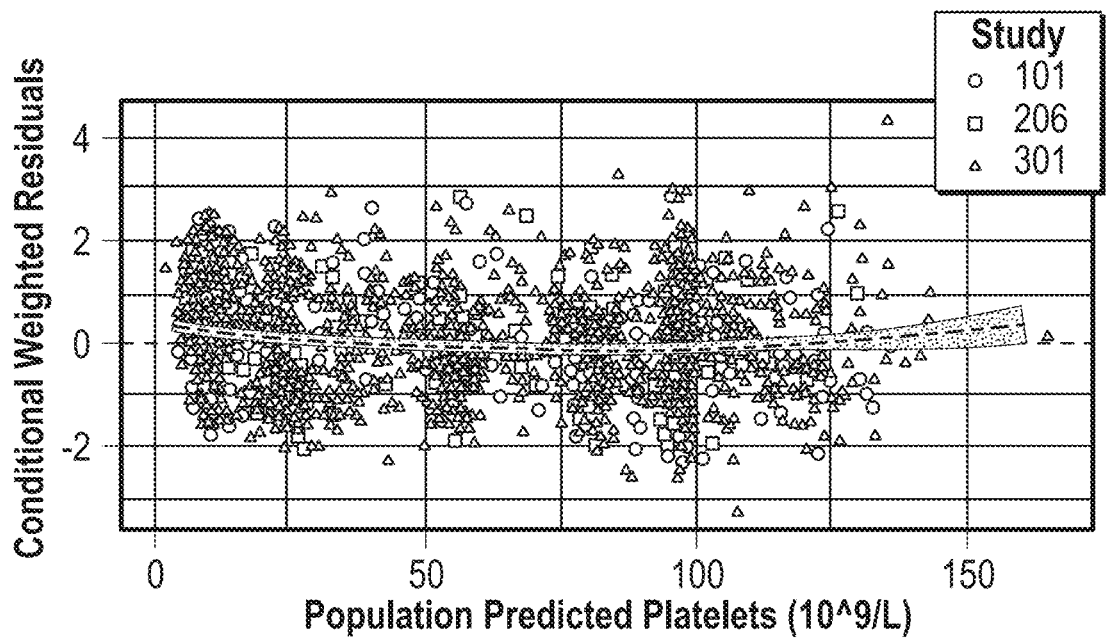
Figure 3G:
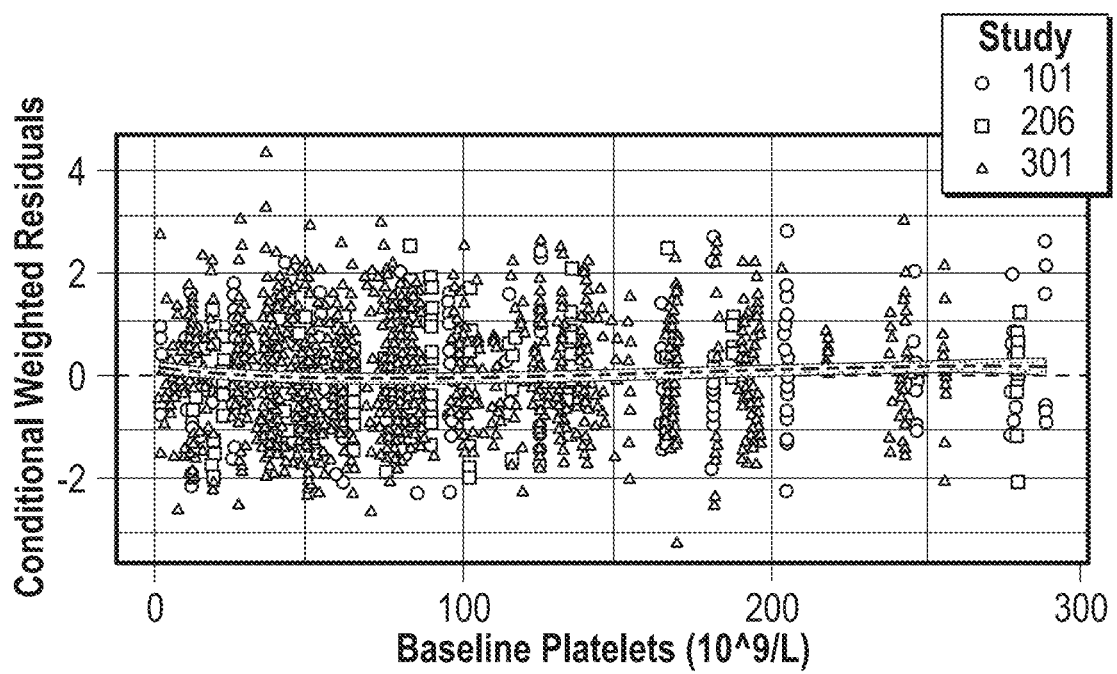
Figure 3H:
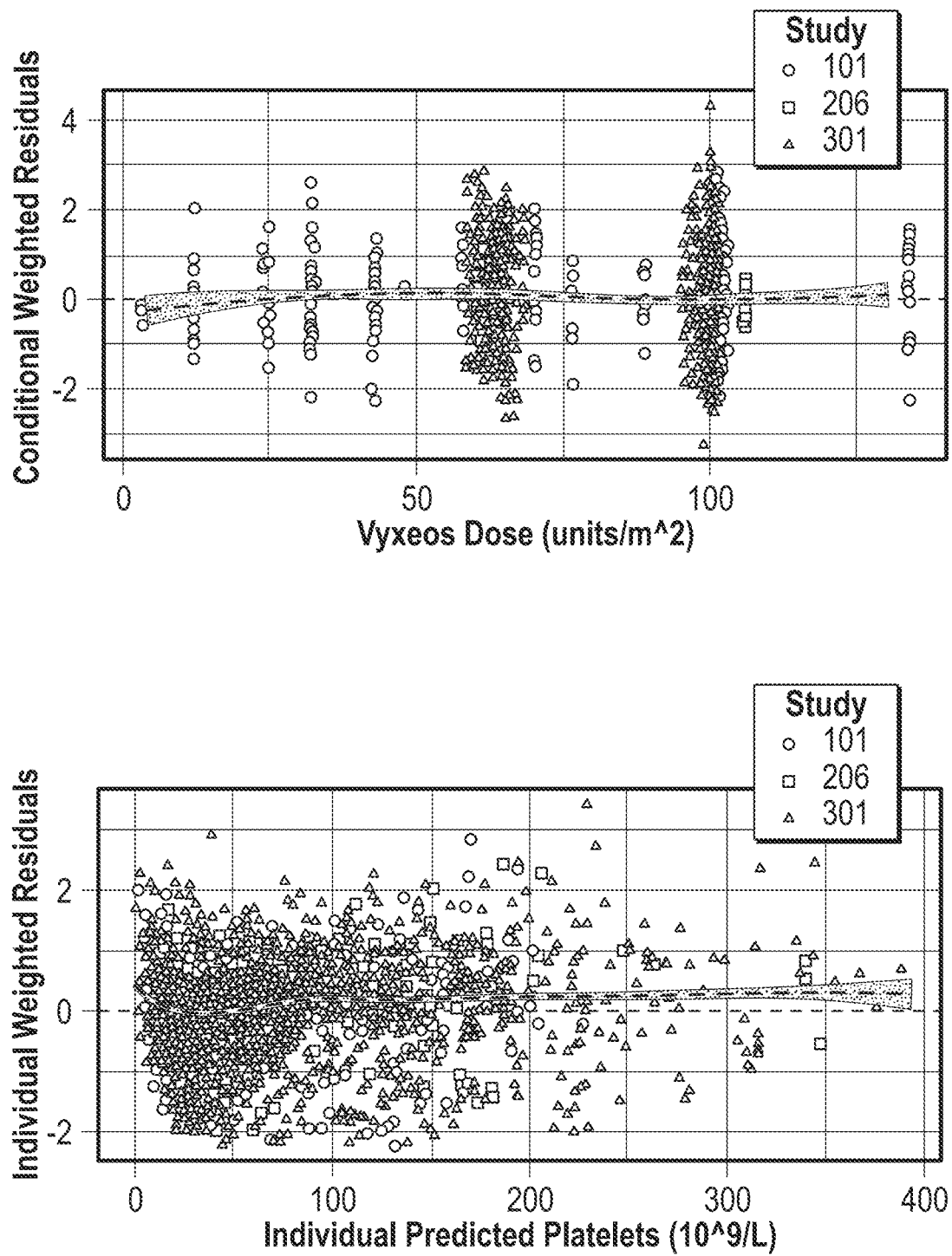
Figure 4A:
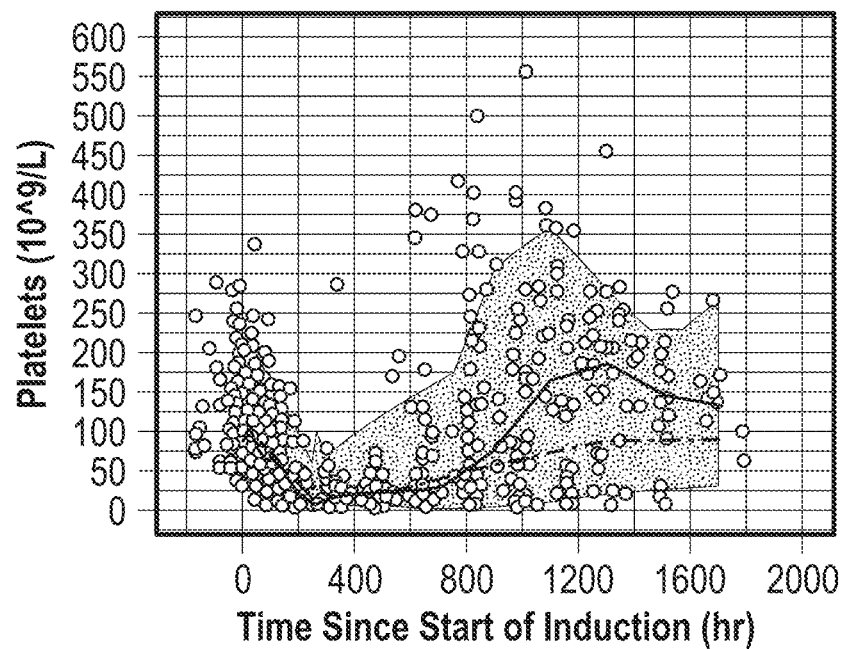
FIGS. 4A-4B show the VPC (Visual Predictive Check): Final CPX-351 PK-PD Model for Platelets
Figure 4A:
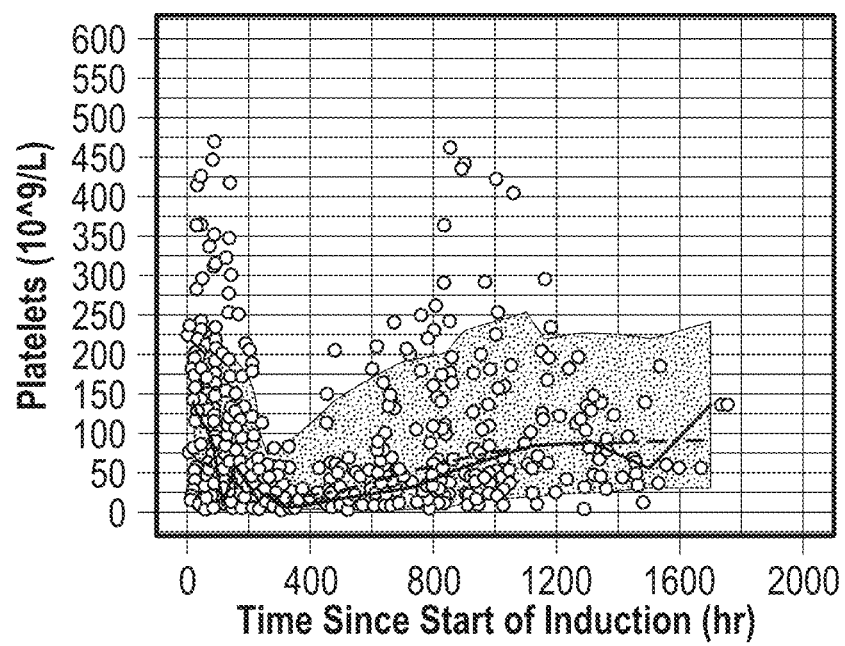
Figure 4B:
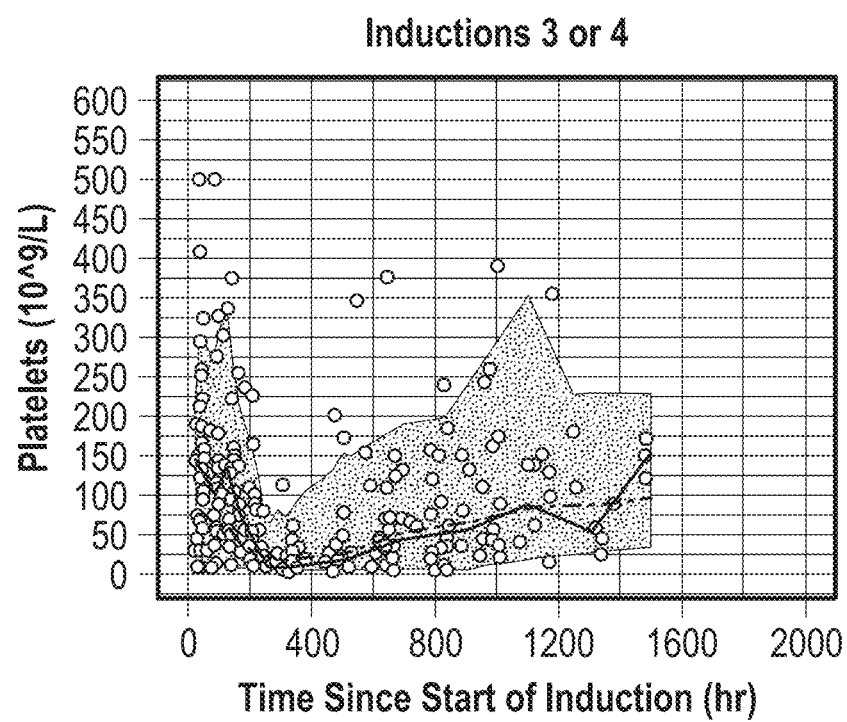
Figure 5A:
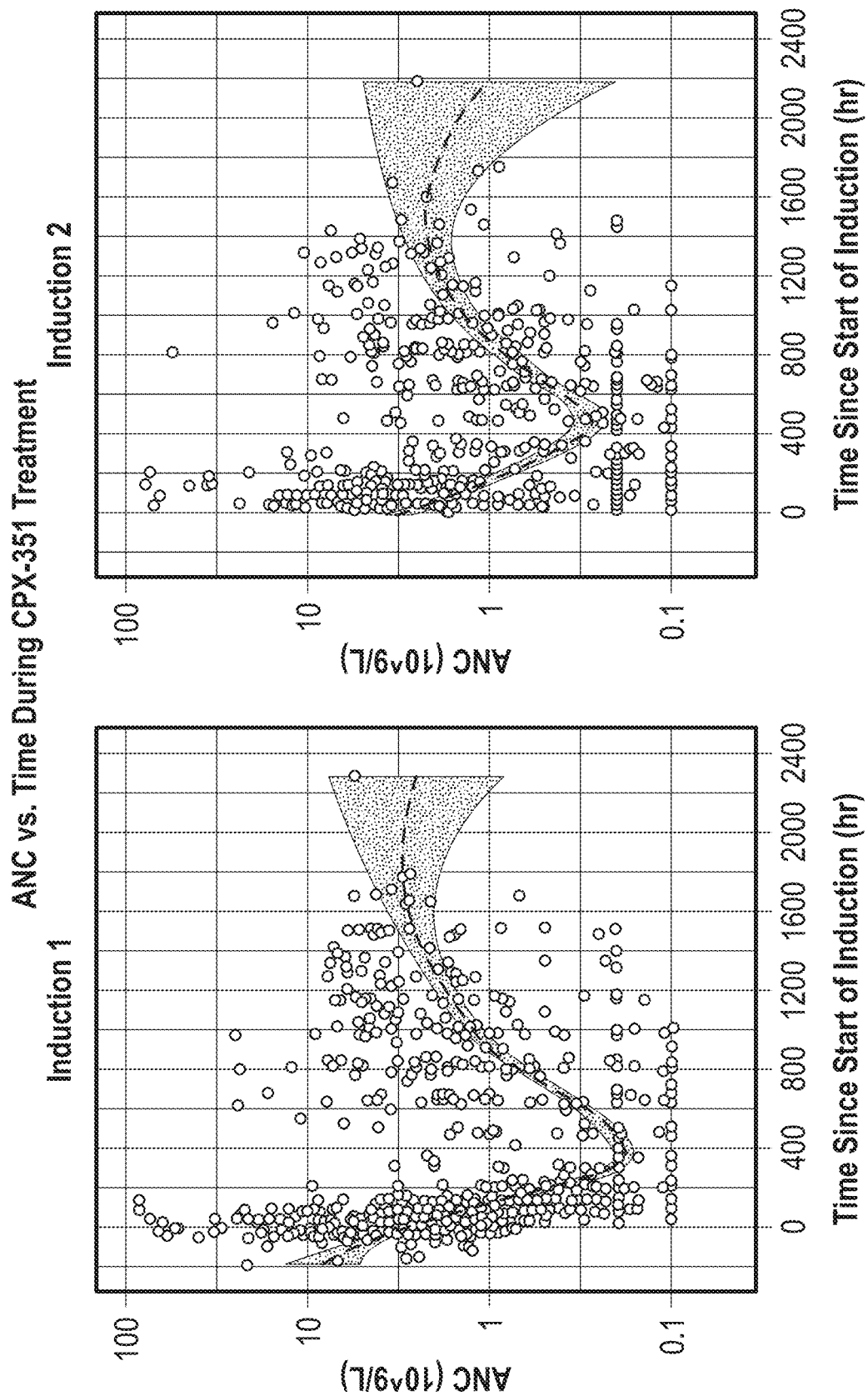
FIGS. 5A-5B show the ANC vs. Time During CPX-351 Treatment
Figure 5B:
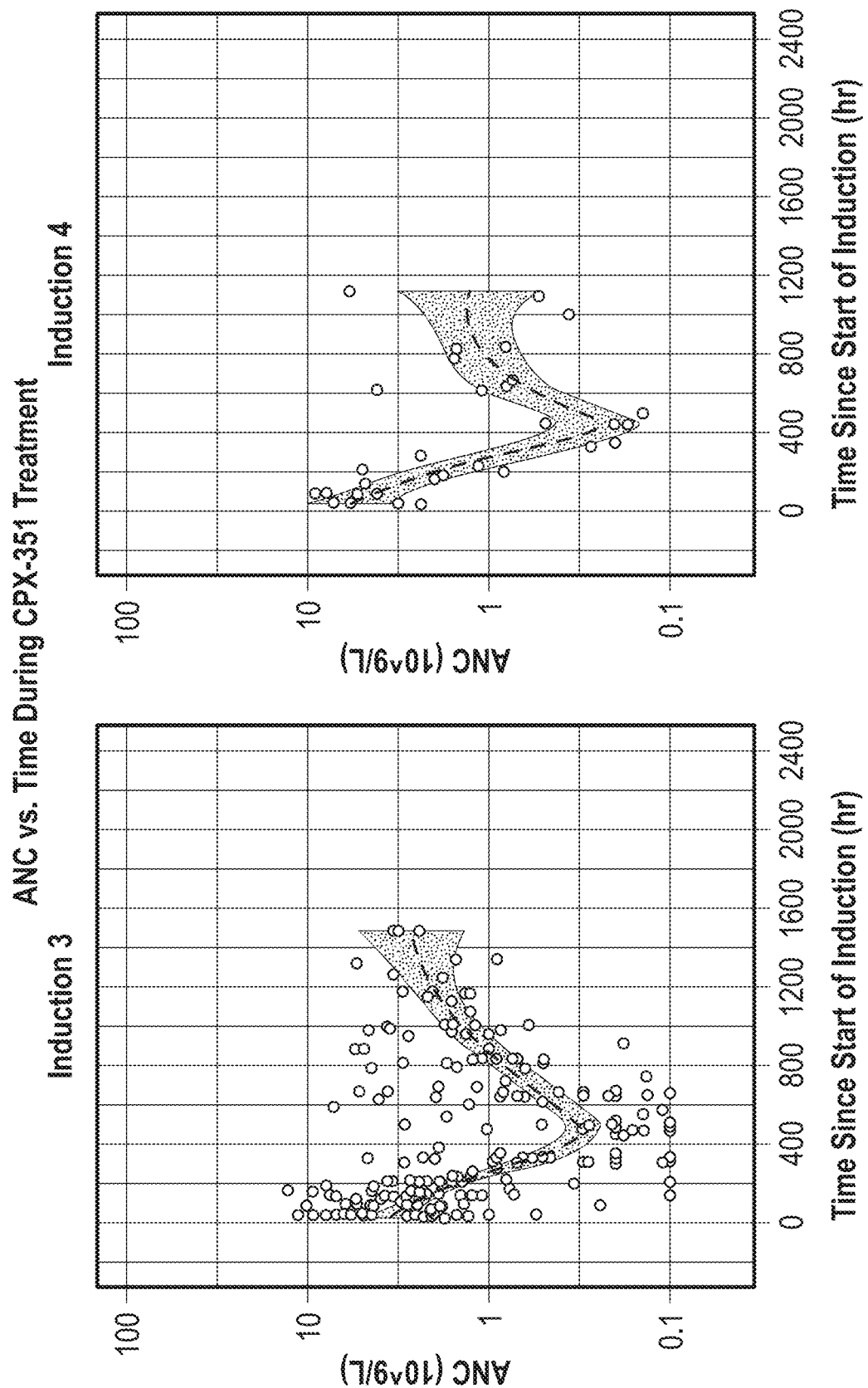
Figure 6A:
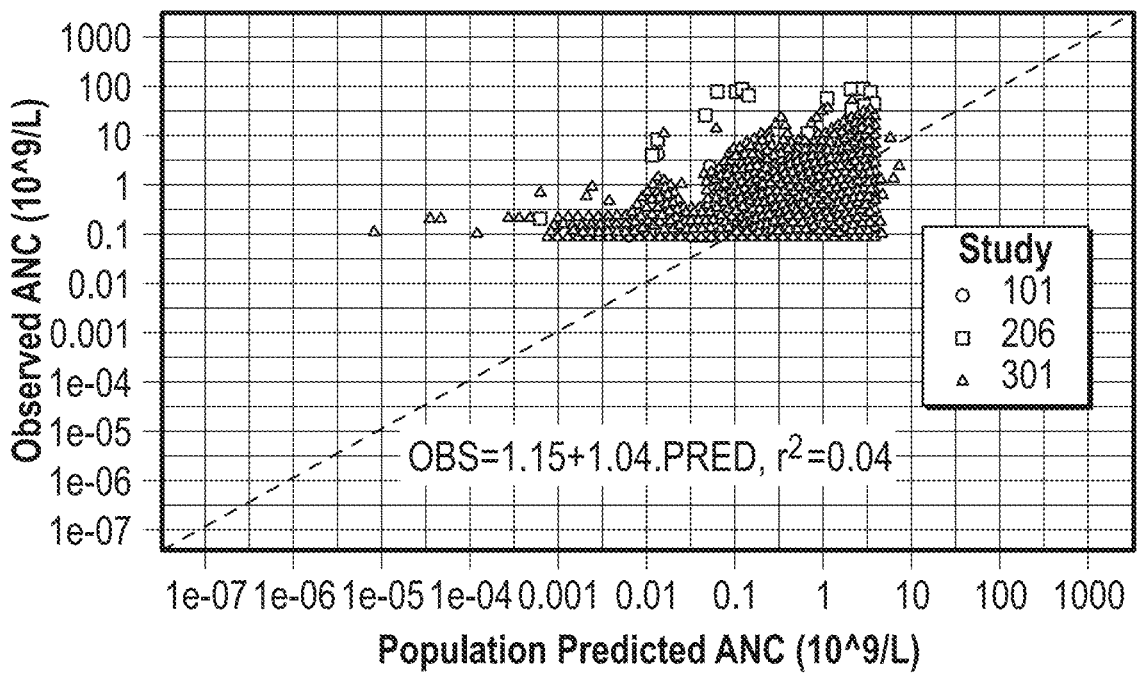
FIGS. 6A-6F show the GOF (goodness-of-fit) Plots: Base CPX-351 PK-PD Model for Neutrophils.
Figure 6A:
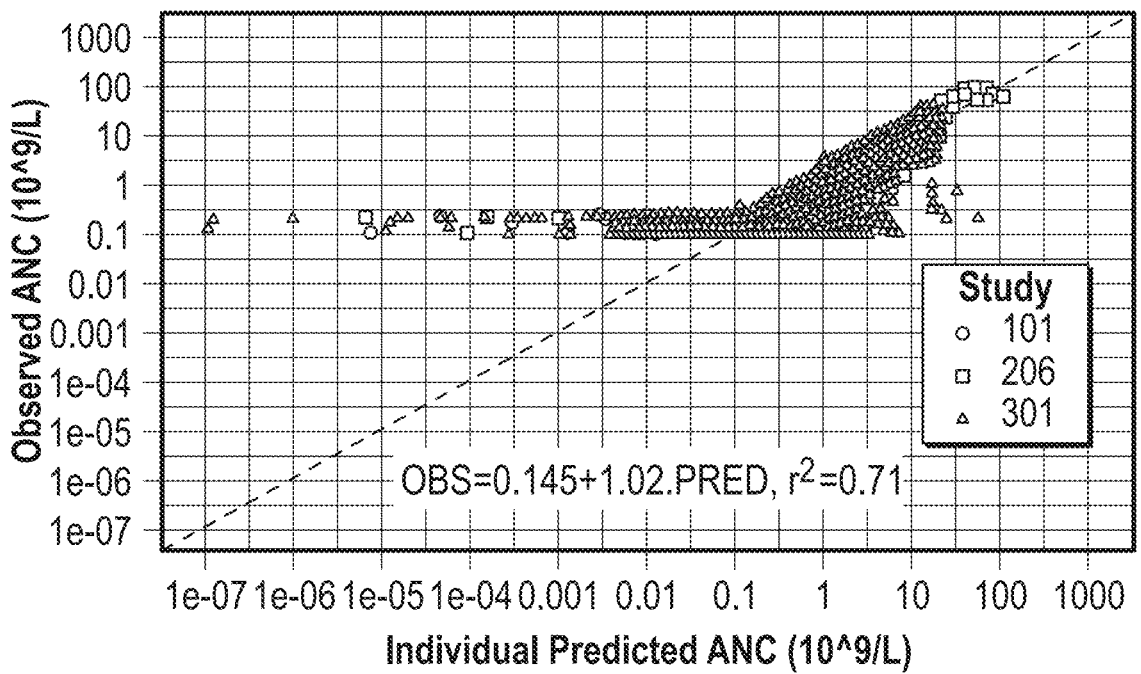
Figure 6B:
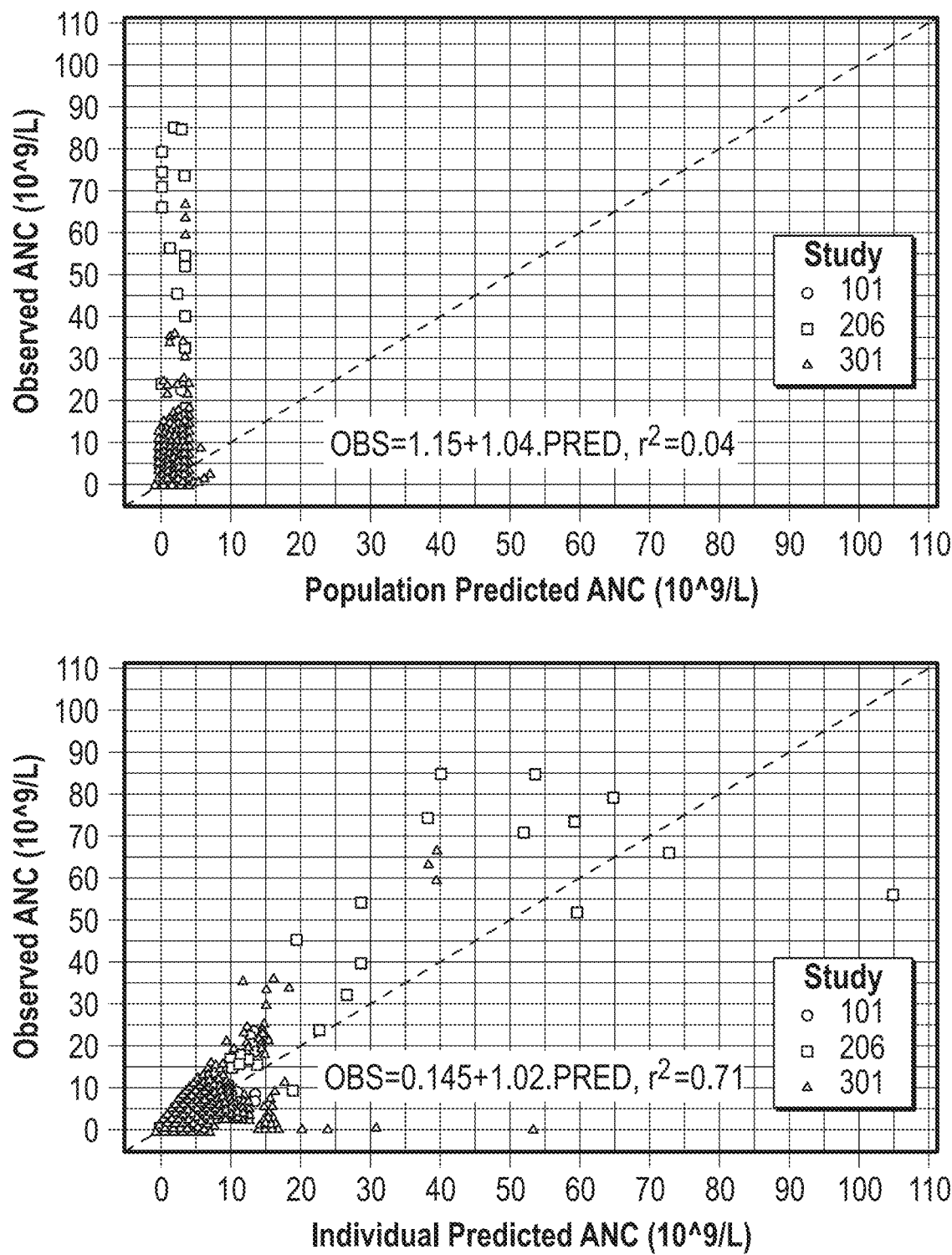
Figure 6C:
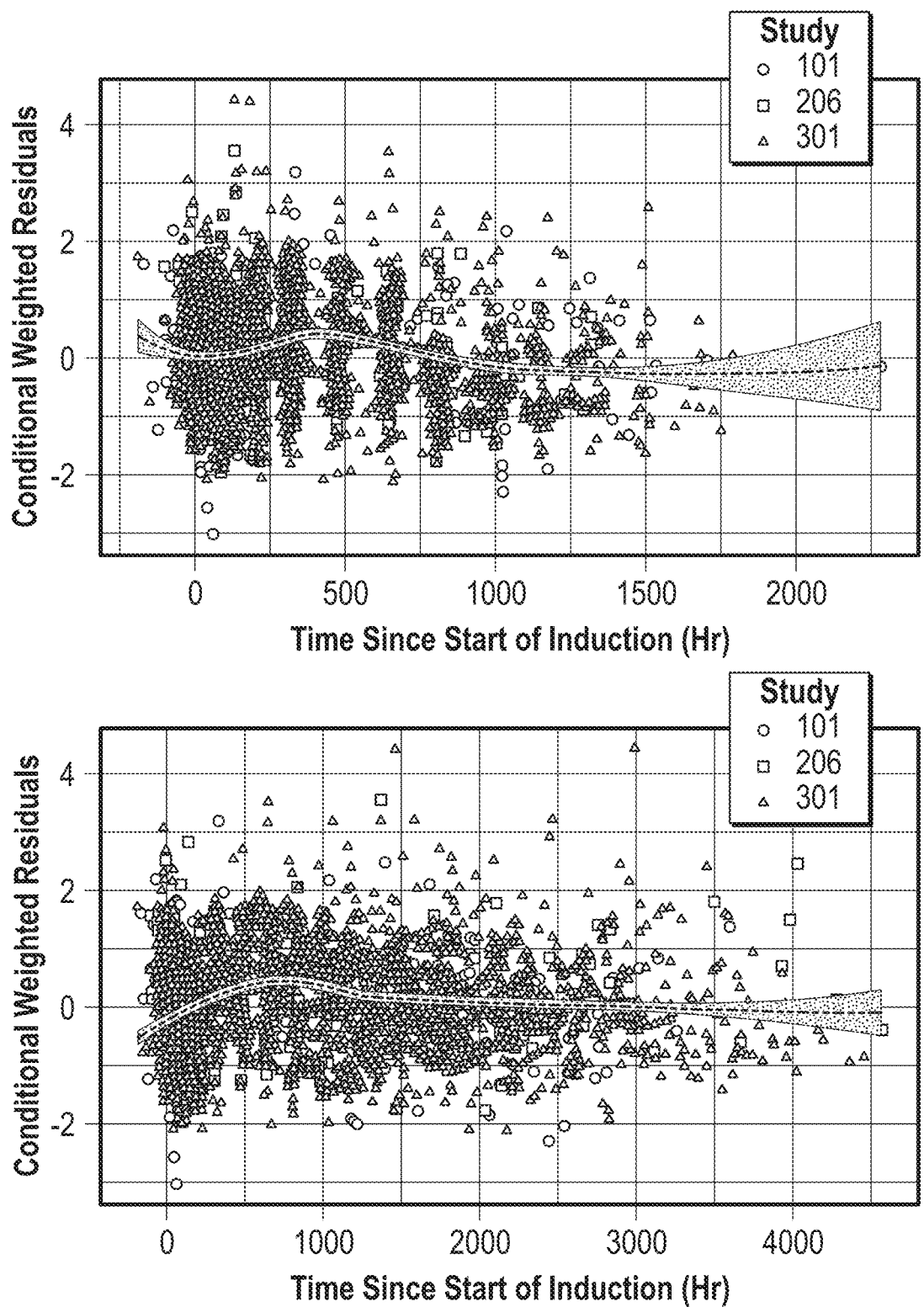
Figure 6D:
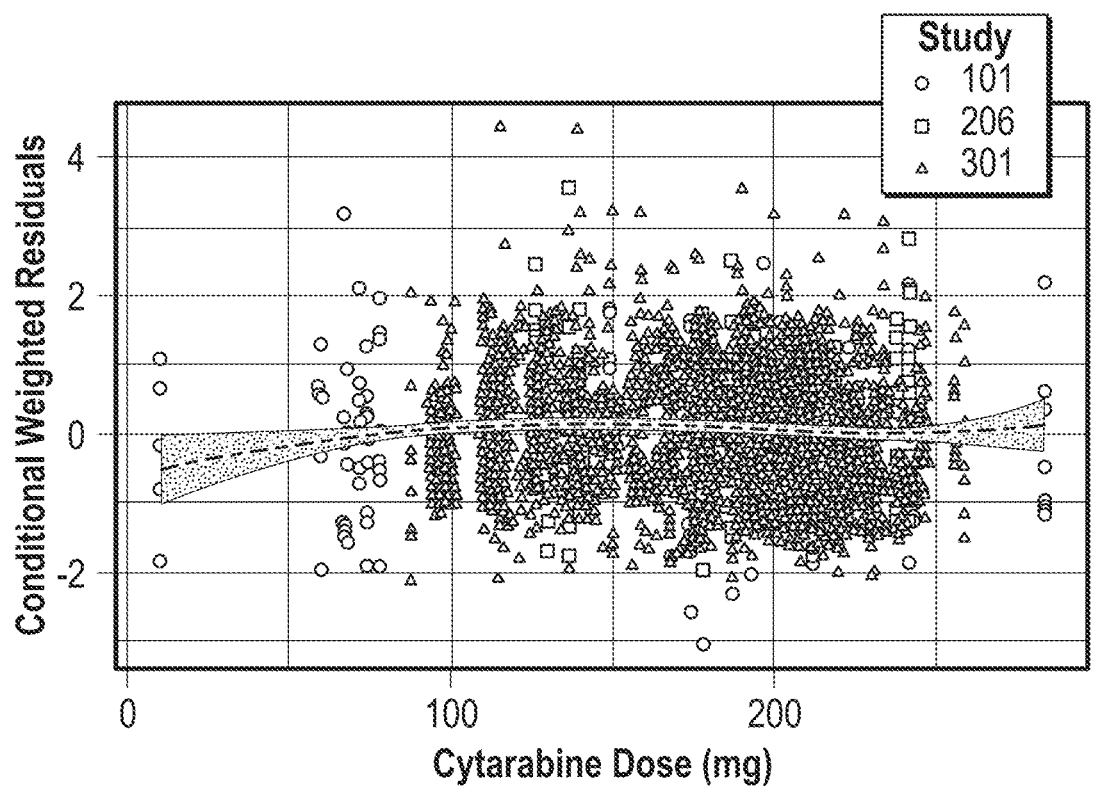
Figure 6D:
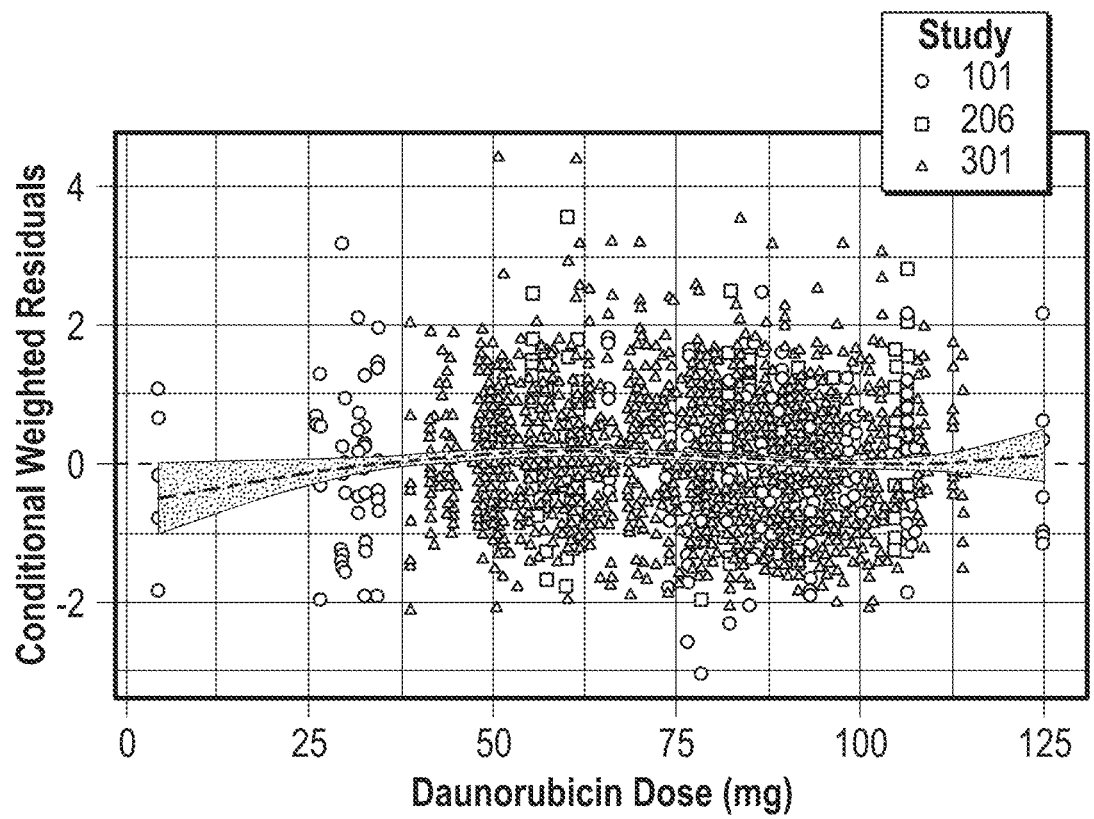
Figure 6E:
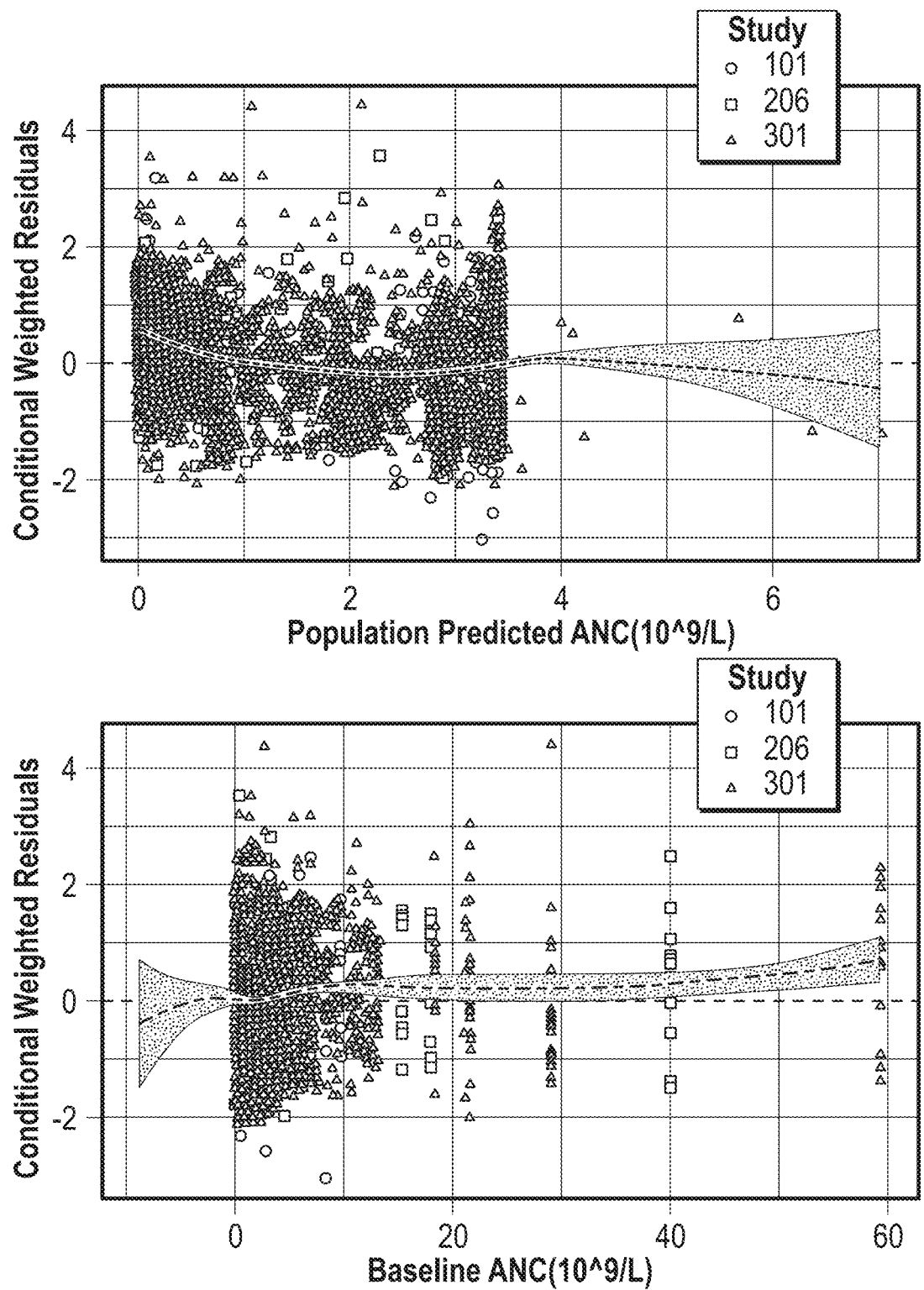
Figure 6F:
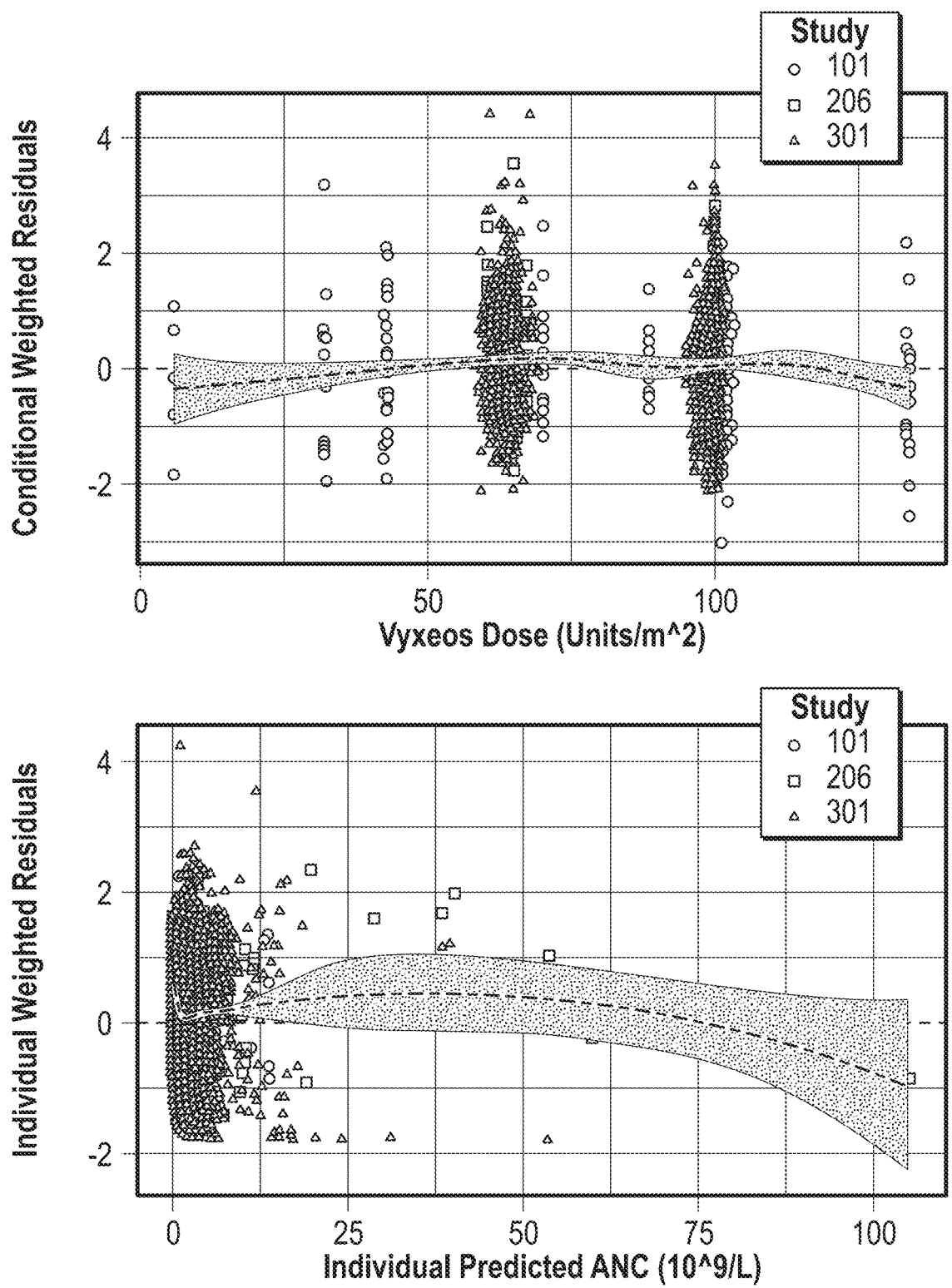
Figure 7:
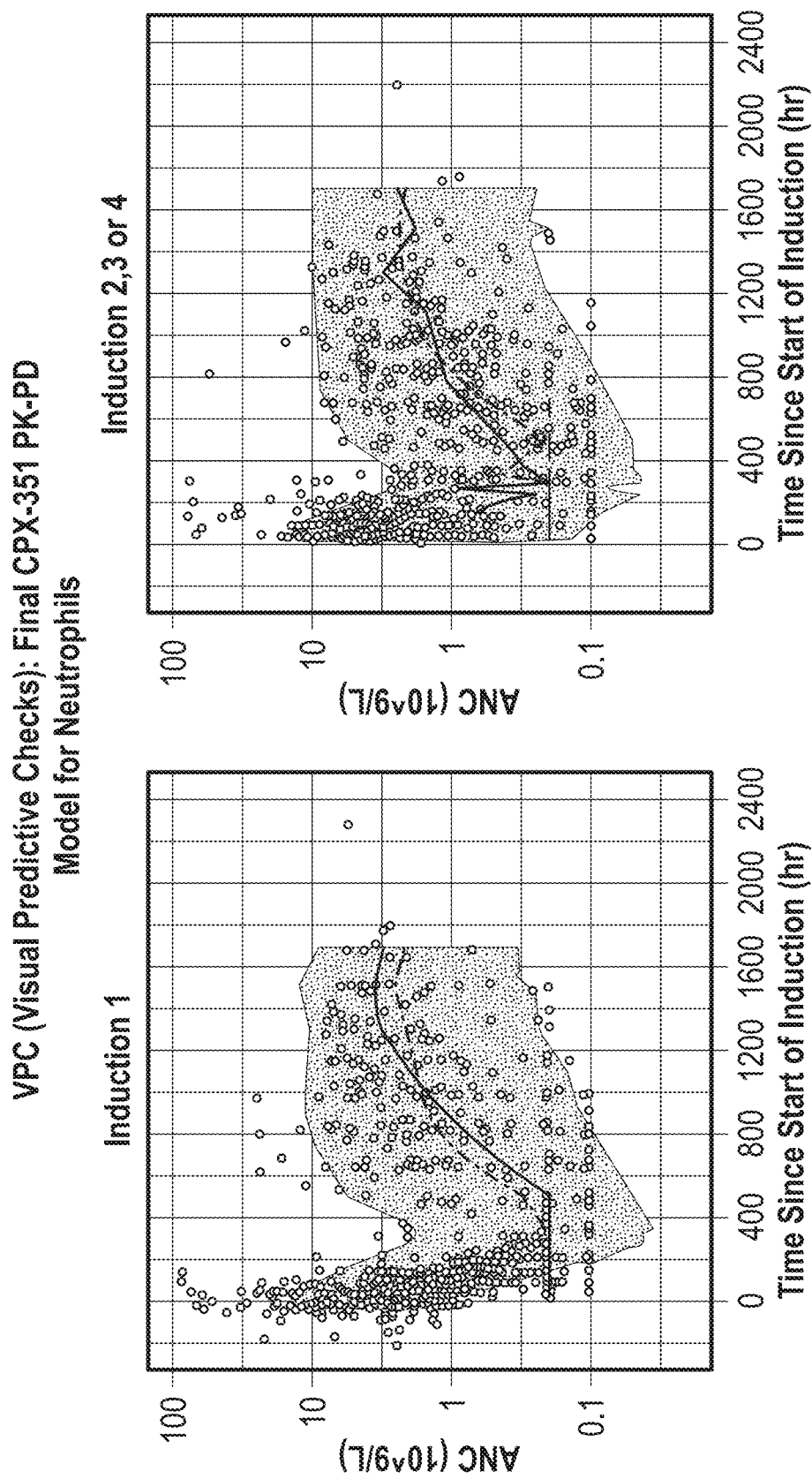
FIG. 7 shows the VPC (Visual Predictive Checks): Final CPX-351 PK-PD Model for Neutrophils

FIGS. 2A-2C show Visual Predictive Check Stratified by Treatment Cycle for the Final Population PK-PD Model.

A visual predictive check based on 100 simulated datasets showed reasonably good agreement between the median and the 10th and 90th percentiles of the observed and simulated platelet counts over time since the start of the treatment cycle. For the final dataset, the R Shiny application was used to simulate 200 patients undergoing chemotherapy with either 100 units/m² of CPX-351 via 90-minute IV infusion at 0, 48, and 96 hours (FIGS. 1B and 1C) or with 7+3 as administered in Study 301. Without platelet transfusions, 186 (93.0%) patients reached incomplete recovery (platelet count >50×$10^9$/L) within the 96-day simulation period, and the median time from first CPX-351 dose to recovery of platelet count >50×$10^9$/L was 618 hours (25.8 days). With intermittent platelet transfusions (6 transfusions every 96 hours starting at 240 hours), 191 (95.5%) patients reached incomplete recovery (platelet count >50×$10^9$/L) within the 96-day simulation period, and the median time from first CPX-351 dose to recovery of platelet count >50×$10^9$/L was 528 hours (22.0 days).

Conclusions: a maturation PK-PD model was developed to characterize the effect of CPX-351 and 7+3 on platelets in patients with AML, ALL, or MDS. CPX-351 achieved a rapid and substantial suppression of platelet counts, with an estimated IC50 of 0.324 μM. The model accounted for the confounding nature of platelet transfusions on platelet dynamics during chemotherapy-induced thrombocytopenia. The final model was successfully embedded in an R Shiny application that can be utilized to evaluate the temporal events of thrombocytopenia following administration of various CPX-351 or 7+3 dosing regimens with intermittent platelet transfusions. These are used to design an appropriate treatment cycle for LiT administration of CPX-351.

Example 2

Modeling of Chemotherapy-Induced Neutropenia (CIN) in Patients Treated with CPX-351 and "7+3"

The CPX-351 and 7+3 studies and Cytarabine/Daunorubicin modeling was performed as in Example 1.

Results shown below:

TABLE 4

Population PK Parameters for GCSF Agents

| Parameter | Population mean equation | Interindividual variability | Reference |
|---|---|---|---|
| Filgrastim | | | |
| $F_i$ | 0.105 | — | Wiczling et al.[5] |
| $k_a$, $h^{-1}$ | 0.403 | — | Wiczling et al.[5] |
| $F_2$ | 0.586 | — | Wiczling et al. |
| $D_2$, h | 6.6 | — | Wiczling et al. |
| $K_D$, nM | 0.0237 | 0.527 (72.6% CV) | Melhem et al. |
| CL, L/h | $0.833 \cdot (WTKG/70)^{0.641}$ | 0.138 (37.1% CV) | Melhem et al. |
| $V_c$, L | $3.12 \cdot (WTKG/70)^{0.943}$ | 0.080 (28.2% CV) | Melhem et al. |
| Pegfilgrastim | | | |
| $F_i$ | 0.646 | 0.194 (44.0% CV) | Melhem et al. |
| $k_a$, $h^{-1}$ | 0.0188 | 0.051 (22.5% CV) | Melhem et al |
| KD, nM | 0.0959 | 0.527 (72.6% CV) | Melhem et al. |
| CL, L/h | $0.362 \cdot (WTKG/70)^{0.641}$ | 0.138 (37.1% CV) | Melhem et al. |
| $V_c$, L | $5.76 \cdot (WTKG/70)^{0.943}$ | 0.080 (28.2% CV) | Melhem et al. |
| Filgrastim or pegfilgrastim | | | |
| $k_{int}$, $h^{-1}$ | 0.113 | 0.325 (57.0% CV) | Melhem et al. |

PK, pharmacokinetic; GCSF, granulocyte colony-stimulating factor; $F_1$, bioavailability of first-order absorption process; $k_a$, first-order absorption rate constant; $F_2$, bioavailability of zero-order absorption process; $D_{2,fil}$, duration of the zero-order absorption process; $K_D$, equilibrium dissociation constant for GCSF and GCSF receptor; CV, coefficient of variation; CL, clearance; WTKG, body weight in kg; $V_c$, central volume of distribution; $k_{int}$, first-order rate constant for internalization of GCSF receptor complexed with filgrastim or pegfilgrastim.

Population PK-PD analysis was conducted using NONMEM version 7.3 via implementation of the first-order conditional estimation method with η-ε interaction. Previously developed population PK models for CPX-351 or 7+3 (2-compartment disposition) were used to generate patient-specific cytarabine and daunorubicin concentration-time profiles. Previously reported population PK models for GCSF agents (1-compartment with target-mediated drug disposition) were used to predict patient-specific concentration-time profiles following exogenous GCSF administration based on individual dosing histories and population mean PK parameters.

In the population PK-PD model for chemotherapy-induced neutropenia (CIN), data from Cycle 1 were excluded if patients had an absolute neutrophil count (ANC)<1.0× $10^9$/L prior to the first treatment cycle; data from subsequent cycles were only included if the ANC returned to >1.0× $10^9$/L prior to treatment. ANC versus time data were described by a modified maturation PK-PD model proposed by Friberg et al. Stimulation of neutrophil proliferation and maturation by exogenous granulocyte colony stimulating factor (GCSF) agents was driven by the fraction of GCSF receptors bound to exogenous GCSF. Inhibition of neutrophil proliferation by CPX-351 (or 7+3) was driven by an $I_{max}$, function of the sum of the molar concentrations of cytarabine and daunorubicin. Interindividual variability was estimated for select structural PK-PD model parameters using exponential error models. Previously reported population PK models for GCSF agents (1 compartment with target-mediated drug disposition) were used to predict patient-specific concentration-time profiles following exogenous GCS F administration (filgrastim and/or pegfilgrastim) based on individual dosing histories and population mean PK parameters. A graphical screening procedure was first conducted to examine the relationship between patient covariates and key PK-PD model parameters, followed by stepwise forward selection (α=0.01) and backward elimination (α=0.001) to evaluate covariate effects. Baseline Patient Demographics were: Weight, height, age, body mass index, body surface area, sex, race, and ethnicity. Baseline Clinical Laboratory Measures were: Albumin, alkaline phosphatase, alanine aminotransferase, aspartate aminotransferase, total bilirubin, white blood cell count, absolute neutrophil count, platelet count, and creatinine clearance. Disease-related Indices were: Cancer type and Eastern Cooperative Oncology Group performance status. An R Shiny application was developed in conjunction with the mrgsolve package (Metrum Research Group) so the population PK-PD model could be used to simulate neutrophil (or platelet) dynamics following administration of CPX-351 (or 7+3) and GCSF in various dosing regimens; relevant patient demographics were generated with distributions that were comparable to those in the analysis dataset.

Results:

TABLE 5

Summary Statistics of Selected Baseline Patient Demographics and Clinical Laboratory Measures in the Final Analysis Dataset

| Variable | | n | % | Mean | SD | Median | Min | Max |
|---|---|---|---|---|---|---|---|---|
| Age, y | | 129 | | 66.1 | 9.1 | 67.0 | 23 | 81 |
| Weight, kg | | 129 | | 82.4 | 20.4 | 78.7 | 39.5 | 156 |
| BSA, m² | | 129 | | 1.96 | 0.28 | 1.94 | 1.3 | 2.8 |
| Platelet count, $10^9$/L | | 129 | | 67.1 | 61.0 | 43.0 | 2 | 289 |
| ANC, $10^9$/L | | 128 | | 4.42 | 7.57 | 1.98 | 0[a] | 59.4 |
| Received ≥1 | No | 86 | 66.7 | | | | | |
| GCSF agent | Yes | 43 | 33.3 | | | | | |
| Sex | Male | 79 | 61.2 | | | | | |
| | Female | 50 | 38.8 | | | | | |
| Race | Caucasian | 110 | 85.3 | | | | | |
| | Black | 6 | 4.7 | | | | | |
| | Asian | 4 | 3.1 | | | | | |
| | Other/missing | 9 | 7.0 | | | | | |

TABLE 5-continued

Summary Statistics of Selected Baseline Patient Demographics and Clinical Laboratory Measures in the Final Analysis Dataset

| Variable | | n | % | Mean | SD | Median | Min | Max |
|---|---|---|---|---|---|---|---|---|
| ECOG performance status | 0 | 39 | 30.2 | | | | | |
| | 1 | 76 | 58.9 | | | | | |
| | 2 | 14 | 10.9 | | | | | |
| Cancer type | ALL | 3 | 2.3 | | | | | |
| | AML | 126 | 97.7 | | | | | |

SD, standard deviation;
BSA, body surface area;
ANC, absolute neutrophil count;
GCSF, granulocyte colony-stimulating factor;
ECOG, Eastern Cooperative Oncology Group;
ALL, acute lymphocytic leukemia;
AML, acute myeloid leukemia.
[a]For patients who were neutropenic (ANC < 1.0 × 10$^9$/L) prior to the first treatment cycle, data from Cycle 1 were excluded from analysis, and data from subsequent cycles were only included if the ANC returned to ≥1.0 × 10$^9$/L prior to treatment. However, for the purposes of covariate evaluation, the baseline ANC from Cycle 1 was used, even if the value was <1.0 × 10$^9$/L.

The early analysis dataset consisted of 1,797 ANC observations from 129 patients, of whom 43 (33.3%) received GCSF therapy at least once during the study. Incorporation of the stimulatory effect of exogenous GCSF on neutrophil proliferation and maturation significantly improved the model fit (P<0.00001). During covariate evaluation, a strong inverse correlation was observed between mean transit time and baseline ANC (P<0.00001); no other potential covariates met the criteria for inclusion. In the late stages of model development, $I_{max}$ was estimated to be 1.05 and subsequently fixed at 1, which produced a minor increase of 4.5 units in the minimum value of objective function.

TABLE 6

Model Fitted PD Parameters for Neutrophils

| Parameter | CPX-351 | | 7 + 3 | |
|---|---|---|---|---|
| | Estimate | % SEM | Estimate | % SEM |
| Circo, 10$^9$/L | 3.55 | 8.8 | 3.76 | 10.2 |
| MTT, hat median baseline ANC of 1.98 × 10$^9$/L | 113 | 3.6 | 87.8 | 3.2 |
| Power exponent for MTT-ANC relationship | −0.154 | 17.5 | n/a | n/a |
| $I_{max}$ | 1 | Fixed | 1 | Fixed |
| $IC_{50}$, μM | 24.9 | 6.1 | 0.0286 | 28.8 |
| γ | 1 | Fixed | 1 | Fixed |
| $γ^T$ | 0.0794 | 7.6 | 0.0689 | 5 |
| $Stim_1$ and $Stim_2$ | 2.76 | 9.6 | 2.76 | Fixed |

PK, pharmacokinetic; PD, pharmacodynamic; SEM, standard error of the mean; Circo, baseline ANC; MTT, mean transit time (4/$k_{tr}$); ANC, absolute neutrophil count; $I_{max}$, maximum inhibition of neutrophil proliferation; $IC_{50}$, composite concentration (cytarabine + daunorubicin) at which inhibition is 50% of $I_{max}$; γт, feedback function exponent; $Stim_1$, slope parameter for stimulation of neutrophil proliferation by the fraction of GCSF receptors bound to exogenous GCSF; $Stim_2$, slope parameter for stimulation of neutrophil maturation by the fraction of GCSF receptors bound to exogenous GCSF; $w^2$, interindividual variability; CV, coefficient of variation; $σ^2$, residual variability; SD, standard deviation.

Parameters in the PK-PD model were estimated with high precision (<26% standard error of the mean). The population mean for Circo before treatment was estimated to be similar for CPX-351 and 7+3, while the population mean for MTT of maturation was slightly longer with CPX-351 versus 7+3. 7+3 was more potent than CPX-351. Including GCSF effect in the model significantly improved the model fit.

The median time to observe the first blood neutrophil count <0.5×10$^9$/L was later following CPX-351 (8.3 days) versus 7+3 (7.4 days) treatment. The median duration with neutrophil counts <0.5×10$^9$/L was longer with CPX-351 (23 days) than with 7+3 (14 days). The median lowest neutrophil counts were well below 0.2×10$^9$/L for both CPX-351 and 7+3. These results are summarized in Table 6A below.

TABLE 6A

Model-simulated Neutrophil Parameters After CPX-351 or 7 + 3 Treatment

| | CPX-351 | 7 + 3 |
|---|---|---|
| Mean (SD) nadir, 10$^9$/L | 0.177 | 0.157 |
| | (0.503) | (0.417) |
| Median nadir, 10$^9$/L | 0.007 | 0.026 |
| Median time to nadir, h | 420 | 312 |
| Median time to 0.5 × 10$^9$/L, h | 199 | 178 |
| Median duration <0.5 × 10$^9$/L, h | 548 | 328 |

Figure 1D:
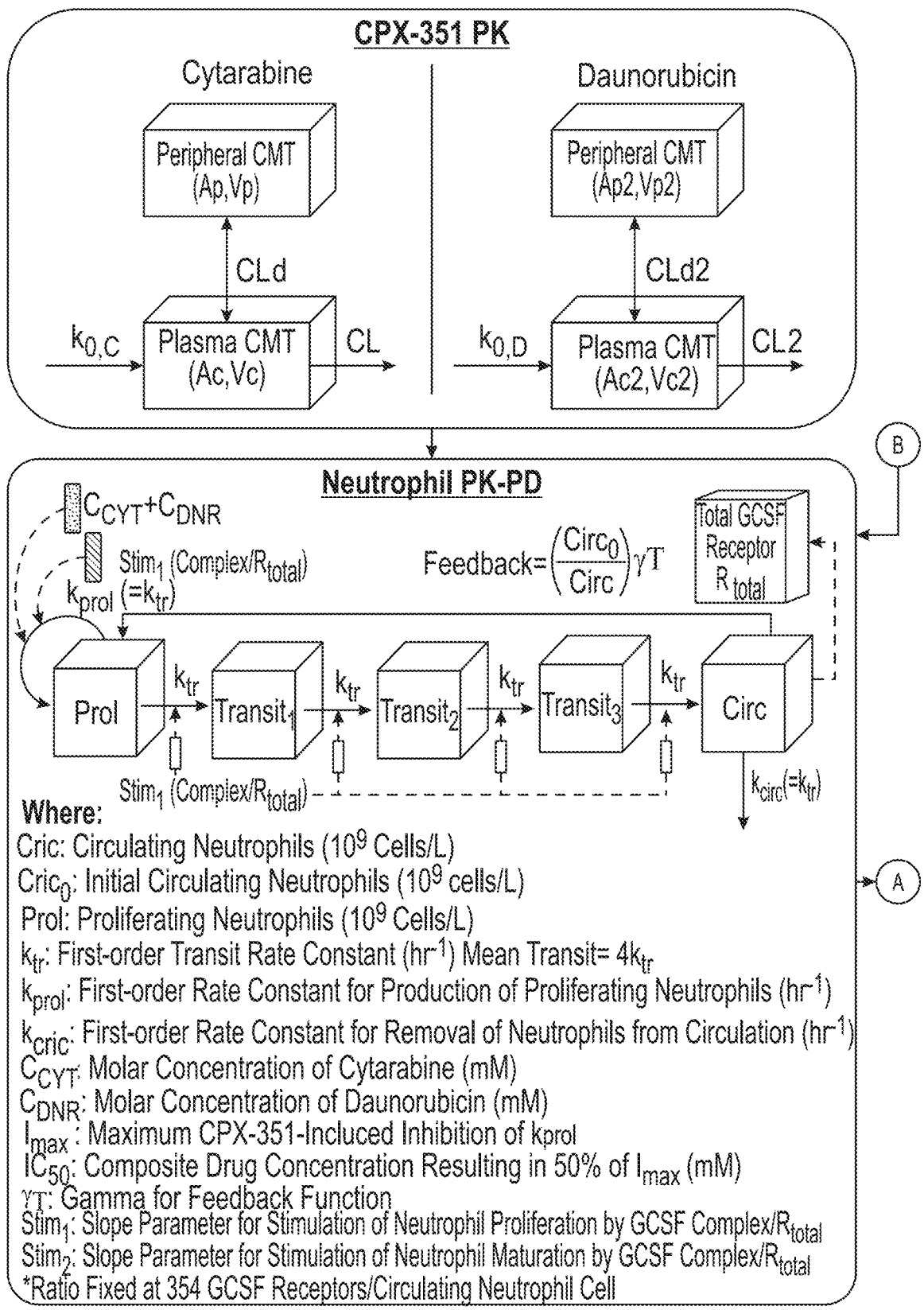
Figure 1E:
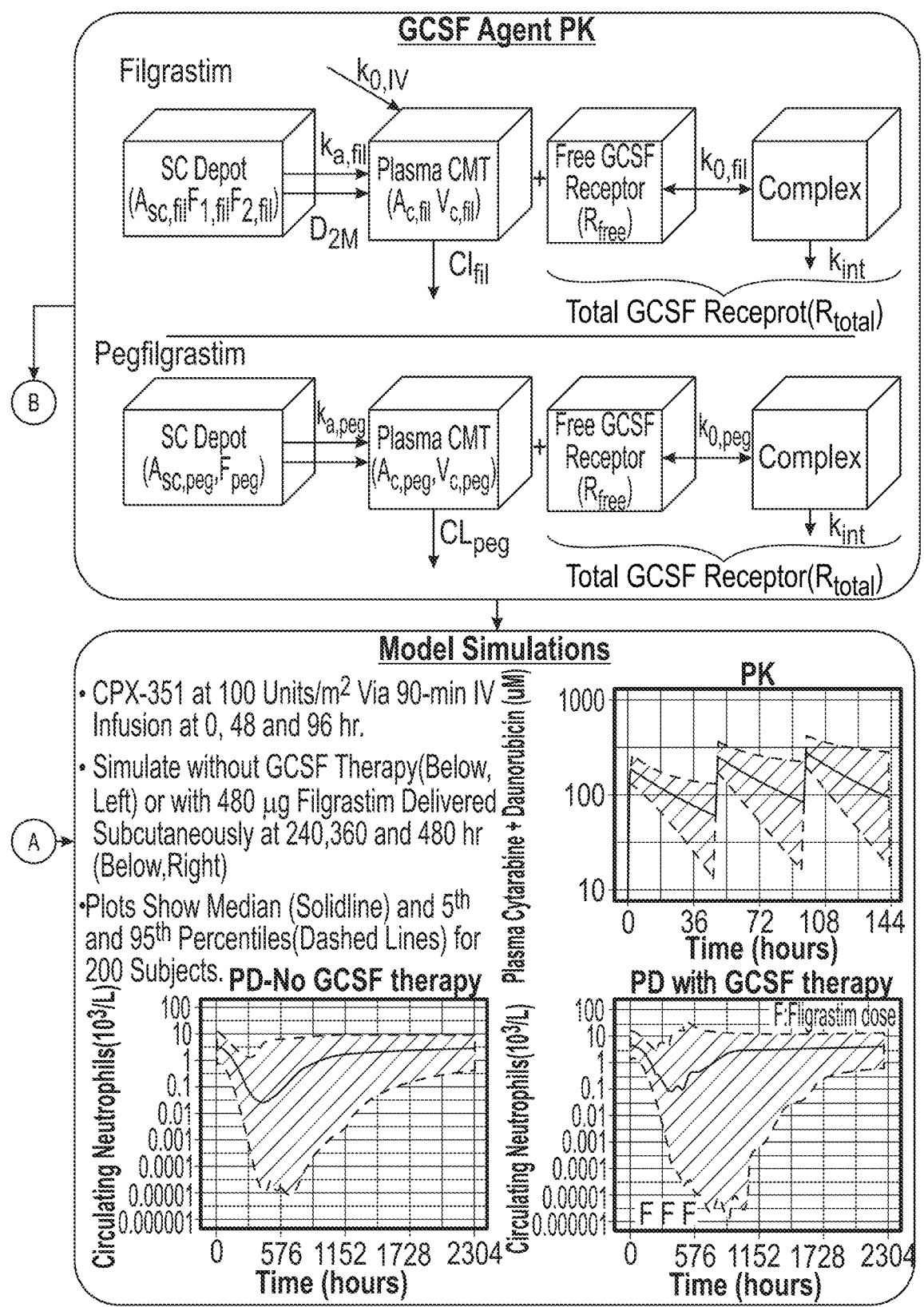
Figure 1F:
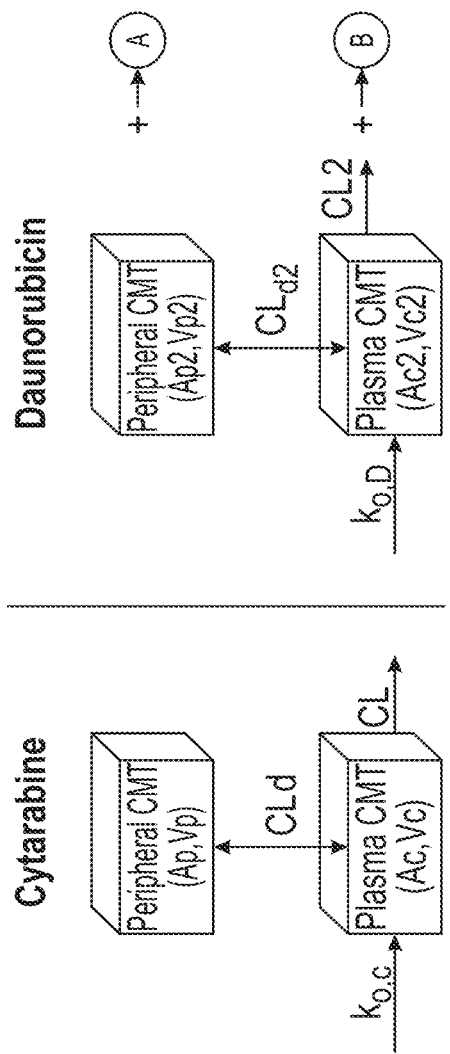
FIGS. 1F and 1G show a schematic representation of the modeling strategy
Figure 1G:
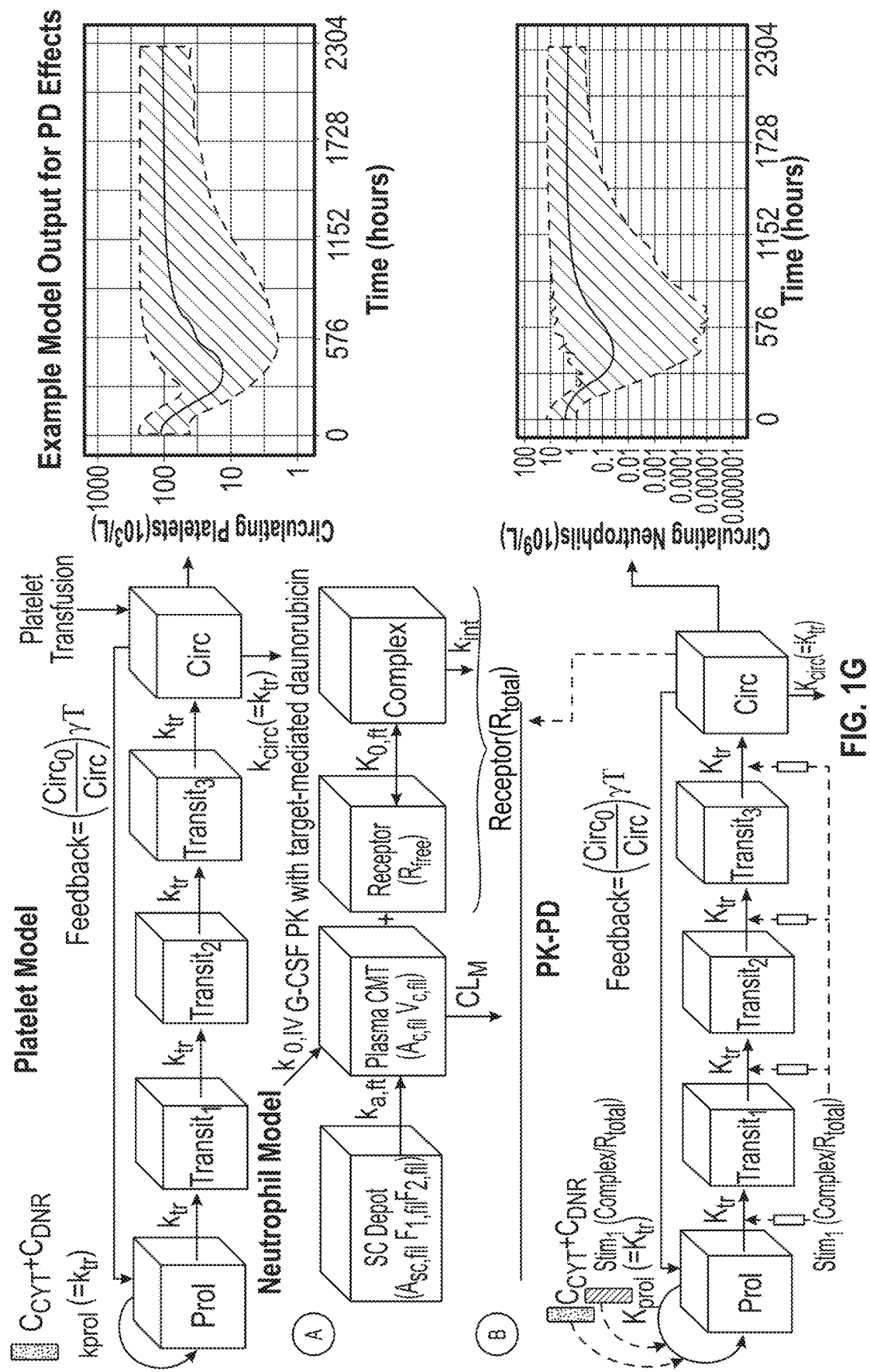

FIG. 2B shows a visual predictive check stratified by treatment cycle for the final population PK-PD model. It is based on 100 simulated datasets showed reasonably good agreement between the median and the 10th and 90th percentiles of the observed and simulated ANC over time since the start of the treatment cycle. The R Shiny application was used to simulate 200 patients undergoing chemotherapy with 100 units/m$^2$ of CPX-351 via 90-minute IV infusion at 0, 48, and 96 hours (FIGS. 1D and 1E). Without GCSF therapy, 172 (86%) patients recovered to ANC>1.0× 10$^9$/L within the 96-day simulation period, and the median time from first CPX-351 dose to recovery of ANC>1.0× 10$^9$/L was 788 hours (32.8 days). With GCSF therapy (480 μg filgrastim administered subcutaneously at 240, 360, and 480 hours), 176 (88%) patients recovered to ANC>1.0× 10$^9$/L within the 96-day simulation period, and the median time from first CPX-351 dose to recovery of ANC>1.0× 10$^9$/L was 730 hours (30.4 days).

Conclusions: a maturation PK-PD model was developed to characterize the effect of CPX-351 and 7+3 on ANC in patients with AML or ALL or MDS. CPX-351 achieved a rapid and maximal suppression of ANC (Imax=1) and had an estimated IC50 of 24.9 μM. The model accounted for the confounding nature of concurrent GCSF therapy on neutrophil dynamics during CIN. The final model was successfully embedded in an R Shiny application that can be utilized to evaluate the temporal events of neutropenia following administration of CPX-351 or 7+3 and GCSF therapy in various dosing regimens. The myelosuppressive effects of CPX-351 were different from 7+3 in terms of duration of myelosuppression and time to neutrophil count <0.5×10$^9$/L. The median time for initial detection of myelosuppression with CPX-351 was 1 to 2 days later than with 7+3. Additionally, the median duration of myelosuppressive effects was longer with CPX-351 than with 7+3. These results may have implications for the clinical monitoring scheme of patients with AML who receive CPX-351 therapy. These are used to design an appropriate treatment cycle for LIT administration of CPX-351.

Example 3

Simulation of Alternative Dose-Regimen for CPX-351

Simulation of myelosuppression profile for lower dose/regimen scenarios:

Day 1+5; various doses <100 units/m²
Day 1+8; various doses <100 units/m²
Day 1+8+15; various doses <100 units/m²
Other schemes, various doses <100 units/m²

The PK/PD modeling described in Examples 1 and 2 is used to further examine the cell cycle time and Vyxeos® treatment effect.

Figure 8:
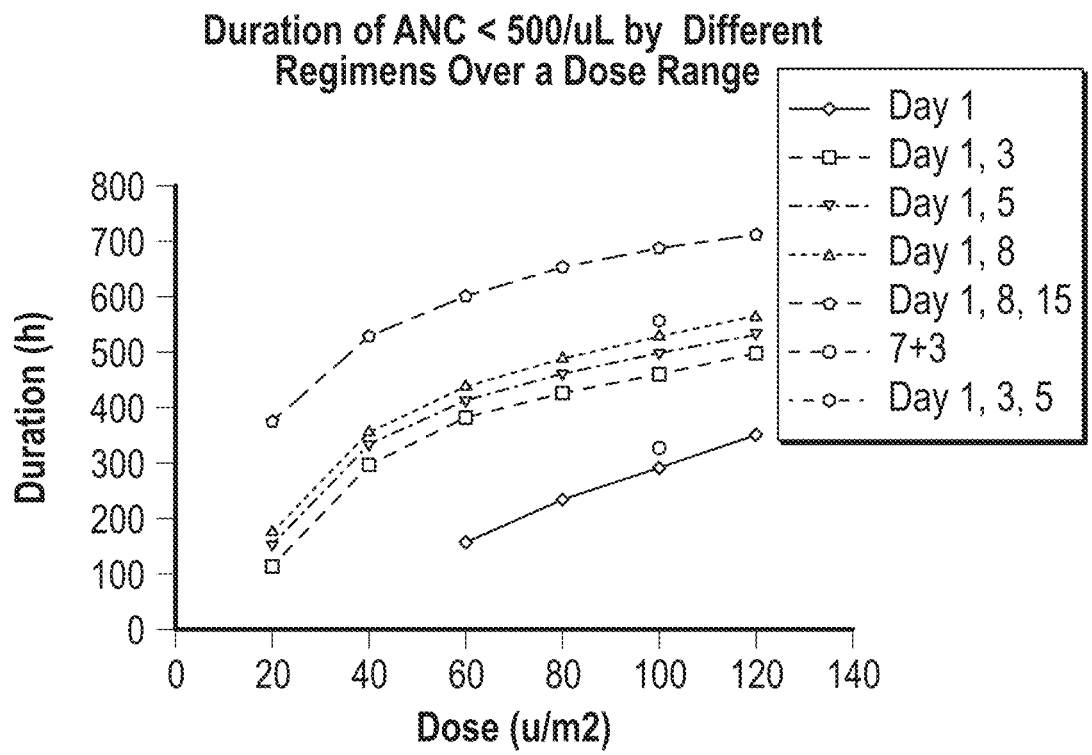
FIG. 8 shows the duration of ANC for a given dose range of CPX-351

Simulation Outcomes for Absolute Neutrophil Count (ANC): Simulations were conducted using previous developed mechanistic PK/PD model for absolute neutrophil count. FIG. 8 shows the period of ANC below 500/uL after administration of CPX-351. The duration of ANC<500/uL increases as dose increases. Depending on regimen, the duration can be different for a given dose. The duration ANC suppression after Vyxeos® standard Day 1, 3, & 5 regimen or 7+3 treatment is also shown in the figure, where Vyxeos® showed a longer duration of ANC suppression than 7+3. This longer suppression is consistent with clinical observations.

Figure 9A:
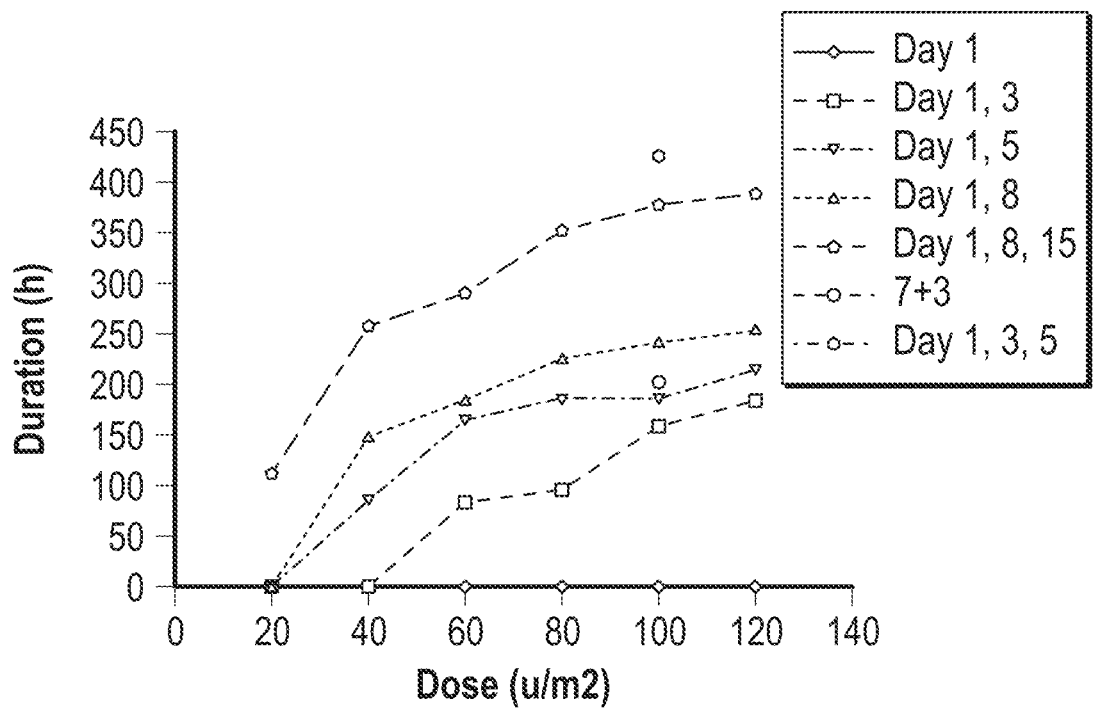
FIGS. 9A and 9B show the duration of platelet count for a given dose range of CPX-351
Figure 9B:
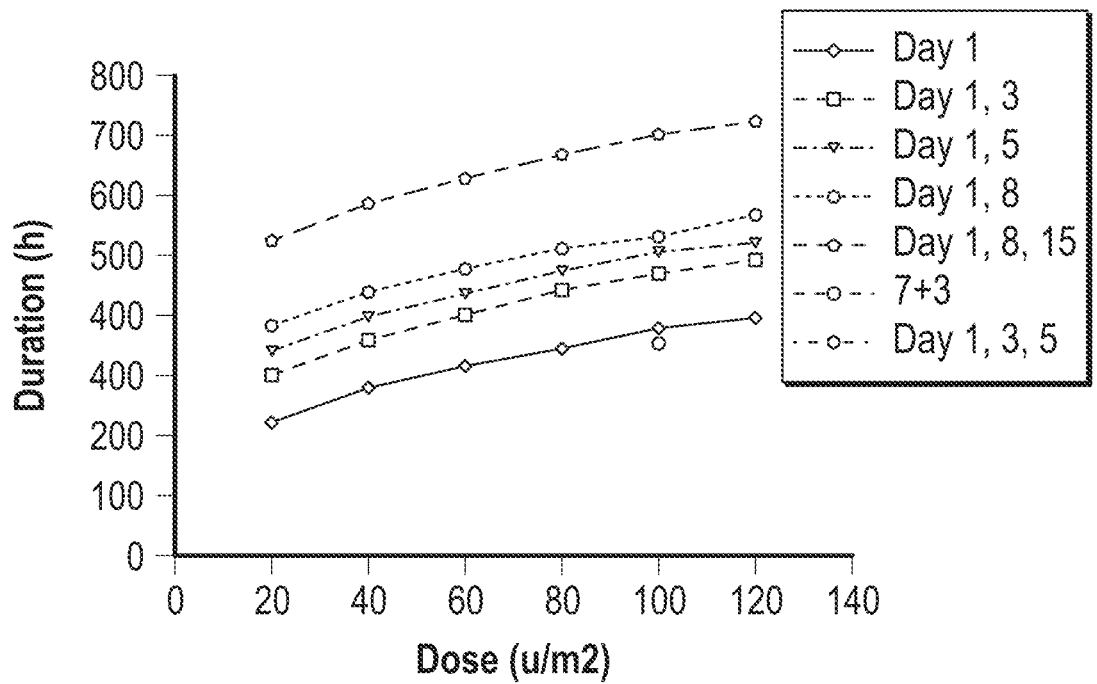

Simulation outcome for platelet count: Simulations were conducted using previous developed mechanistic PK/PD model for platelet count. During simulation, no platelet infusion was given and the starting platelet count is around 10,000/uL. FIGS. 9A and 9B show the period of platelet count below 50,000 or 20,000/uL after administration of CPX-351. The duration of platelet suppression increases as dose increases. Depending on regimen, the duration can be different for a given dose. The duration platelet suppression after Vyxeos® standard Day 1, 3, & 5 regimen or 7+3 treatment is also shown in the figure, where Vyxeos® showed a longer duration of ANC suppression than 7+3. This longer suppression is consistent with clinical observations. Additionally, Vyxeos® Day 1, 3, 5 regimen produced most longest suppression period (<20,000/uL) than other regimens.

Figure 10A:
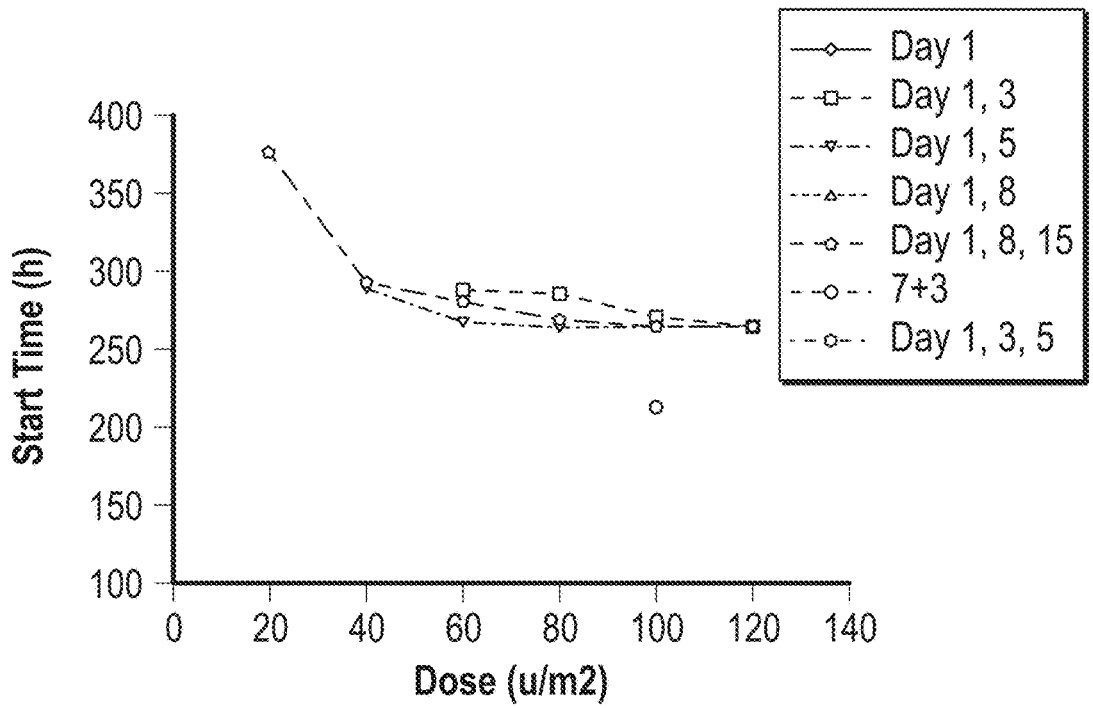
FIGS. 10A and 10B show the first time of different platelet count using different dosing regimen.
Figure 10B:
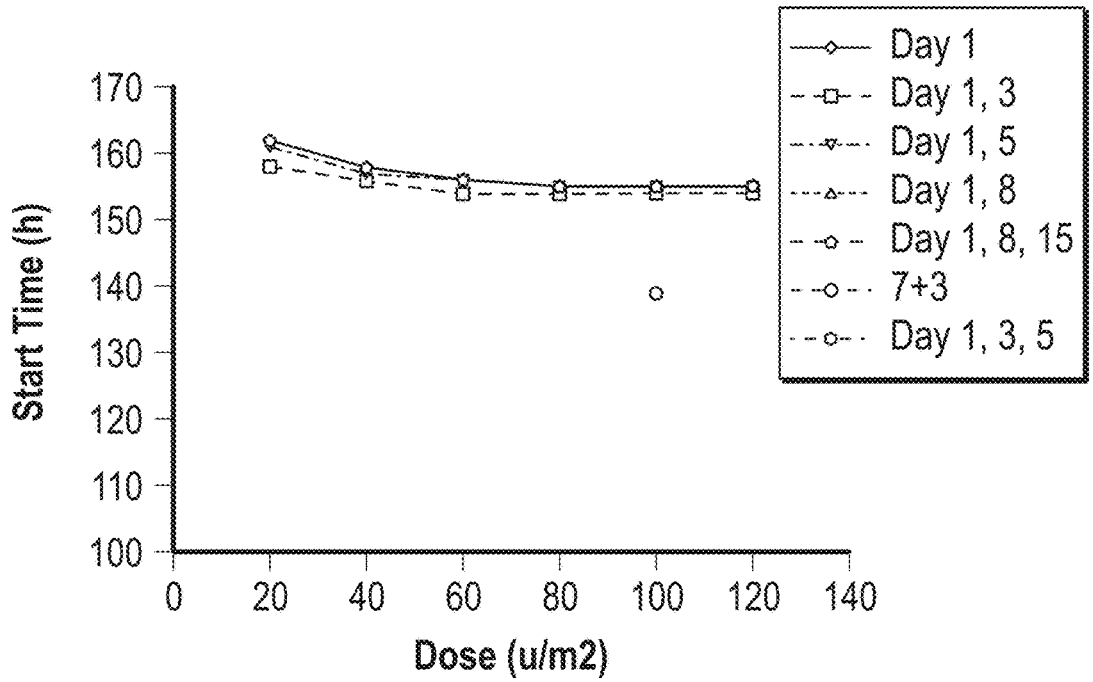

Simulation outcome for platelet count: this data appears to be the first time to observe a platelet count below a certain threshold level that is not related to regimen. Rather, it is related to the drug properties and dose. Vyxeos® treatment results in a later observation than 7+3 treatment. With increase of dose of Vyxeos®, the median start-time of observing platelet count <20,000/uL approaches 258 h (Day 10-11 post the first dose). With increase of dose of Vyxeos®, the median start-time of observing platelet count <50,000/uL approaches 154 h (Day 6-7 post the first dose). For 7+3, the median start-time of observing platelet count <20,000/uL is around 200 h (Day 8-9 post start of the treatment). For 7+3, the median start-time of observing platelet count <50,000/uL is around 139 h (Day 5-6 post start of the treatment). The results are shown in FIGS. 10A and 10B.

Figure 11:
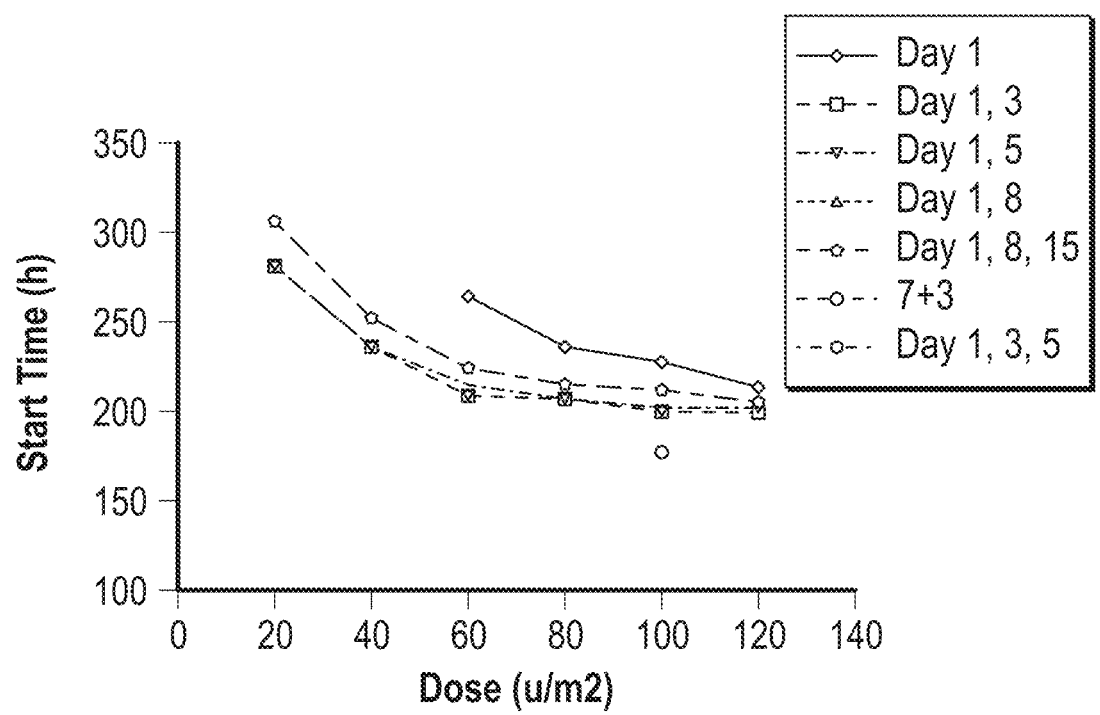
FIG. 11 show the first time of different ANC using different dosing regimen.
Figure 12A:
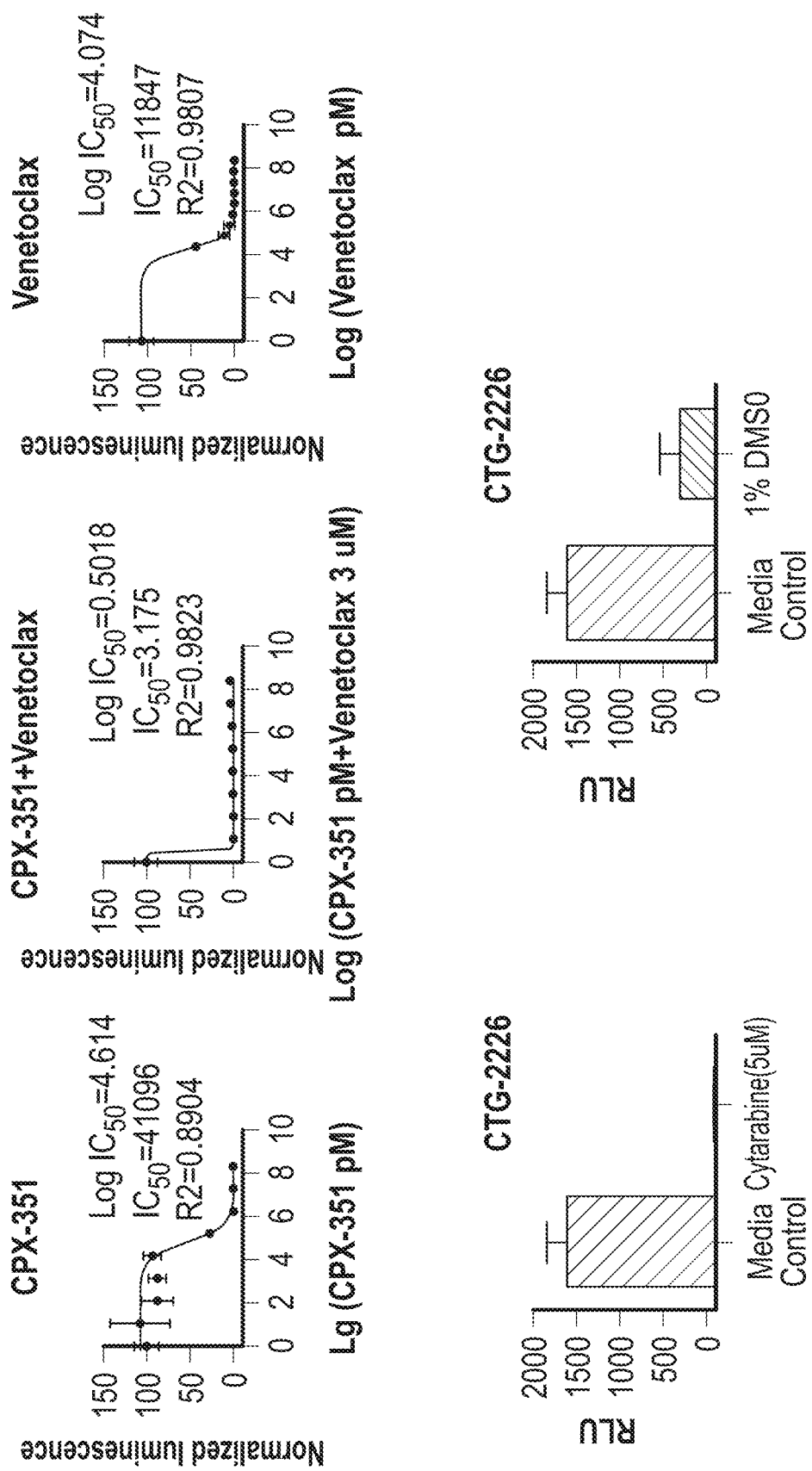
Figure 13A:
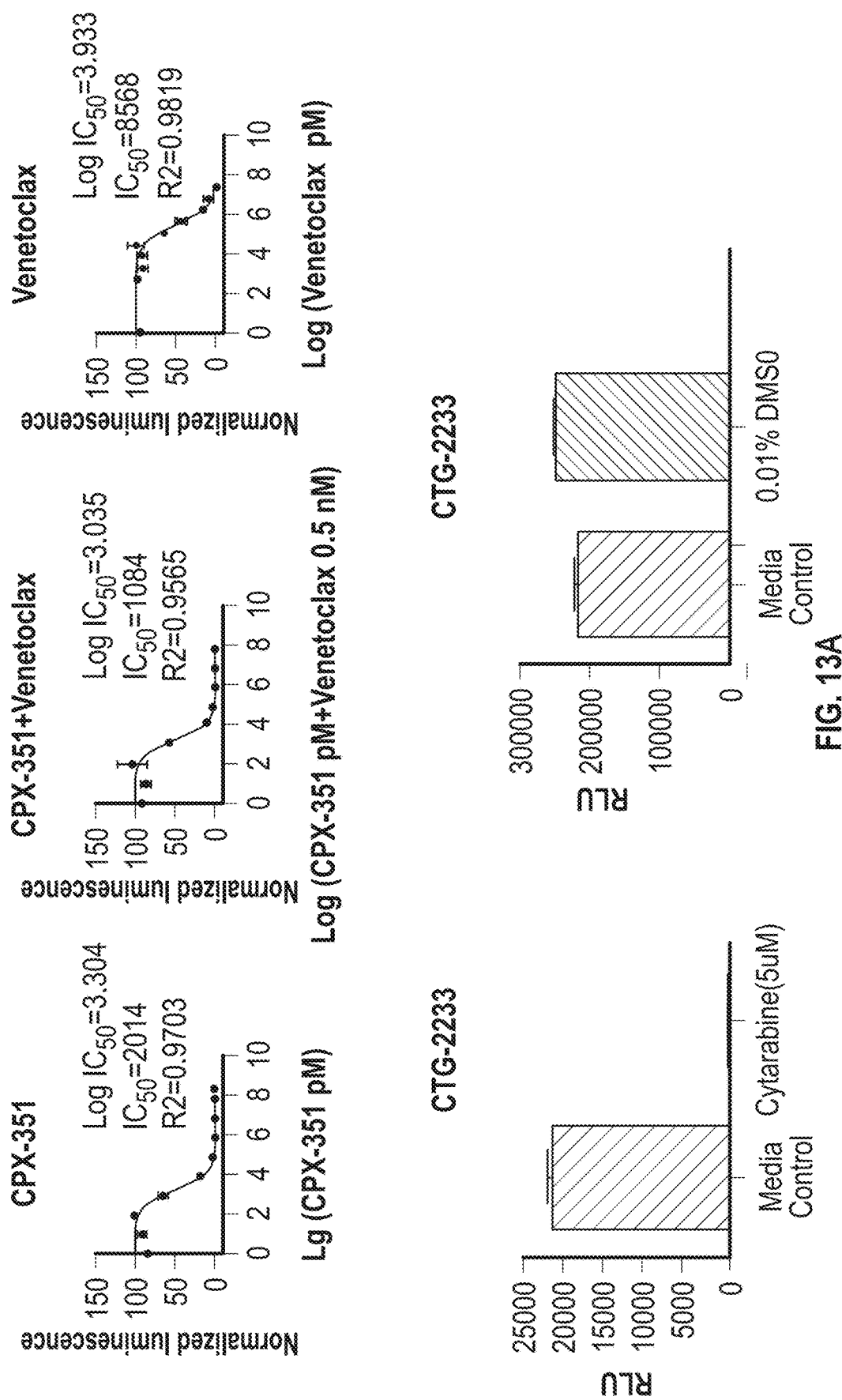

Simulation outcome for neutrophils: this data appears to be the first time to observe a ANC below a certain threshold related to the drug properties and dose. Vyxeos® treatment results in a late-onset but prolonged neutropenia than 7+3 treatment. With increase of dose of Vyxeos®, the median start-time of observing ANC<500/uL approaches 200 h (Day 8-9 post the first dose). For 7+3, the median start-time of observing ANC<500/uL is around 178 h (Day 7-8 post start of the treatment). The results are shown in FIG. 11.

Example 4

CPX-351 and Venetoclax Show Synergy in Ex Vivo Leukemia Models

In order to evaluate the cytotoxicity of CPX-351 in combination with Venetoclax, various drug: drug combinations were tested in 15 Passage 1 (P1) models of human Acute Myeloid Leukemia (AML) and assayed for cell viability.

The study type and duration used was an ex-vivo cell killing assay with primary leukapharesis-derived AML cells using a 96-well plate format, 90 wells, 6-day incubation, Cell Titer Glo viability endpoint with IC50

AML Models used were CTG-2226, CTG-2227, CTG-2228, CTG-2231 to CTG-2234, CTG-2236, CTG-2237, CTG-2238, CTG-2242, CTG-2243, CTG-2251, CTG-2255, and CTG-2299. The IDH1/2 status for each cell line was noted and some were Wildtype while others were IDH1 or IDH2 mutant. AML cells were seeded at a density of 20,000 cells/100 ul per well in a 96 well plate in enriched media. Therapeutic agents were added to wells on Day 0 along with cell plating according to the experimental design in volume of 100 ul/well bringing the total volume to 200 ul/well.

CPX-351 and Venetoclax were each tested alone (100 µM) as well as in combination as outlined in Table 7 below:

TABLE 7

CPX-351 + Venetoclax screening in AML cell models

| Group | -n-replicates | Test Agent | High Dose (uM) | Dilution Series |
|---|---|---|---|---|
| 1 | 3 | CPX-351 | 100 | 10 dose points-1:10 dilutions |
| 2 (1st 7 lines) | 3 | CPX-351 Venetoclax | 100 Fixed @ 3 uM | 10 dose points-1:10 dilutions Fixed |
| 2* (remaining 8 lines) | 3 | CPX-351 Venetoclax | 100 Fixed @ 0.5 nM | 10 dose points-1:10 dilutions Fixed |
| 3 | 3 | Venetoclax | 100 (Reduced starting to 1 uM) | 10 dose points-1:3 dilutions |

Cytarabine (5000 nM) concentration was used as a positive control; Media+vehicle were used as negative control. Plates were kept in 37° C./5% CO2 incubator. Media was not changed during the 6-day incubation period with test agents. On day 6, cell viability was tested using Cell Titer Glo assay.

Cell Titer Glo Assay: Plates were removed from incubator and equilibrated to room temperature up to 30 minutes. 100 ul of Cell Titer Glo was added to wells and mixed for 2 minutes by keeping the plates on plate rocker. The plates were incubated at room temperature for 10 minutes to stabilize luminescent signal. Luminescence was recorded using Tecan plate reader.

Data Analysis: data was reported as changes in RLU units to different drug concentrations as luminescence read is directly proportional to cell viability.

The results from first 7 cells all demonstrated strong synergy. This may be due to the high concentrations of venetoclax in the incubation and so testing of lower concentrations is in progress. The results from remaining 8 cell models demonstrated either synergistic or additive effects of combining Vyxeos® and Venetoclax in 7 cell models, with only showing antagonistic effect. Figures FIGS. 12A, 12B, 13A, and 13B show the change in IC50 for the CTG-2226 and CTG-2233, cell lines respectively.

Example 5

Clinical Trial of CPX-351 and Venetoclax

A Phase 1*b* trial of CPX-351 Lower Intensity Therapy (LIT) plus venetoclax is conducted as First Line Treatment for Subjects with AML who are ineligible for Intensive Chemotherapy.

The primary objectives are to determine the maximum tolerated dose (MTD) of the combination of CPX-351 and venetoclax when administered to subjects with newly diagnosed Acute Myeloid Leukemia (AML) who are ineligible for intensive chemotherapy (ICT). In addition, the safety of this combination is to be determined.

Secondary objections are to perform initial assessments of efficacy, including complete remission (CR), complete remission with incomplete hematologic recovery (CRi), composite complete remission rate (CRc: CR+CRi), overall response rate (ORR; CR+CRi+partial response [PR]) and assessment of Minimal Residual Disease (MRD) status (negative/positive) in subjects with documented CR or Cri. The study is also to determine the pharmacokinetics (PK) of CPX-351 and venetoclax when given in combination.

The duration of remission (DOR) and overall survival (OS) and event-free survival (EFS) 1-year after first administration of the study treatment will also be explored.

The study will comprise 2 phases: a Dose Escalation Phase and an Expansion Phase, in which all subjects will receive a combination of CPX-351 and venetoclax. In the Dose Escalation Phase, a 3+3 design will be employed and enroll up to 24 subjects with newly diagnosed AML who are ineligible for standard ICT using stepwise dose escalations of CPX-351 in combination with 400 mg venetoclax in each cohort to determine the MTD for the combination.

After determining the MTD of the combination of CPX-351 and venetoclax, the Expansion Phase will commence with 20 additional subjects treated with the combination to determine an initial response rate based on both morphologic assessment and MRD. Stopping rules for excessive toxicity and for futility will be included for the Expansion Phase.

Subjects will be followed for safety (1 month after End of Treatment) and every 2 months (±2 weeks) for survival (up to 1 year after the first administration of study treatment). Each subject will be evaluated for response at the end of each cycle. Those subjects with CR, CRi or PR will be offered up to a total of 4 cycles of CPX-351 and venetoclax, as deemed appropriate by the treating physician. Subjects with NR (no response) after 2 cycles will stop treatment. Subjects who have completed 4 cycles of treatment will be managed at the investigator's discretion, as per institutional guidelines.

In each cycle, CPX-351 will be administered on Days 1 and 3, and venetoclax will be administered on Days 2 through 21. During Cycle 2 Day 3 of the Dose Escalation Phase, venetoclax will be administered at the study site during the infusion of CPX-351 to permit PK assessment.

Blood collection for PK studies will be conducted during the first and second cycles of therapy for all dose cohorts in the Dose Escalation Phase. Blood collection for sparse PK sampling will also be performed in the Expansion Phase for subjects receiving their Day 3 and Day 4 care at the study site. During Cycle 1 Day 3 of the Expansion Phase, venetoclax will be administered at the study site during the infusion of CPX-351 to permit PK assessment. The Dose Escalation and Definition of MTD. The Dose Escalation Phase will employ a 3+3 design to determine the DLTs and MTD as follows. The first 3 subjects will be treated at Dose Level 1. If this is deemed safe (see specifics below), then dose escalations will proceed as follows:

Dose escalation algorithm: If none of the first 3 evaluable subjects at a dose level experience a DLT, then the next 3 subjects will be treated at the next dose level (dose escalation), If 1 out of the first 3 evaluable subjects experiences a DLT, then an additional 3 subjects will be treated at the same dose (for a total of 6 subjects at a dose level). If 1 out the 6 total evaluable subjects at a dose level experiences a DLT, then the next 3 subjects will be treated at the next dose level (dose escalation). If 2 or more of the first 3 evaluable subjects at a dose level experience a DLT, then no additional subjects will be treated at this or higher dose level. If 2 or more of the 6 total evaluable subjects experience a DLT, then no additional subjects will be treated at this or higher dose level.

MTD determination algorithm: If >2 out of 3 or ≥2 out of 6 evaluable subjects experience a DLT at Dose Level 1 (starting dose), then the study will stop and no MTD will be determined. Otherwise, the MTD will be determined as the highest dose level at which either 0 out of 3 or 1 out of 6 evaluable subjects experiences a DLT. If this is Dose Level 4, then the maximum administered dose will be Dose Level 4, and for the purposes of this study, Dose Level 4 will be considered the MTD. The DLT observation period will be Days 1 to 49 after starting treatment, with a minimum observation period of 28 days. Subjects who are eligible to progress to a second cycle, or who have transitioned to an alternative therapy, may have an abbreviated DLT observation period (ie, less than 49 days). Subjects who do not complete a full cycle of therapy due to disease-related mortality or who withdraw from the study for reasons unrelated to drug effects, and have not experienced a DLT, will not be evaluable for DLTs. These subjects will be replaced. A regular teleconference, occurring approximately every 3 weeks, will be held among the Jazz medical and clinical team and study investigators to review safety data (hereafter referred to as the Safety Assessment Committee [SAC]). The SAC will also meet at the completion of each dosing cohort to determine whether 1) dose escalation will proceed with the next cohort; 2) the current dose level requires additional assessment; 3) the MTD has been reached; or 4) whether the study will be stopped. To mitigate the risk of potential tumor lysis syndrome, during the first cycle a venetoclax dose ramp-up will occur on Days 2 through 4, followed by treatment at the target dose on Days 5 to 21. For subsequent cycles, venetoclax will be administered at the full target dose during Days 2 through 21.d Main Inclusion Criteria (Full List Provided in Body of Protocol)

Subject must have newly diagnosed AML with histological confirmation by World Health Organization (WHO) criteria Definition of Subjects Who are Ineligible for Standard ICT:
  Each subject must meet the following criteria characterizing him/her as ineligible to receive ICT within 21 days prior to the first day of therapy to be enrolled in the study:
  >75 years of age OR
>18 to 74 years of age and fulfilling at least 1 criteria associated with lack of fitness for ICT as follows:
Eastern Cooperative Oncology Group (ECOG) Performance Status of 2 to 3;
Cardiac history of Congestive Heart Failure (CHF) requiring treatment or left ventricular ejection fraction (LVEF)≤50%.
Diffusing Capacity of the Lung for Carbon Monoxide (DLCO)≤65% or Forced Expiratory Volume in 1 second (FEV1)≤65%;
Creatinine clearance (CrC1)>30 mL/min to <45 mL/min calculated by the Cockcroft-Gault formula;
Moderate hepatic impairment with total bilirubin >1.5 to ≤3.0×Upper Limit of Normal (ULN);
Other comorbidity that the physician judges to be incompatible with conventional intensive chemotherapy which must be reviewed and approved by the study medical monitor before study enrollment.

Additional Criteria:
In addition, all subjects must meet the following criteria:
If the subject is >75 years of age, then ECOG Performance Status must be 0-2.
Subject must have adequate renal function as demonstrated by a CrCl>30 mL/min (calculated by the Cockcroft Gault formula or measured by 24-hour urine collection).
Subject must have adequate liver function as demonstrated by:
Aspartate aminotransferase (AST)<3.0×ULN*
Alanine aminotransferase (ALT)<3.0×ULN*
Bilirubin <1.5×ULN (subjects who are <75 years of age may have bilirubin of <3.0×ULN)*
*Unless considered to be due to leukemic organ involvement.
Female subjects must be either postmenopausal defined as:
Age >55 years with no menses for >2 years without an alternative medical cause.
OR
Age <55 years with no menses for ≥12 months without an alternative medical cause AND a follicle-stimulating hormone level >40 IU/L;
OR
Permanently surgical sterile (bilateral oophorectomy, bilateral salpingectomy or hysterectomy);
OR
A woman of childbearing potential practicing at least 1 protocol specified method of birth control starting at Study Day 1 through at least 6 months after the last dose of study treatment.
A woman of childbearing potential must have negative results for pregnancy test performed:
0 At Pretreatment with a serum sample obtained within 14 days prior to the first study treatment administration, and
Prior to dosing with urine sample obtained on Cycle 1 Day 1, if it has been >7 days since obtaining the serum pregnancy test results.
Subjects with borderline pregnancy tests at Pretreatment must have a serum pregnancy test ≥3 days later to document continued lack of a positive result.
Male subjects who are sexually active, must agree, from Study Day 1 through at least 6 months after the last dose of study treatment, to practice protocol specified methods of contraception. Male subjects must agree to refrain from sperm donation from initial study treatment administration through at least 6 months after the last dose of study treatment.
Subject must have a white blood cell count ≤25×10$^9$/L. (Note: subjects who have undergone hydroxyurea administration or leukapheresis for therapeutic cytoreduction will be considered eligible).
Main Exclusion Criteria (full list provided in body of protocol) Subjects who meet any of the following criteria will be excluded from the study:
Subject has ECOG Performance status >3, regardless of age.
Subject has received any prior treatment for AML with the exception of hydroxyurea, which is allowed up until the initiation of therapy/first dose of CPX-351. (Note: Prior treatment for Myelodysplastic Syndrome is allowed except for use of cytarabine or daunorubicin.)
Subject has favorable risk cytogenetics ((t8;21), inv(16), t(16;16) or t(15;17) karyotype abnormalities) as categorized by the National Comprehensive Cancer Network (NCCN) Guidelines Version 2.2014 for AML
Subject had an antecedent myeloproliferative neoplasm (MPN) including myelofibrosis, essential thrombocytosis, polycythemia vera, or chronic myelogenous leukemia (CML) with or without BCR-ABL 1 translocation and AML with BRC-ABL 1 translocation.
Subject has acute promyelocytic leukemia (APL).
Subject has known Central Nervous System (CNS) involvement with AML.
Subject has known Human Immunodeficiency Virus (HIV) infection (due to potential drug-drug interactions between antiretroviral medications and venetoclax). HIV testing will be performed at Pretreatment, if required per local guidelines or institutional standards.
Subject is known to be positive for hepatitis B virus (HBV), or hepatitis C virus (HCV) infection. (Inactive hepatitis carrier status or low viral hepatitis titer on antivirals [nonexclusionary medications] are not excluded.)
Test Product, Dose and Mode of Administration:
CPX-351 is provided as a sterile, preservative-free, purple, lyophilized cake in a single-use vial. Each vial of CPX-351 contains 44 mg daunorubicin and 100 mg cytarabine. After reconstitution (but before final dilution) each mL contains 2.2 mg daunorubicin and 5 mg cytarabine. CPX-351 is administered as an IV infusion over approximately 90 minutes. Venetoclax is available in 3 strengths and is self-administered as an oral dose once daily with a meal and water:
The 100 mg tablet is provided as an oblong, biconvex shaped, pale yellow film-coated tablet debossed with "V" on one side and "100" on the other side.
The 50 mg tablet is provided as an oblong, biconvex shaped, beige film-coated tablet debossed with "V" on one side and "50" on the other side.
The 10 mg tablet is provided as a round, biconvex shaped, pale yellow film-coated tablet debossed with "V" on one side and "10" on the other side.

The invention claimed is:
1. A treatment cycle for treating a hematological proliferative disorder in a subject ineligible for standard intensive chemotherapy (an ISICT subject), which treatment cycle comprises administering to the subject:
a pharmaceutical composition comprising CPX-351 at dosages of less than 32 units/m$^2$ per day on 3 days or less of a 28-day cycle, wherein CPX-351 is liposomally encapsulated cytarabine and daunorubicin at a fixed 5:1 molar ratio; and venetoclax on days 2 to 21 of the 28-day cycle.

2. The treatment cycle of claim 1, wherein the administering the pharmaceutical composition is on 2 days at intervals of days 1 and 3 or days 1 and 5 or days 1 and 8.

3. The treatment cycle of claim 1, wherein the dosages are less than 24 units/m$^2$ per day.

4. The treatment cycle of claim 1, wherein the administering the pharmaceutical composition is performed intravenously in less than 3 hours.

5. The treatment cycle of claim 1, wherein the hematologic proliferative disorder is acute lymphocytic leukemia (ALL), acute myeloid leukemia (AML), chronic myelogenous leukemia (CML), chronic lymphocytic leukemia (CLL) or acute promyelocytic leukemia (APL), myelodysplastic syndrome (MDS) or myeloproliferative neoplasm (MPN).

6. The treatment cycle of claim 1, wherein the hematological proliferative disorder is acute myeloid leukemia (AML).

7. The treatment cycle of claim 1, wherein the treatment cycle provides a greater therapeutic effect on the ISICT subject than that achieved with a 7+3 regimen on the ISICT subject.

8. The treatment cycle of claim 7, wherein the greater therapeutic effect is measured as an increase in complete remission rate, prolongation of complete remission duration, prolongation of time to progression, or prolongation of survival of the subject.

9. The treatment cycle of claim 1, wherein the administering the pharmaceutical composition is on 2 days.

10. The treatment cycle of claim 1, wherein the administering the pharmaceutical composition is on 1 day.

11. The treatment cycle of claim 1, wherein the administering the pharmaceutical composition is on 2 days at intervals of days 1 and 3.

12. The treatment cycle of claim 1, wherein the administering the pharmaceutical composition is performed intravenously in 90 minutes or less.

13. The treatment cycle of claim 1, wherein the venetoclax is at a dosage of 400 mg.

\* \* \* \* \*